(12) United States Patent
Koshinsky et al.

(10) Patent No.: US 7,745,119 B2
(45) Date of Patent: Jun. 29, 2010

(54) SYSTEM FOR DETECTING POLYNUCLEOTIDES

(75) Inventors: Heather Koshinsky, El Cerrito, CA (US); Michael S. Zwick, Vacaville, CA (US); K. Yeon Choi, St. Paul, MN (US)

(73) Assignee: Investigen, Inc., Hercules, CA (US)

( * ) Notice: Subject to any disclaimer, the term of this patent is extended or adjusted under 35 U.S.C. 154(b) by 266 days.

(21) Appl. No.: 11/285,025

(22) Filed: Nov. 21, 2005

(65) Prior Publication Data

US 2006/0147958 A1    Jul. 6, 2006

Related U.S. Application Data

(63) Continuation-in-part of application No. PCT/US2004/016118, filed on May 20, 2004.

(60) Provisional application No. 60/471,827, filed on May 20, 2003.

(51) Int. Cl.
*C12Q 1/68* (2006.01)

(52) U.S. Cl. .......................... 435/6; 435/91.1

(58) Field of Classification Search ............... None
See application file for complete search history.

(56) References Cited

U.S. PATENT DOCUMENTS

| | | |
|---|---|---|
| 5,582,989 A | 12/1996 | Caskey et al. |
| 5,641,625 A | 6/1997 | Ecker et al. |
| 5,677,124 A | 10/1997 | DuBois et al. |
| 5,705,333 A | 1/1998 | Shah et al. |
| 5,714,331 A | 2/1998 | Buchardt et al. |
| 5,719,262 A | 2/1998 | Buchardt et al. |
| 5,723,290 A | 3/1998 | Eberwine et al. |
| 5,736,336 A | 4/1998 | Buchardt et al. |
| 5,766,855 A | 6/1998 | Buchardt et al. |
| 5,773,571 A | 6/1998 | Nielsen et al. |
| 5,786,461 A | 7/1998 | Buchardt et al. |
| 5,919,625 A | 7/1999 | DuBois et al. |
| 5,939,262 A | 8/1999 | Dasloske et al. |
| 6,107,470 A | 8/2000 | Nielsen et al. |
| 6,214,982 B1 | 4/2001 | Pasloske et al. |
| 6,218,122 B1 | 4/2001 | Friend et al. |
| 6,228,982 B1 | 5/2001 | Norden et al. |
| 6,280,946 B2 * | 8/2001 | Hyldig-Nielsen et al. ...... 435/6 |
| 6,287,772 B1 | 9/2001 | Stefano et al. |
| 6,355,421 B1 | 3/2002 | Coull et al. |
| 6,357,163 B1 | 3/2002 | Buchardt et al. |
| 6,391,558 B1 * | 5/2002 | Henkens et al. ............ 435/6 |
| 6,399,307 B1 | 6/2002 | Pasloske et al. |
| 6,403,763 B1 | 6/2002 | Lowe |
| 6,414,112 B1 | 7/2002 | Buchardt et al. |
| 6,441,130 B1 | 8/2002 | Egholm et al. |
| 6,451,968 B1 | 9/2002 | Egholm et al. |
| 6,475,721 B2 | 11/2002 | Kleiber et al. |
| 2003/0049673 A1 | 3/2003 | Atkinson |
| 2003/0157500 A1 | 8/2003 | Lowe |
| 2003/0162699 A1 | 8/2003 | Lowe |
| 2005/0214797 A1 | 9/2005 | Lokhov et al. |
| 2006/0004188 A1 | 1/2006 | Leung et al. |
| 2006/0014191 A1 | 1/2006 | Lao et al. |
| 2007/0231821 A1 | 10/2007 | Bupp, II et al. |

FOREIGN PATENT DOCUMENTS

| | | |
|---|---|---|
| CA | 2 516 299 | 9/2004 |
| WO | WO 98/58079 | * 12/1998 |
| WO | WO 99/10536 | 3/1999 |
| WO | WO 01/53526 | 7/2001 |
| WO | WO 03/024314 | 3/2003 |
| WO | WO2004/074447 | 9/2004 |
| WO | WO 2005/017181 | 2/2005 |
| WO | WO 2005/021579 | 2/2005 |
| WO | WO 2005/036126 | 4/2005 |
| WO | WO 2005/044923 | 5/2005 |

OTHER PUBLICATIONS

Schena et al. PNAS vol. 93:10614-10619, 1996.*
Wilhelmsson et al. Nucleic Acids Research vol. 30:e3, pp. 1-4. 2002.*
Arabzadeh, A., et al. "Studies on mechanism of 8-methoxypsoralen-DNA interaction in the darkl," *International Journal of Pharmaceutics*, 237:47-55 (2002).
Barceló, Francisca, et al. "Thermodynamic characterization of the multivalent binding of chartreusin to DNA," *Nucleic Acids Research*, 30(2):4567-4573 (2002).
Benson, Scott C., et al. "Heterodimeric DNA-binding dyes designed for energy transfer: synthesis and spectroscopic properties," *Nucleic Acids Research*, 21(24):5727-5735 (1993).
Biver, Tarita, et al. "Kinetics and equilibria for the formation of a new DNA metal-intercalator: the cyclic polyamine Neotrien/copper(II) complex," *Journal of Inorganic Biochemistry*, 98:33-40 (2004).
Boger, Dale L., et al. "Thiazole Orange as the Fluorescent Intercalator in a High Resolution FID Assay for Determining DNA Binding Affinity and Sequence Selectivity of Small Molecules," *Bioroganic & Medicinal Chemistry*, 9:2511-2518 (2001).
Braña, Miguel F., et al. "Synthesis and antitumor activity of new dendritic polyamines—(imide-DNA-Intercalator) Conjugates: Potent Lck inhibitors," *Eur. J. Med. Chem.*, 37:541-551 (2002).
Carreon, Jay R., et al. "Thiazole Orange-Peptide Conjugates: Sensitivity of DNA Binding to Chemical Structure," *Organic Letters*, 6(4):517-519 (2004).

(Continued)

*Primary Examiner*—Heather G Calamita
(74) *Attorney, Agent, or Firm*—Brinks Hofer Gilson & Lione

(57) ABSTRACT

The present invention relates to methods for detecting the presence or amount of a target polynucleotide. A polynucleotide, target nucleic acid analog, and dye are combined to form a mixture. The optical property of the dye is observed after the mixture is exposed to a stimulating means. Optionally, after the stimulating means is employed, the mixture is compared to a reference value characteristic of the rate of change in the optical property of the dye in a similar mixture containing a known amount of a target polynucleotide/nucleic acid analog hybrid to determine a relative rate of change in the optical property. The change in a property of the mixture after exposure thereto to a stimulating means or the relative rate of change in the optical property of dye in the mixture is correlated with the presence or amount of the specified target polynucleotide in the sample.

34 Claims, 30 Drawing Sheets

OTHER PUBLICATIONS

Chandler, Darrell P., et al. "Affinity Capture and Recovery of DNA at Femtomolar Concentrations with Peptide Nucleic Acid Probes," *Analytical Biochemistry*, 283:241-249 (2000).

Dassonneville, Laurent, et al. "The Plant Alkaloid Usambarensine Intercalates into DNA and Induces Apoptosis in Human HL60 Leukemia Cells," *Anticancer Research*, 19:5245-5250 (1999).

Dees, E. Claire, et al. "A Phase I and Pharmacologic Evaluation of the DNA Intercalator CI-958 in Patients with Advanced Solid Tumors[1]," *Clinical Cancer Research*, 6:3885-3894 (2000).

Demidov, "Stability of peptide nucleic acids in human serum and cellular extracts," *Biochemical Pharmacology*, 48(6):1310-1313 (1994).

Dienes, Zoltan, et al. "Asymmetric Synthesis and DNA Intercalation of (-)-6-[[(Aminoalkyl)oxy]methyl]-4-demethoxy-6,7-dideoxydaunomyciones," *J. Org. Chem.*, 61:6958-6970 (1996).

Eriksson, Maja, et al. "Groove-binding unsymmetrical cyanine dyes for staining of DNA: dissociation rates in free solution and electrophoresis gels," *Nucleic Acids Reserach*, 31(21): 6235-6242 (2003).

Ferry, Dianne M, et al. "Sensitive liquid chromatographic assay for the basic DNA intercalator (N-N-dimethylaminoethyl)-9-amino-5-methylacridine-4-carboxamide and its nitrozrylmethyl quaternary prodrugs in biological samples," *Journal of Chromatography B*, 763:149-156 (2001).

Gianolio, Diego A., et al. "Tethered Naphthalene Diimide Intercalators Enhance DNA Triplex Stability," *Bioorganic & Medicinal Chemistry*, 9:2329-2334 (2001).

Hiraku, Yusuke, et al. "Distamycin A, a minor groove binder, changed enediyne-induced DNA cleavage sites and enhances apoptosis," *Nucleic Acids Research Supplement* No. 2, 2002:95-96 (2002).

Johnson, I. Maria, et al. "De-intercalation of Ethidium Bromide and Acridine Orange by Xanthine Derivatives and Their Modulatory Effect on Anticancer Agents: A study of DNA-directed Toxicity Enlightened by Time Correlated Single Photon Counting," *J. Biomolecular Structure & Dynamics*, 20(5):677-685 (2003).

Kapuscinski, Jan "DAPI: a DNA-Specific Fluorescent Probe," *Biotechnic & Histochemistry*, 70(5):220-233.

Karlsson, H. Jonas, et al. "Groove-binding unsymmetrical cyanine dyes for staining of DNA: syntheses and characterization of DNA-binding," *Nucleic Acids Research*, 31(21) 6227-6234 (2003).

Karlsson, J. Jonas, et al. "Synthesis and DNA Binding Studies of a New Asymmetric Cyanine Dye Binding in the Minor Groove of [poly(dA-dT)]," *Bioorganic & Medicinal Chemistry*, 11:1035-1040 (2003).

Kirschstein, Omar, et al. "Quantitative and sequence-specific analysis of DNA-ligand interaction by means of fluorescent intercalator probes," *J. Mol. Recognit.*, 13:157-163 (2000).

Kondo, Shin-ichi, et al. "Synthesis of a novel intercalator based on 2,2'-binaphthalene bearing dimethylammonium groups," *Bioorganic & Medicinal Chemistry Letters*, 14:1641-1643 (2004).

Kuwabara, Tetsuo, et al. "Classification of DNA-binding mode of antitumor and antiviral agents by the electrochemiluminescence of ruthenium complex," *Analytical Biochemistry*, 314:30-37 (2003).

Lisgarten, John N., et al. "The antimalarial and cytotoxic drug cryptolepine intercalates into DNA at cytosine-cytosine sites," *Nature Structural Biology*, 9(1):57-60 (2002).

Liu, Furong, et al. "The pH-Induced Emission Switching and Interesting DNA-Binding Properties of a Novel Dinuclear Ruthenium(II) Complex," *Inorg. Chem.*, 43(5):1799-1806 (2004).

Luedtke, Nathan W., et al. "RNA-Ligand Interactions: Affinity and Specificity of Aminoglycoside Dimers and Acridine Conjugates to the HIV-1 Rev Response Element," *Biochemistry*, 42(39):11391-11403 (2003).

Maiti, Souvik, et al. "Hoechst 33258 binds to G-quadruplex in the promoter region of human *c-myc*," *Biochemical and Biophysical Research Communications*, 310:505-512 (2003).

Matysiak, Stefan, et al. "Automating Parallel Peptide Synthesis for the Production of PNA Library Arrays," *BioTechniques*, 31:896-904 (2001).

Milano, Michael T., et al. "Migration of Electrons and Holes in Crystalline d(CGATCG)-Anthracycline Complexes X-Irradiated at 4 K," *Radiation Research*, 150:101-114 (1998).

Morozkin, Evgeniy S., et al. "Fluorometric quantification of RNA and DNA in solutions containing both nucleic acids," *Analytical Biochemistry*, 322:48-50 (2003).

Nielsen, Peter E., et al. "Sequence-Selective Recognition of DNA by Strand Displacement with a Thymine-Substitute Polyamide," *Science*, 254:1497-1500 (1991).

Nojima, Takahiko, et al. "Detection of DNA hybridization by use of a lanthanide fluorescent intercalator that specifically binds to double stranded DNA," *Nucleic Acids Research Supplement* No. 1, 2001:105-106 (2001).

Novopashina, D., et al. "Conjugates of Oligo (2'-O-Methylribonucleotides) with Minor Groove Binders as New Sequence-Specific Agents Recognizing Both Grooves of Double-Stranded DNA," *Nucleosides, Nucleotides & Nucleic Acids*, 22(5-8):1179-1182 (2003).

Núñez, Megan E., et al. "Long-Range Guanine Oxidation in DNA Restriction Fragments by a Triplex-Directed Naphthalene Diimide intercalator," *Biochemistry*, 39:6190-6199 (2000).

Önfelt, Björn, et al. "Enantioselective DNA Threading Dynamics by Phenazine-Linked [Ru(phen)$_2$dppx]$^{2+}$Dimers," *J. Am. Chem. Soc.*, 123:3630-3637 (2001).

Ostaszewski, Ryszard, et al. "The Synthesis of a New Type of Anthracene DNA Intercalator," *Bioorganic & Medicinal Chemistry Letters*, 8:2995-2996 (1998).

Ouameur, A. Ahmed, et al. "Thallium-DNA Complexes in Aqueous Solution. Major or Minor groove Binding," *J. Biomolecular Structure & Dynamics*, 20(4):561-565 (2003).

Papadopoulous, Maria V., et al. "4-[3-(2-Nitro-1-imidazolyl)propylamino]-7-chloroquinoline Hydrochloride (NLCQ-1), A Novel Bioreductive Agent as Radiosensitizer In Vitro and In Vivo: Comparison With Tirapazamine," *Oncology Research*, 4:325-333 (20000).

Pelley, Robert, et al. "A phase II pharmacodynamic study of pyrazoloacridine in patients with metastatic colorectal cancer," *Cancer Chemother Pharmacol*, 46:251-254 (2000).

Perrin, Leah C., et al. "DNA targeted platinum complexes: synthesis, cytotoxicity and DNA interactions of *cis*-dichloroplatinum(II) complexes tethered to phenazine-1-carboxamides," *Journal of Inorganic Biochemistry*, 81:111-117 (2000).

Prento, P., et al. "Methyl green-pyronin Y straining of nucleic acids: studies on the effects of staining time, dye composition and diffusion rates," *Biotechnic & Histochemistry*, 78(1):27-33 (2003).

Proudfoot, Emma M., et al. "Probing Site Specificity of DNA Binding Metallointercalators by NMR Spectroscopy and Molecular Modeling," *Biochemistry*, 40:4867-4878 (2001).

Pućkowska, Anna, et al. "Aromatic analogues of DNA minor groove binders—synthesis and biological evaluation," *European Journal of Medicinal Chemistry*, 39:99-105 (2004).

Reddy, Pattubala, A.N. et al. "Metal-assisted light-induced DNA cleavage activity of 2-(methylthio)phenylsalicylaldimine Schiff base copper(II) complexes having planar heterocyclic bases," *Journal of Inorganic Biochemistry*, 98:377-386 (2004).

Reddy, Putta Mallikarjuna, et al. "Sequence Selective Recognition in the Minor Groove of dsDNA by Pyrrole, Imidazole-Substituted Bisbenzimidazole Conjugates," *J. Am. Chem. Soc.*, 125:7843-7848 (2003).

Sajewicz, Waldemar, et al. "Cytotoxicity of some Potential DNA Intercalators (Carbazole, Acridine and Anthracene Derivatives) Evaluated through Neutrophil Chemiluminescence," *J. Appl. Toxicol.*, 20:305-312 (2000).

Schaberle, Fábio, A., et al. "Spectroscopic studies of the interaction of bichromophoric cyanine dyes with DNA. Effect of ionic strength," *Biochimica et Biophysica Acta*, 1621:183-191 2003.

Sovenyhazy, Kristine, M., et al. "Spectroscopic studies of the multiple binding modes of a trimethine-bridged cyanine dye with DNA," *Nucleic Acids Research*, 31(10):2561-2569 (2003).

Stefano, Kyriaki et al. "Diagnostic Applications of PNA Oligomers," *Diagnostic Gene Detection and Quantification Technologies*, 19-39 (Minden ed., 1997).

Takenaka, Shigeori, et al. "An anthracene derivative carrying ferrocenyl moieties at its 9 and 10 positions as a new electrochemically active threading intercalator," *Nucleic Acids Research Supplement* No. 2, 291-292 (2002).

Tok, Jeffrey, B.H., et al. "Novel Synthesis and RNA-Binding Properties of Aminoglycoside Dimers Conjugated Via a Naphthalene Diimide-based Intercalator," *Bioorganic & Medicinal Chemistry Letters* 11, 2987-2991 (2001).

Viola, Giampietro, et al. "Indolo[2,3-b]-Quinolizinium Bromide: An Efficient Intercalator with DNA-Photodamaging Properties," *ChemBioChem,* 3:550-558 (2002).

Wagner, Stephen J. "Virus Inactivation in Blood Components by Photoactive Phenothiazine Dyes," *Transfusion Medicine Reviews,* 16:(1)61-66 (2002).

Wang, Sufen, et al. "Electrochemical determination of interaction parameters for DNA and mitoxantrone in an irreversible redox process," *Biophysical Chemistry,* 104:239-248 (2003).

Wang, Zhenxin, et al. "A temperature-dependent interaction of neutral red with calf thymus DNA," *Spectrochimica Acta Part A,* 59:949-956 (2003).

Wong, Elicia, L.S., et al. "Electronic Detection of Target Nucleic Acids by a 2,6-Disulfonic Acid Anthraquinone Intercalator," *Anal. Chem.,* 75:3845-3852 (2003).

Woods, Craig R., et al. "Synthesis and DNA Binding Properties of Saturated Distamycin Analogues," *Bioorganic & Medicinal Chemistry Letters,* 12:2647-2650 (2002).

Xiao, Yi, et al. "Electrocatalytic intercalator-induced winding of double-stranded DNA with polyaniline," *Chem. Commun. (Camb.),* 7:1540-1541 (2003).

Yamana, Kazushige, et al. "Electrochemical detection of single-base mismatches in DNA by a redox-active intercalator conjugated oligonucleotide," *Nucleic Acids Research Supplement* No. 3, 2003:89-90 (2003).

Yang, Xin, et al. "DNA binding studies of a solvatochromic fluorescence probe 3-methoxybenzanthrone," *Spectrochimica Acta Part A,* 55:2719-2727 (1999).

Adhikary, A., et al., "Ensemble and single-molecule fluorescence spectroscopic study of the binding modes of the bis-benzimidazole derivative Hoechst 33258 with DNA," *Nucleic Acids Research,* 31(8):2178-2186 (2003).

Anikovsky, M., et al., "Photochemical investigation of the triplet state of 3,3'-diethylthiacarbocyanine iodide in the presence of DNA," *Russian Chemical Bulletin, Int'l Ed.,* 50(7):1190-1193 (2001).

Anthoney, D.A., et al., "DNA: Still A Target Worth Aiming At? A Review of New DNA-Interactive Agents," *Am. J. Pharmacogenomics,* 1(1):67-81 (2001).

Arya, D.P., et al., "Neomycin Binding to Watson—Hoogsteen (W-H) DNA Triplex Groove: A Model," *J. Am. Chem. Soc.,* 125:3733-3744 (2003).

Atwell, G.J., et al., "DNA-Directed Alkylating Agents. 7. Synthesis, DNA Interaction, and Antitumor Activity of Bis(hydroxymethyl)- and Bis(carbamate)-Substitute Pyrrolizines and Imidazoles," *J. Med. Chem.,* 41:4744-4754 (1998).

Barry, C.G., et al., "Thermally Inert Metal Ammines as Light-Inducible DNA-Targeted Agents. Synthesis, Photochemistry, and Photobiology of a Prototypical Rhodium (III)—Intercalator Conjugate," *Inorg. Chem.,* 41:7159-7169 (2002).

Baruah, H. and Bierbach, U., "Unusual Intercalation of Acridin-9-ylthiourea into the 5'-GA/TC DNA Base Step from the Minor Groove: Implications for the Covalent DNA Adduct Profile of a Novel Platinum—Intercalator Conjugate," *Nucleic Acids Research,* 31(14):4138-4146 (2003).

Benson, S.C., et al., "Heterodimeric DNA-binding Dyes Designed for Energy Transfer: Stability and Applications of the DNA Complexes," *Nucleic Acid Research,* 21(24):5720-5726 (1993).

Berge, T., et al., "Structural Perturbations in DNA Caused by Bis-intercalation of Ditercalinium Visualized by Atomic Force Microscopy," *Nucleic Acids Research,* 30(13):2980-2986 (2002).

Boutorine, A.S., et al., "Stabilization of DNA Double and Triple Helices by Conjugation of Minor Groove Binders to Oligonucleotides," *Nucleosides, Nucleotides & Nucleic Acids,* 22(5-8):1267-1272 (2003).

Briehn, C.A., et al., "Alternative Heterocycles for DNA Recognition: The Benzimidazole/Imidazole Pair," *Chem. Eur. J.,* 9:2110-2122 (2003).

Carrasco, C., et al., "Design of a Composite Ethidium—Netropsin—Anilinoacridine Molecule for DNA Recognition," *ChemBioChem,* 4:50-61 (2003).

Chaput, J.C., et al., "DNA Polymerase-Mediated DNA Synthesis on a TNA Template," *J. Am. Chem. Soc.,* 125:856-857 (2003).

Chen, Qiu-ying., et al., "Interaction of a Novel Red-region Fluorescent Probe, Nile Blue, with DNA and its Application to Nucleic Acids Assay," *Analyst,* 124:901-906 (1999).

Christensen, U.B. and Pedersen, E.B., "Intercalating Nucleic Acids Containing Insertions of 1-O-(1-pyrenylmethyl)glycerol: Stabilization of dsDNA and Discrimination of DNA over RNA," *Nucleic Acids Research,* 30(22):4918-4925 (2002).

Dempcy, R.O., "Linkers Designed to Intercalate the Double Helix Greatly Facilitate DNA Alkylation by Triplex-forming Oligonucleotides Carrying a Cyclopropapyrroloindole Reactive Moiety," *Nucleic Acids Research,* 27(14):2931-2937 (1999).

Dervan, P.B. and Edelson B.S., "Recognition of the DNA Minor Groove by Pyrrole-imidazole Polyamides," *Current Opinion in Structural Biology,* 13:284-299 (2003).

Dhar, S., et al., "Ternary Copper Complexes for Photocleavage of DNA by Red Light: Direct Evidence for Sulfur-to-Copper Charge Transfer and d-d- Band Involvement," *J. Am. Chem. Soc.,* 125:12118-12124 (2003).

Fiebig, T., et al., "Femtosecond Dynamics of the DNA Intercalator Ethidium and Electron Transfer with Mononucleotides in Water," *Proc. Natl. Acad. Sci. USA,* 96:1187-1192 (1999).

Guelev, V., et al., "Peptide bis-intercalator Binds DNA via Threading Mode with Sequence Specific Contacts in the Major Groove," *Chemistry & Biology,* 8:415-425 (2001).

Guelev, V., et al., "Changing DNA Grooves—A 1,4,5,8-Naphthalene Tetracarboxylic Diimide Bis-Intercalator with the Linker (β-Ala)$_3$-Lys in the Minor Groove," *J. Am. Chem. Soc.,* 124(12):2864-2865 (2002).

Guittat, L., et al., "Interactions of Cryptolepine and Neocryptolepine with Unusual DNA Structures," *Biochimie,* 85:535-547 (2003).

Hicks, K.O., et al., "Extravascular Transport of the DNA Intercalator and Topoisomerase Poison N-[2-(Dimethylamino)ethyl]acridine-4-carboxamide (DACA): Diffusion and Metabolism in Multicellular Layers of Tumor Cells," *The Journal of Pharmacology and Experimental Therapeutics,* 297(3):1088-1098 (2001).

Huang, X., et al., "Rational Design of Pyrrolo[1,2-a]benzimidazole-Based Antitumor Agents Targeting the DNA Major Groove," *Bioorganic Chemistry,* 28:324-337 (2000).

Inoue, T., et al., "Fluorescence Property of Oxazole Yellow-linked Oligonucleotide. Triple Helix Formation and Photocleavage of Double-stranded DNA in the Presence of Spermine," *Bioorganic & Medicinal Chemistry,* 7:1207-1211 (1999).

Jackson, L.K., et al., "Altering the Reaction Specificity of Eukaryotic Ornithine Decarboxylase," *Biochemistry,* 39:11247-11257 (2000).

Keppler, M., et al., "DNA Triple Helix Stabilization by a Naphthylquinoline Dimer," *FEBS Letters,* 447:223-226 (1999).

Kisko, J.L. and Barton, J.K., "Recognition of DNA Base Pair Mismatches by a Cyclometalated Rh(III) Intercalator," *Inorg. Chem.,* 39:4942-4949 (2000).

Komiyama, M., et al., "PNA for One-base Differentiating Protection of DNA From Nuclease and its Use of SNPs Detection," *J. Am. Chem. Soc.,* 125(13):3758-3762 (2003).

Lauretti, F., et al., "Use of Acridine Orange Staining for the Detection of Rotavirus RNA in Polyacrylamide Gels," *Journal of Virological Methods,* 114:29-35 (2003).

Ma, D.-L. and Che C.-M., "A Bifunctional Platinum(II) Complex Capable of Intercalation and Hydrogen-Bonding Interactions with DNA: Binding Studies and Cytotoxicity," *Chem. Eur. J.,* 9:6133-6144 (2003).

Mazerski, J. and Muchewicz K., "The Intercalation of Imidazoacridinones into DNA Induces Conformational Changes in Their Side Chain," *Acta Biochimica Polonica,* 47(1):65-78 (2000).

Mueller, S.O. and Stopper H., "Characterization of the Genotoxicity of Anthraquinones in Mammalian Cells," *Biochimica et Biophysica Acta,* 1428:406-414 (1999).

Nguyen, B., et al., "Strong Binding in the DNA Minor Groove by an Aromatic Diamidine with a Shape That Does Not Match the Curvature of the Groove," *J. Am. Chem. Soc.*, 124:13680-13681 (2002).

Nielsen, C.B., et al., "NMR Structure Determination of a Modified DNA Oligonucleotide Containing a New Intercalating Nucleic Acid," *Bioconjugate Chem.*, 15:260-269 (2004).

Norden, B. and Tjerneld, F., "Optical Studies on Complexes Between DNA and Pseudoisocyanine," *Biophysical Chemistry*, 6(1):31-45 (1977).

Önfelt, B., et al., "Cell Studies of the DNA Bis-Intercalator Δ-Δ [μ-C4(cpdppz)$_2$-(phen)$_4$Ru$_2$]$^{4+}$: Toxic Effects and Properties as a Light Emitting DNA Probe in V79 Chinese Hamster Cells," *Mutagenesis*, 17(4):317-320 (2002).

Osiadacz, J., et al., "Sequence-Slectivity of 5,11-Dimethyl-5*H*-indolo[2,3-*b*]quinoline Binding to DNA. Footprinting and Molecular Modeling Studies," *Bioorganic & Medicinal Chemistry*, 8:937-943 (2000).

Patolsky, F., et al., "Amplified DNA Detection by Electrogenerated Biochemiluminescence and by the Catalyzed Precipitation of an Insoluble Product on Electrodes in the Presence of the Doxorubicin Intercalator," *Agnew Chem. Int. Ed.*, 41(18):3398-3402 (2002).

Petersen, M., et al., "LNA: A Versatile Tool for Therapeutics and Genomics," *Trends in Biotechnology*, 21(2):74-81 (2003).

Ray, A. and Norden, B., "Peptide Nucleic Acid (PNA): Its Medical and Biotechnical Applications and Promise for the Future," *The FASEB Journal*, 14:1041-1060 (2000).

Řeha, D., et al., "Intercalators. 1. Nature of Stacking Interactions between Intercalators (Ethidium, Daunomycin, Ellipticine, and 4',6-Diaminide-2-phenylindole) and DNA Base Pairs. *Ab Initio* Quantum Chemical, Density Function Theory, and Empirical Potential Study," *J. Am. Chem. Soc.*, 124:3366-3376 (2002).

Renneberg, D. and Dervan, P.B., "Imidazopyridine/Pyrrole and Hydroxybenzimidazole/Pyrrole Pairs for DNA Minor Groove Recognition," *J. Am. Chem. Soc.*, 125:5707-5716 (2003).

Shim, Y.-H., et al., "Relative DNA Binding Affinity of Helix 3 Homeodomain Analogues, Major Groove Binders, Can be Rapidly Screened by Displacement of Prebound Ethidium Bromide. A Comparative Study," *Org. Biomol. Chem.*, 2:915-921 (2004).

Silverman, A.P., et al., "2.4-Å Crystal Structure of the Asymmetric Platinum Complex {Pt(ammine)(cyclohexylamine)}$^{2+}$ Bound to a Dodecamer DNA Duplex," *The Journal of Biological Chemistry*, 277(51):49743-49749 (2002).

Tanious, F.A., et al., "DNA Sequence Dependent Monomer-Dimer Binding Modulation of Asymmetric Benzimidazole Derivatives," *J. Am. Chem. Soc.*, 126:143-153 (2004).

Tarasov, S.G., et al., "Bisimidazoacridones: 2. Steady-state and Time-resolved Fluorescence Studies of Their Diverse Interactions with DNA," *Photochemistry and Photobiology*, 78(4):313-322 (2003).

Tawar, U., et al., "Minor Groove Binding DNA Ligands with Expanded A/T Sequence Length Recognition, Selective Binding to Bent DNA Regions and Enhanced Fluorescent Properties," *Biochemistry*, 42:13339-13346 (2003).

Tomlinson, A., et al., "A Structural Model for Cyanine Dyes Templated into the Minor Groove of DNA," *Chemical Physics*, 325:36-47 (2006).

Toshima, K., et al., "2-Phenylquinoline-Carbohydrate Hybrids: Molecular Design, Chemical Synthesis, and Evaluation of a New Family of Light-Activatable DNA-Cleaving Agents," *Angew. Chem. Int. Ed.*, 38(24):3733-3735 (1999).

Varadarajan, S., et al., "DNA Damage and Cytotoxicity Induced by Minor Groove Binding Methyl Sulfonate Esters," *Biochemistry*, 42:14318-14327 (2003).

Wakelin, L.P.G., et al., "Bisintercalating Threading Diacridines: Relationships between DNA Binding, Cytotoxicity, and Cell Cycle Arrest," *J. Med. Chem.*, 46:5790-5802 (2003).

Wang, M. and Armitage, B.A., "Colorimetric Detection of PNA-DNA Hybridization Using Cyanine Dyes," *Methods in Molecular Biology*, 208:131-142 (2002).

Wilhelmsson, L.M., et al., "Genetic Screening Using the Colour Change of a PNA-DNA Hybrid-Binding Cyanine Dye," *Nucleic Acids Research*, 30(2):e3(4 pages) (2002).

Wong, M., et al., "Oxazole Yellow Homodimer YOYO-1-labeled DNA: A Fluorescent Complex that can be Used to Assess Structural Changes in DNA Following Information and Cellular Delivery of Cationic Lipid DNA Complexes," *Biochimica et Biophysica Acta*, 1527:61-72 (2001).

Woods, C.R., et al., "Synthesis and DNA Binding Properties of Saturated Distamycin Analogues," *Bioorganic & Medicinal Chemistry Letters*, 12:2647-2650 (2002).

International Search Report for PCT Application No. PCT/US2008/054371.

Tatikolov and Costa, "Photophysics and Photochemistry of Hydrophilic Cyanine Dyes in Normal and Reverse Micelles," *Photochem. Photobiol. Sci.*, 1:211-218 (2002).

International Search Report for PCT Application No. PCT/US07/04814.

Ogul'chansky, T., et al., "Interaction of cyanine dyes with nucleic acids. XVIII. Formation of the carbocyanine dye J-aggregates in nucleic acid grooves," *Spectrochimica Acta Part A*, 57:2705-2715 (2001).

DeAngelis, D., "Why FRET Over Genomics," *Physiol. Genomics*, 1:93-99 (1999).

Roberts, E., et al., "Selective Dequenching by Photobleaching Increases Fluorescence Probe Visibility," *J. of Fluorescence*, 13(6):513-517 (2003).

Letter dated Sep. 3, 2008 from Canadian associate citing references.

\* cited by examiner

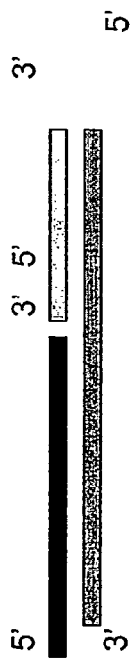
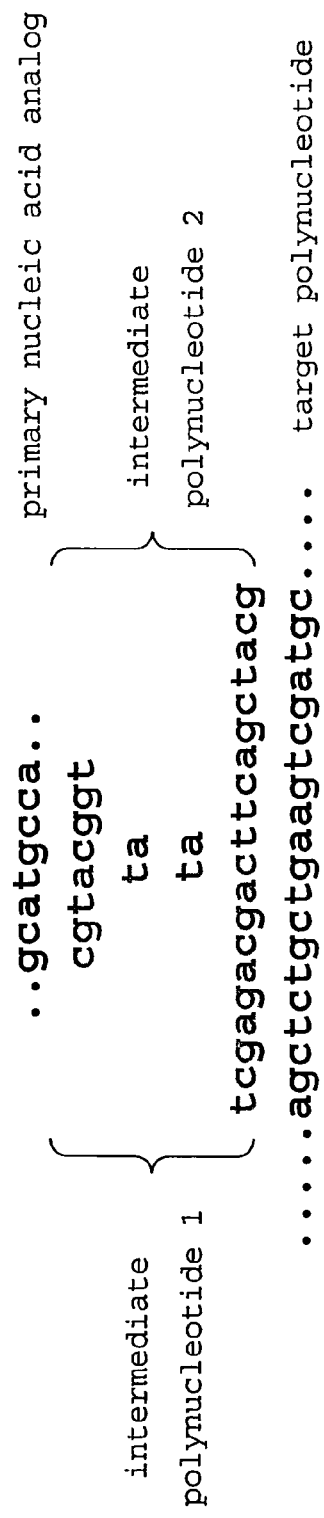
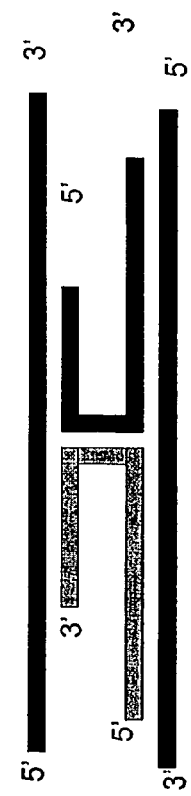
Figure 18A
Figure 18B agctctgctgtgtaaagtcgatgcgtaaagtgcct Target
polynucleotide
tcgagacgacattcagctacg
─────────────────────
nucleic acid  nucleic acid  nucleic acid
analog 1      analog 2      analog 3

Figure 18C agctctgctgtTaagtcgatgcgtaaagtgcct Target
polynucleotide
tcgagac          cagctacg
       → gacattt
nucleic acid  nucleic acid  nucleic acid
analog 1      analog 2      analog 3

Figure 18D

SEQUENCE LISTING

<160> NUMBER OF SEQ ID NOS: 34

<210> SEQ ID NO 1
<211> LENGTH: 19
<212> TYPE: DNA
<213> ORGANISM: Artificial Sequence
<220> FEATURE:
<223> OTHER INFORMATION: PNA for 16S
<220> FEATURE:
<221> NAME/KEY: misc_feature
<222> LOCATION: (19)..(19)
<223> OTHER INFORMATION: Lysine is attached to g

<400> SEQUENCE: 1
cactgctgcc tccccgtag                                                    19

<210> SEQ ID NO 2
<211> LENGTH: 18
<212> TYPE: DNA
<213> ORGANISM: Artificial Sequence
<220> FEATURE:
<223> OTHER INFORMATION: target polynucleotide

<400> SEQUENCE: 2
ctacgggagg cagcagtg                                                     18

<210> SEQ ID NO 3
<211> LENGTH: 22
<212> TYPE: DNA
<213> ORGANISM: Artificial Sequence
<220> FEATURE:
<223> OTHER INFORMATION: nucleic acid analog to detect bacteria

<400> SEQUENCE: 3
gaassmycya acacytagca ct                                                22

<210> SEQ ID NO 4
<211> LENGTH: 24
<212> TYPE: DNA
<213> ORGANISM: Artificial Sequence
<220> FEATURE:
<223> OTHER INFORMATION: nucleic acid analog to detect bacteria

<400> SEQUENCE: 4
tacaamgagy ygcwagacsg ygas                                              24

<210> SEQ ID NO 5
<211> LENGTH: 21
<212> TYPE: DNA
<213> ORGANISM: Artificial Sequence
<220> FEATURE:
<223> OTHER INFORMATION: nucleic acid analog to detect gram positive
      bacteria

<400> SEQUENCE: 5
gcagywaacg cattaagcac t                                                 21

<210> SEQ ID NO 6
<211> LENGTH: 20
<212> TYPE: DNA
<213> ORGANISM: Artificial Sequence
<220> FEATURE:
<223> OTHER INFORMATION: nucleic acid analog to detect gram positive
      bacteria

```
<400> SEQUENCE: 6
acgacacgag ctgacgacaa                                              20

<210> SEQ ID NO 7
<211> LENGTH: 23
<212> TYPE: DNA
<213> ORGANISM: Artificial Sequence
<220> FEATURE:
<223> OTHER INFORMATION: nucleic acid analog to detect gram negative
      bacteria

<400> SEQUENCE: 7
tctagctggt ctgagaggat gac                                          23

<210> SEQ ID NO 8
<211> LENGTH: 21
<212> TYPE: DNA
<213> ORGANISM: Artificial Sequence
<220> FEATURE:
<223> OTHER INFORMATION: nucleic acid analog to detect gram negative
      bacteria

<400> SEQUENCE: 8
gagttagccg gtgcttcttc t                                            21

<210> SEQ ID NO 9
<211> LENGTH: 21
<212> TYPE: DNA
<213> ORGANISM: Artificial Sequence
<220> FEATURE:
<223> OTHER INFORMATION: nucleic acid analog to detect Fungi

<400> SEQUENCE: 9
gagttagccg gtgcttcttc t                                            21

<210> SEQ ID NO 10
<211> LENGTH: 19
<212> TYPE: DNA
<213> ORGANISM: Artificial Sequence
<220> FEATURE:
<223> OTHER INFORMATION: nucleic acid analog to detect Fungi

<400> SEQUENCE: 10
tagcgacggg cggtgtgta                                               19

<210> SEQ ID NO 11
<211> LENGTH: 13
<212> TYPE: DNA
<213> ORGANISM: Artificial Sequence
<220> FEATURE:
<223> OTHER INFORMATION: PNA for cauliflower mosaic virus 35S promoter
<220> FEATURE:
<221> NAME/KEY: misc_feature
<222> LOCATION: (13)..()
<223> OTHER INFORMATION: Lysine is attached to g

<400> SEQUENCE: 11
cccacccacg agg                                                     13

<210> SEQ ID NO 12
<211> LENGTH: 19
<212> TYPE: DNA
<213> ORGANISM: Artificial Sequence
<220> FEATURE:
<223> OTHER INFORMATION: primer
```

```
<400> SEQUENCE: 12
gctcctacaa atgccatca                                                    19

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gatagtggga ttgtgcgtca                                                   20

<210> SEQ ID NO 14
<211> LENGTH: 19
<212> TYPE: DNA
<213> ORGANISM: Artificial Sequence
<220> FEATURE:
<223> OTHER INFORMATION: PNA

<400> SEQUENCE: 14
cccacccacg aggaacatc                                                    19

<210> SEQ ID NO 15
<211> LENGTH: 18
<212> TYPE: RNA
<213> ORGANISM: Artificial Sequence
<220> FEATURE:
<223> OTHER INFORMATION: target RNA sequence

<400> SEQUENCE: 15
cuacgggagg cagcagug                                                     18

<210> SEQ ID NO 16
<211> LENGTH: 18
<212> TYPE: DNA
<213> ORGANISM: Artificial Sequence
<220> FEATURE:
<223> OTHER INFORMATION: PNA for cauliflower mosaic virus 35S promoter

<400> SEQUENCE: 16
gatagtggga ttgtgcgt                                                     18

<210> SEQ ID NO 17
<211> LENGTH: 15
<212> TYPE: DNA
<213> ORGANISM: Artificial Sequence
<220> FEATURE:
<223> OTHER INFORMATION: PNA for cauliflower mosaic virus 35S promoter
<220> FEATURE:
<221> NAME/KEY: misc_feature
<222> LOCATION: (15)..()
<223> OTHER INFORMATION: Lysine is attached to g

<400> SEQUENCE: 17
tcttcttttt ccacg                                                        15

<210> SEQ ID NO 18
<211> LENGTH: 15
<212> TYPE: DNA
<213> ORGANISM: Artificial Sequence
<220> FEATURE:
<223> OTHER INFORMATION: PNA for cauliflower mosaic virus 35S promoter
<220> FEATURE:
<221> NAME/KEY: misc_feature
<222> LOCATION: (15)..()
<223> OTHER INFORMATION: Lysine is attached to g
```

```
<400> SEQUENCE: 18
tcacatcaat ccact                                                    15

<210> SEQ ID NO 19
<211> LENGTH: 17
<212> TYPE: DNA
<213> ORGANISM: Artificial Sequence
<220> FEATURE:
<223> OTHER INFORMATION: PNA for huSRY

<400> SEQUENCE: 19
tgagtgtgtg gctttcg                                                  17

<210> SEQ ID NO 20
<211> LENGTH: 17
<212> TYPE: DNA
<213> ORGANISM: Artificial Sequence
<220> FEATURE:
<223> OTHER INFORMATION: PNA for 16S

<400> SEQUENCE: 20
actgctgcct cccgtag                                                  17

<210> SEQ ID NO 21
<211> LENGTH: 12
<212> TYPE: DNA
<213> ORGANISM: Artificial Sequence
<220> FEATURE:
<223> OTHER INFORMATION: PNA for 16S

<400> SEQUENCE: 21
tgcctcccgt ag                                                       12

<210> SEQ ID NO 22
<211> LENGTH: 11
<212> TYPE: DNA
<213> ORGANISM: Artificial Sequence
<220> FEATURE:
<223> OTHER INFORMATION: PNA for 16S

<400> SEQUENCE: 22
tgcctcccgt a                                                        11

<210> SEQ ID NO 23
<211> LENGTH: 12
<212> TYPE: DNA
<213> ORGANISM: Artificial Sequence
<220> FEATURE:
<223> OTHER INFORMATION: PNA for HIV

<400> SEQUENCE: 23
ctcattgatg gt                                                       12

<210> SEQ ID NO 24
<211> LENGTH: 12
<212> TYPE: DNA
<213> ORGANISM: Artificial Sequence
<220> FEATURE:
<223> OTHER INFORMATION: PNA for HCV

<400> SEQUENCE: 24
cgcagaccac ta                                                       12
```

```
<210> SEQ ID NO 25
<211> LENGTH: 12
<212> TYPE: DNA
<213> ORGANISM: Artificial Sequence
<220> FEATURE:
<223> OTHER INFORMATION: LNA sequence
<220> FEATURE:
<221> NAME/KEY: misc_feature
<222> LOCATION: (3)..(3)
<223> OTHER INFORMATION: methylation site
<220> FEATURE:
<221> NAME/KEY: misc_feature
<222> LOCATION: (4)..(4)
<223> OTHER INFORMATION: methylation site
<220> FEATURE:
<221> NAME/KEY: misc_feature
<222> LOCATION: (6)..(6)
<223> OTHER INFORMATION: methylation site
<220> FEATURE:
<221> NAME/KEY: misc_feature
<222> LOCATION: (7)..(7)
<223> OTHER INFORMATION: methylation site
<220> FEATURE:
<221> NAME/KEY: misc_feature
<222> LOCATION: (8)..(8)
<223> OTHER INFORMATION: methylation site

<400> SEQUENCE: 25
tgcctcccgt ag                                                         12

<210> SEQ ID NO 26
<211> LENGTH: 12
<212> TYPE: DNA
<213> ORGANISM: Artificial Sequence
<220> FEATURE:
<223> OTHER INFORMATION: LNA
<220> FEATURE:
<221> NAME/KEY: misc_feature
<222> LOCATION: (4)..(4)
<223> OTHER INFORMATION: methylation site
<220> FEATURE:
<221> NAME/KEY: misc_feature
<222> LOCATION: (6)..(6)
<223> OTHER INFORMATION: methylation site
<220> FEATURE:
<221> NAME/KEY: misc_feature
<222> LOCATION: (8)..(8)
<223> OTHER INFORMATION: methylation site

<400> SEQUENCE: 26
tgcctcccgt ag                                                         12

<210> SEQ ID NO 27
<211> LENGTH: 12
<212> TYPE: DNA
<213> ORGANISM: Artificial Sequence
<220> FEATURE:
<223> OTHER INFORMATION: LNA
<220> FEATURE:
<221> NAME/KEY: misc_feature
<222> LOCATION: (8)..(8)
<223> OTHER INFORMATION: methylation site

<400> SEQUENCE: 27
tgcctcccgt ag                                                         12

<210> SEQ ID NO 28
<211> LENGTH: 15
<212> TYPE: DNA
<213> ORGANISM: Artificial Sequence
<220> FEATURE:
<223> OTHER INFORMATION: target polynucleotide
```

```
<400> SEQUENCE: 28
agtggattga tgtga                                                    15

<210> SEQ ID NO 29
<211> LENGTH: 12
<212> TYPE: DNA
<213> ORGANISM: Artificial Sequence
<220> FEATURE:
<223> OTHER INFORMATION: primer

<400> SEQUENCE: 29
agaagaacgc ac                                                       12

<210> SEQ ID NO 30
<211> LENGTH: 12
<212> TYPE: DNA
<213> ORGANISM: Artificial Sequence
<220> FEATURE:
<223> OTHER INFORMATION: primer

<400> SEQUENCE: 30
gtgcgttctt ct                                                       12

<210> SEQ ID NO 31
<211> LENGTH: 10
<212> TYPE: DNA
<213> ORGANISM: Artificial Sequence
<220> FEATURE:
<223> OTHER INFORMATION: primer

<400> SEQUENCE: 31
tgtgaacgca                                                          10

<210> SEQ ID NO 32
<211> LENGTH: 10
<212> TYPE: DNA
<213> ORGANISM: Artificial Sequence
<220> FEATURE:
<223> OTHER INFORMATION: primer

<400> SEQUENCE: 32
tgcgttcaca                                                          10

<210> SEQ ID NO 33
<211> LENGTH: 18
<212> TYPE: DNA
<213> ORGANISM: Artificial Sequence
<220> FEATURE:
<223> OTHER INFORMATION: PNA

<400> SEQUENCE: 33
gatagtggga ttgtgcgt                                                 18

<210> SEQ ID NO 34
<211> LENGTH: 15
<212> TYPE: DNA
<213> ORGANISM: Artificial Sequence
<220> FEATURE:
<223> OTHER INFORMATION: PNA
<220> FEATURE:
<221> NAME/KEY: misc_feature
<222> LOCATION: (15)..(15)
<223> OTHER INFORMATION: Lysine is attached to t
```

```
-continued

<400> SEQUENCE: 34
tcacatcaat ccact                                                                  15
```

SYSTEM FOR DETECTING POLYNUCLEOTIDES

RELATED APPLICATIONS

The present application is a continuation in part of International Application No. PCT/US2004/016118, filed May 20, 2004, which claims the benefit of U.S. Provisional Application No. 60/471,827, filed May 20, 2003, each of which is incorporated herein by reference in its entirety.

FIELD OF THE INVENTION

The present invention relates to the field of nucleic acid-based diagnostics. More particularly, the present invention relates to methods, compositions, and assay systems for detecting polynucleotides.

BACKGROUND OF THE INVENTION

There is a great need to identify and quantify polynucleotides. Current methods of identifying target polynucleotides such as those associated with pathogens, pathogen infection, human genes associated with diseases and disorders, genetically modified organisms (GMOs), biowarfare agents, food applications, water applications, environmental applications, veterinary applications, and agricultural applications presently rely on methods such as the polymerase chain reaction (PCR), NASBA, TMA, or bDNA. These methods require skilled personnel and specialized equipment. Accordingly, there is a great need for convenient and economical methods of detection, identification, and quantification of target polynucleotides. This invention meets this and other needs.

SUMMARY OF THE INVENTION

In one aspect, the present invention relates to methods for detecting the presence or amount of a target polynucleotide in a sample. In a further aspect, one method includes the following steps:

A nucleic acid analog that binds a target nucleic acid sequence of the target polynucleotide in a sequence specific manner, and a dye for which the rate of change in an optical property is different in the presence and absence of a target polynucleotide/nucleic acid analog hybrid, are combined to produce a mixture.

In another aspect, a method includes the following steps: peptide nucleic acid (PNA) that binds a target nucleic acid sequence of the target polynucleotide in a sequence specific manner, and a dye for which the rate of change in an optical property is different in the presence and absence of a target polynucleotide/PNA hybrid, are combined to produce a mixture. The rate of change in the optical property of the dye in the mixture is compared to a reference value characteristic of the rate of change in the optical property of the dye in a similar mixture containing a known amount of a target polynucleotide/PNA hybrid to determine a relative rate of change in the optical property. The relative rate of change in the optical property of dye in the mixture is correlated with the presence or amount of the specified target polynucleotide in a sample.

In other aspects, the nucleic acid analog may be a locked nucleic acid (LNA), threose nucleic acid (TNA), or metal linked nucleic acid.

The rate of change in the optical property of the dye may be different in the presence and absence of a target polynucleotide/nucleic acid analog hybrid and when the mixture is provided with a light stimulus, for example.

The sample may include a tissue, collection of cells, cell lysate, purified polynucleotide, or isolated polynucleotide, virus, environmental sample, industrial sample, medical sample, food sample, agricultural sample, veterinary sample, agro-livestock sample, water sample, soil sample, air sample, sample associated with bio-warfare agent, or sample associated with agro-warfare agent. The sample may also include a body part, or a fluid from a body, such as blood, sputum, or semen; among preferable body parts or fluids included in the sample are those associated with forensics studies of crime scenes and the like.

In one aspect, the target polynucleotide may be DNA, preferably DNA obtained directly or indirectly from an organism or a synthetic DNA. In some variations, the target polynucleotide may be obtained from total cellular DNA or a fraction thereof, such as nuclear DNA, mitochondrial DNA, ribosomal DNA, or chloroplast DNA, or viral DNA, or plasmid DNA, or artificial DNA, or epigenomic DNA, or epigenetic DNA, or in vitro amplified DNA, or chimeric DNA.

In another aspect, the target polynucleotide may be RNA, preferably RNA obtained directly or indirectly from an organism or a synthetic RNA. In some variations, the RNA may be total cellular RNA or a fraction thereof, such as ribosomal RNA (rRNA), messenger RNA (mRNA), or transfer RNA (tRNA), or armored RNA, or viral RNA, or micro RNA, or siRNA, or artificial RNA, or chimeric RNA.

The target polynucleotide may be obtained from an organism. In one embodiment, the organism may be a human. In another embodiment, the organism may be a pathogen. In a further embodiment, the target polynucleotide may be from a pathogen, such as a virus, bacterium, or fungus. Non-limiting examples of such viruses or bacteria include *Bacillus anthracis, Clostridium botulinu, Brucellae, Vibrio cholera, Clostridium perfringes,* Ebola virus, *Yersinia pesits, Coxiella burnetii,* Smallpox virus, hepatitis C virus, hepatitis B virus, and human immunodeficiency virus.

The nucleic acid analog may be partially complementary to the target nucleic acid sequence. Alternatively, the nucleic acid analog may be exactly complementary to the target nucleic acid sequence.

The nucleic acid analog may be greater than about 4 nucleic acid bases in length and/or less than about 24 nucleic acid bases in length. Preferably, the nucleic acid analog is about 5 or more nucleic acid bases in length; more preferably, the nucleic acid analog is at least about 7 or more, about 8 or more, about 9 or more, about 10 or more, or about 11 or more nucleic acid bases in length. In a further variation, the nucleic acid analog may also be about 12 nucleic acid bases in length; more preferably, the nucleic acid analog is about 14 nucleic acid bases in length, or about 16, or about 18, or about 20, or about 22 nucleic acid bases in length. Nucleic acid analogs that are in excess of about 24 nucleic acid bases in length are also usefully employed in the context of the present invention. In particular, such larger preferred nucleic acid analogs include, without limitation, those that have about 28, or about 32, or about 36, or about 40 nucleic acid bases in length.

The nucleic acid analog or target polynucleotide may be immobilized on a solid substrate. Immobilization may be via a non-covalent interaction that relies on any of van der Waals, hydrogen bond, or hydrophobic-related forces, such as occurs between biotin and streptavidin. In a further variation, the nucleic acid analog may be covalently linked to a binding agent that is specific for a particular ligand, as in biotin and streptavidin. In still a further variation, the non-covalent interaction may be an antigen/antibody interaction. The nucleic acid analog or target polynucleotide may also be covalently bonded to the solid substrate.

In a further aspect, the dye is a cyanine dye. Examples of cyanine dyes are a 3,3'-diethylthiacarbocyanine iodide (Sigma, Milwaukee), 3,3'-diethylthiadicarbocyanine iodide (Sigma, Milwaukee), and 3,3'-diethylthiatricarbocyanine iodide (Sigma, Milwaukee).

The dye may have a higher rate of change in the optical property in the presence of nucleic acid analog/target polynucleotide hybrid than in the absence of a nucleic acid analog/target polynucleotide hybrid. Alternatively, the dye may have a lower rate of change in the optical property in the presence of nucleic acid analog/target polynucleotide hybrid than in the absence of a nucleic acid analog/target polynucleotide hybrid.

The rate of change in the optical property of the dye may be determined by measuring an optical property of the dye. Examples of such optical properties include color, absorbance, fluorescence, reflectance, or chemiluminescence. The optical property may be determined at one or more times.

In another aspect, the optical property of the dye is measured at multiple times. In a further aspect, the optical property is measured at a single time.

In a further aspect, the invention is directed to a method of detecting an organism in a sample by detecting the presence or amount of a target polynucleotide in the sample wherein the presence or amount of the target polynucleotide identifies the presence or amount of the organism.

In a further aspect, the invention is directed to a method of detecting a class of organisms in a sample by detecting the presence or amount of a target polynucleotide in the sample wherein the presence or amount of the target polynucleotide identifies the presence or amount of the class of organism.

In another aspect, the invention is directed to a method of detecting a strain of an organism in a sample by detecting the presence or amount of a target polynucleotide in the sample, wherein the presence or amount of the target polynucleotide identifies the presence or amount of the strain.

In a further aspect, the invention is directed to a method of detecting a genetically modified organism (GMO) in a sample by detecting the presence or amount of a target polynucleotide in the sample, wherein the presence or amount of the target polynucleotide identifies the presence or amount of the genetically modified organism.

The present invention is also directed to a method of detecting the presence of a disease state in a subject by detecting the presence or amount of a target polynucleotide, wherein the presence or amount of the target polynucleotide identifies the disease state.

The present invention is also directed to a method of detecting the presence of genetic variation in a subject by detecting the presence or amount of a target polynucleotide, wherein the presence or amount of the target polynucleotide identifies the genetic variation.

In another aspect, the present invention is directed to detecting infection of a host by a pathogen, where the presence or amount of a target polynucleotide, wherein the target nucleic acid is a ribonucleic acid (RNA), and wherein the presence or amount of the target polynucleotide identifies infection of the host by the pathogen.

In another aspect, the invention is directed to a method of detecting a single nucleotide polymorphism (SNP) in a sample by detecting the presence or amount of a target polynucleotide in the sample, wherein the presence or amount of the target polynucleotide identifies the presence or amount of the SNP.

In another aspect, the invention is directed to a method of detecting a genetic sequence or control sequence (that has been added) in a sample by detecting the presence or amount of a target polynucleotide in the sample, wherein the presence or amount of the target polynucleotide identifies the presence or amount of the genetic sequence.

In another aspect, the invention is directed to a method of detecting an in vitro amplified sequence in a sample by detecting the presence or amount of a target polynucleotide in the sample, wherein the presence or amount of the target polynucleotide identifies the presence or amount of the in vitro amplified sequence.

In another aspect, the invention is directed to a method of detecting base pair changes in a sample by detecting the presence or amount of a target polynucleotide in the sample, wherein the presence or amount of the target polynucleotide identifies the presence or amount of the base pair changes.

The invention is also directed to a method of detecting a target polynucleotide in two or more samples by detecting the target polynucleotide in a first sample at a first site of a multi-site device using a first nucleic acid analog molecule, and detecting the target polynucleotide in a second sample at a second site of a multi-site device using a second nucleic acid analog molecule. In one variation, the nucleic acid analog molecules are immobilized on a solid substrate. The method includes detecting two or more target polynucleotide sequences in two or more samples. Alternatively, the samples may be immobilized on a solid substrate.

The present invention is also directed to kits for detecting a target polynucleotide. The kit may include one or more of a sample that includes a target polynucleotide, one or more nucleic acid analogs at least partially complementary to a target nucleic acid sequence of the target polynucleotide, and one or more dyes. Optionally, the kit may include a source of stimulus. Optionally, the kit may include filters for a light source. The kit may include instructions for using the kit. The sample included with the kit is preferably a sample that includes a known amount of a target polynucleotide that can be employed as a standard and for determining a relative rate of change of a mixture, as further characterized herein.

BRIEF DESCRIPTION OF THE DRAWINGS

FIGS. 18A-D depict different schemes for introducing polynucleotide/nucleic acid analog hybrids.

DETAILED DESCRIPTION OF THE INVENTION

Figure 1:
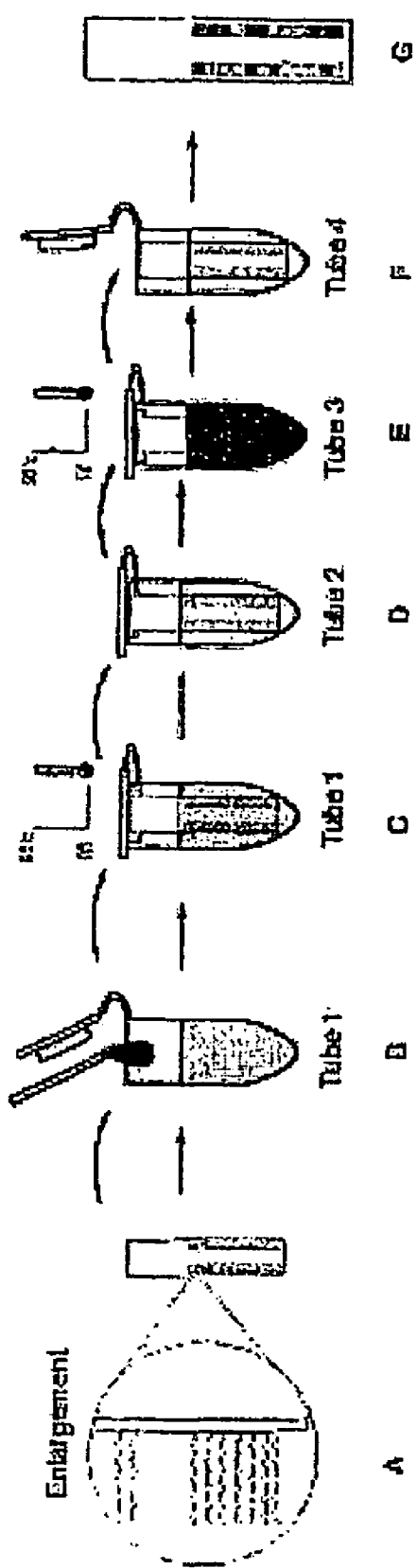
FIG. 1 depicts a schematic of a version of the assay system using a PNA.

The present invention provides methods, compositions and assay systems for detecting a polynucleotide having a target nucleic acid sequence using nucleic acid analogs.

I. General Techniques

The practice of the present invention employs, unless otherwise indicated, conventional techniques of molecular biology (including recombinant techniques), microbiology, cell biology, biochemistry, immunology, protein kinetics, and mass spectroscopy, which are within the skill of the art. Such techniques are explained fully in the literature, such as, SAMBROOK ET AL., MOLECULAR CLONING: A LABORATORY MANUAL (3d ed., Cold Spring Harbor Press 2000); SAMBROOK ET AL., MOLECULAR CLONING: A LABORATORY MANUAL (3d ed., Cold Spring Harbor Press 1989); OLIGONUCLEOTIDE SYNTHESIS (M. J. Gait, ed., 1984); METHODS IN MOLECULAR BIOLOGY (a series of volumes directed at molecular biology protocols that is published by Humana Press, Totowa, N.J.); CELL BIOLOGY: A LABORATORY NOTEBOOK (J. E. Cellis, ed., Academic Press 1998); ANIMAL CELL CULTURE (R. I. Freshney, ed., 1987); J. P. MATHER AND P. E. ROBERTS, INTRODUCTION TO CELL AND TISSUE CULTURE (Plenum Press 1998); CELL AND TISSUE CULTURE: LABORATORY PROCEDURES (A. Doyle, J. B. Griffiths, and D. G. Newell, eds., J. Wiley and Sons 1993-8); METHODS IN ENZYMOLOGY (a series of volumes directed at enzymology protocols that is published by Academic Press, Inc.); HANDBOOK OF EXPERIMENTAL IMMUNOLOGY (D. M. Weir and C. C. Blackwell, eds.); GENE TRANSFER VECTORS FOR MAMMALIAN CELLS (J. M. Miller and M. P. Calos, eds., 1987); CURRENT PROTOCOLS IN MOLECULAR BIOLOGY (F. M. Ausubel et al., eds., 1987 including supplements through May 1, 2004); PCR: THE POLYMERASE CHAIN REACTION (Mullis et al., eds., 1994); CURRENT PROTOCOLS IN IMMUNOLOGY (J. E. Coligan et al., eds., 1991); and SHORT PROTOCOLS IN MOLECULAR BIOLOGY (F. M. Ausubel et al., eds., Wiley and Sons, 1999); all of which are respectively incorporated herein by reference in their entireties. Furthermore, procedures employing commercially available assay kits and reagents typically are used according to manufacturer-defined protocols unless otherwise noted.

II. Definitions

The term "target nucleic acid sequence" generally refers to a nucleic acid sequence detected using the methods, compositions and assay systems of the invention. All or part of the target nucleic acid sequence may bind with a nucleic acid analog molecule by sequence-specific hybridization. The target nucleic acid sequence may be of any length, but is typically less than about 1 Kb in length, less than about 500 bases in length, less than about 24 bases in length, or less than about 12 bases in length. In a further embodiment, the target nucleic acid sequence can be about 10, about 12, about 14, or about 18 bases in length. In other embodiments, the target nucleic acid can be at least about 4, at least about 5, at least about 6, at least about 7, at least about 8, at least about 9, at least about 10, at least about 12, at least about 14, at least about 15, at least about 18, at least about 20, at least about 25, at least about 30, at least about 35, at least about 40, at least about 45, or at least about 50 bases in length. The target nucleic acid sequence of the invention may include protein coding sequence and/or non-coding sequences (e.g., regulatory sequences, introns, etc).

The term "polynucleotide" refers to a polymeric form of nucleotides of any length, either deoxyribonucleotides or ribonucleotides, or analogs thereof. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, nucleic acid probes, primers, and amplified DNA. A polynucleotide may contain modified nucleotides, such as methylated nucleotides and nucleotide analogs. The sequence of nucleotides may be interrupted by non-nucleotide components. A polynucleotide may be further modified before or after polymerization, such as by conjugation with a labeling component. The polynucleotide may be an amplified region of a longer polynucleotide.

The term "target polynucleotide" refers to a polynucleotide that includes a target nucleic acid sequence.

The term "nucleic acid analog" includes any nucleic acid analog having one or more bases that differ from guanine, thymidine, adenosine, cytosine, or uracil, and/or having one or more differences in a phosphoribose of an RNA backbone or phosphodeoxyribose of a DNA backbone. "Nucleic acid analogs" include, but are not limited to, peptide nucleic acids (PNAs), locked nucleic acids (LNA), such as those disclosed in TRENDS IN BIOTECHNOLOGY 21:74-81 (2003), metal-linked nucleic acids, modified polynucleotides such as anthraquinone-modified (as disclosed in Yamana et al., NUCLEIC ACIDS RES. SUPPL. 2003:89-90 (2003), threose nucleic acids (TNAs), such as those disclosed in Chaput et al., J. AMER. CHEM. SOC., 125, 856-857 (2003), and chimeric nucleic acids.

Figure 2:
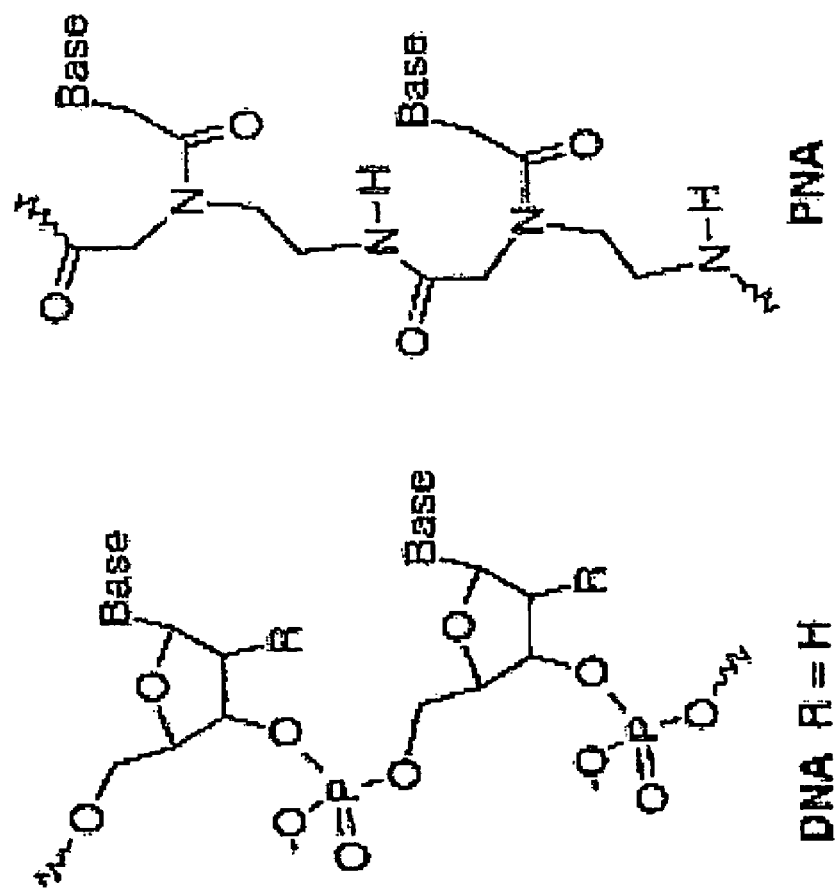
FIG. 2 shows the structural difference between a DNA molecule and a sample PNA molecule.

The term "peptide nucleic acid," or "PNA," includes any nucleic acid analog in which the deoxyribose phosphate backbone of a nucleic acid has been replaced by a synthetic peptide-like backbone, including, for example, N-(2-aminoethyl)-glycine units, such as, without limitation, that depicted in FIG. 2 hereof (also, see Nielsen et al., Science 254:1497-500 (1991), and those disclosed in U.S. Pat. Nos. 5,786,461, 6,357,163, 6,107,470, 5,773,571, 6,441,130, 6,451,968, 6,228,982, 5,641,625, 5,766,855, 5,736,336, 5,719,262, 5,714,331, 5,719,262, and 6,414,112. The purine and pyrimidine bases may be attached by any covalent linkage, including, for example, methylene carbonyl linkages. As used herein, PNA molecules can have additional atoms between the PNA backbone and nucleobase. These analogs include, for example, D-lysine chains, cyclic structures such as cyclopentane or pyrrolidine rings, and/or chiral substitutents, including PNA molecules described in U.S. Pat. No. 6,403,763, U.S. Patent Application 2003/0162699, and U.S. Patent Application 2003/0157500. The PNA backbone may include substitutions or extensions in the peptide backbone. PNAs may include peptide-based nucleic acid mimics (PENAMS), such as those disclosed, for example, in U.S. Pat. No. 5,705,333, atoms having unusual chiral centers, such as D-chiral centers and quasi-chiral centers, and atom substitutions in the PNA backbone.

The terms "nucleic acid analog/polynucleotide hybrid" and "polynucleotide/nucleic acid analog hybrid" are synonymous and refer to a nucleic acid analog and polynucleotide hybridized in a sequence-specific manner.

The terms "PNA/polynucleotide hybrid" and "polynucleotide/PNA hybrid" are synonymous and refer to a PNA and polynucleotide hybridized in a sequence-specific manner.

By "complementary" it is meant that the single-stranded nucleic acid analog molecule has the ability to bind polynucleotides in a base-specific manner. The nucleic acid analog molecule may be synthesized to bind a target polynucleotide, such as a full-length polynucleotide strand or a part thereof. A nucleic acid analog molecule that is "complementary" may have one or more single base pair mismatches, additions, and/or deletions, but is still capable of binding the target polynucleotide under the selected hybridization conditions. In one embodiment, complementary sequences may hybridize through Watson-Crick (A-T or A-U and C-G). In a further embodiment, complementary sequences may hybridize through Hoogstein base pairing between the nucleic acid analog and polynucleotide nucleobases.

By "exactly complementary" it is meant that the single-stranded nucleic acid analog molecule has the ability to bind a target nucleic acid sequence and contains no mis-matches. A nucleic acid analog molecule is not exactly complementary to a target polynucleotide if there is a single base-pair mismatch between the nucleic acid analog and the target polynucleotide.

The term "rate" refers to a change (e.g., of a property of a composition or compound). A rate may be described in terms of a specific rate constant. A rate may be determined by making measurements over a period of time. A rate may be described by making measurements, determined by measurements at two different time points in a process (e.g., before and after a specific stimulus, addition of a component, etc.), or by making measurements at least three, at least four, or at least five, timepoints. A rate may be expressed in quantitative or qualitative terms (e.g. a change is "fast" or "slow"). A rate may be determined by comparing a property or compound to a reference value, or by other methods.

As used herein, the term "relative rate" refers to the rate of one process compared to the rate of another process. A "relative rate" may be approximate (e.g. the rate of one process may be "faster" or "slower" than the rate of another process) or qualitative (e.g. comparing measured rate constants of two processes).

As used herein, the term "dye" refers to a compound that has a measurable optical property or that may be converted to a compound with a measurable optical property. Measurable optical properties include, but are not limited to color, absorbance, fluorescence, reflectance, and chemiluminescence. The dye may exhibit the optical property under certain conditions, such as binding a polynucleotide/nucleic acid analog hybrid, or failing to bind a polynucleotide/nucleic acid analog hybrid.

"Armored RNA™" refers to an RNA that is ribonuclease resistant due to the encapsidation of the RNA by bacteriophage proteins. "Armored RNA™" is further described, for example, in U.S. Pat. Nos. 6,399,307, 6,214,982, 5,939,262, 5,919,625, and 5,677,124.

"Non-specific carrier polynucleotide" as used herein refers to non-target polynucleotide molecules that increase the binding affinity of nucleic acid analogs with specific target polynucleotides and/or enhances the sensitivity of assay system.

As used herein, the term "nucleic acid analog binding site" refers to the point of attachment of one or more nucleic acid analog molecules to a solid support.

As used herein, the term "PNA binding site" refers to the point of attachment of one or more PNA molecules to a solid support.

"Sample" refers to a liquid sample of any type (e.g. blood, serum, water, or urine), and/or a solid sample of any type (e.g. cells, food, water, air, dirt, or grain), and/or an airborne sample of any type.

The term "subject" refers to a multicellular organism, such as an animal, such as a vertebrate, preferably a mammal. A particularly preferred subject addressed in the context of the present invention is a human. Another preferred subject is a plant, inclusive of monocots and dicots.

The term "pathogen" refers to any agent causing a disease, disorder and/or pathological condition and/or symptoms. By way of example, the pathogen may be an organism (or its associated toxin) found in nature, or created in a laboratory, that causes disease in or development of a pathological condition or symptom in, incapacitates, debilitates and/or kills an organism. Pathogens include, but are not limited to, virus, bacteria, fungi, protozoa, eukaryotes, and/or prokaryotes, as well as biological weapons agents, infectious diseases, water borne pathogens, and food pathogens.

The term "biological weapons agent" refers to any organism (or its associated toxin) found in nature or created in the laboratory that is used for the primary purpose of causing disease in, incapacitating, or killing another living organism. Examples of biological weapons agents include, but are not limited to, pathogenic bacteria, fungi, protozoa, rickettsiae, and viruses.

As used herein, the term "infection" refers to the presence of a pathogen in a host. The infection may be dormant or virulent. In one embodiment, the presence of the pathogen is indicated by an alteration in host polynucleotide and/or polypeptide expression. Infection may occur through such routes including, but not limited to, airborne droplets, direct contact, animal or insect vectors, and contaminated food or drink.

As used herein, the term "host response polynucleotide" refers to a polynucleotide that is altered, or a polynucleotide for which the expression is altered, in a host in response to a stimulus, such as infection, and/or contact by a pathogen.

The term "host" as used herein refers to animals and plants. The animal may be a mammal. Examples of mammals include humans, non-human primates, farm animals, sport animals, mice, and rats. Examples of plants include, but are not limited to, agricultural crops.

III. Methods of Detecting Polynucleotides

The present application provides methods, compositions and assay systems for detecting a polynucleotide having a target nucleic acid sequence using nucleic acid analogs. In one embodiment, (i) a sample that contains or may contain, is believed to contain, or is expected not to contain a target polynucleotide, (ii) a nucleic acid analog that binds a target nucleic acid sequence of the polynucleotide in a sequence-specific manner, and (iii) a dye for which the rate of change in an optical property is different in the presence and absence of a polynucleotide/nucleic acid analog hybrid or whose optical property is affected by the content and/or conditions of the present invention, are combined to produce a mixture. The mixture may further include a non-specific carrier polynucleotide such as, but not limited to, non-specific plant DNA, yeast DNA, salmon sperm DNA or TRNA. The rate of change in the optical property of the dye in the mixture is compared to a reference value characteristic of the rate of change in the optical property of the dye in a similar mixture containing a known amount (including a zero amount) of a polynucleotide/nucleic acid analog hybrid to determine a relative rate of change in the optical property. In an alternative method for understanding a result when using this embodiment, the optical property of the mixture once fully constituted is compared before and after the exposure of the mixture to a stimulus means, as further described below. The relative rate of change in the optical property of dye in the mixture or the change in the optical property before and after (or the mixture's optical property after) exposure to the stimulus means is correlated with the presence or amount of the target polynucleotide in a sample to determine the presence or amount of target polynucleotide in the sample wherein the amount of target polynucleotide may be an approximate amount.

In one aspect, the present application provides methods, compositions and assay systems for detecting a polynucleotide having a target nucleic acid sequence using peptide nucleic acid (PNA) molecules. In one embodiment, (i) a sample that may contain or contains, is believed to contain, or is expected not to contain a target polynucleotide, (ii) a peptide nucleic acid (PNA) that binds a target nucleic acid sequence of the polynucleotide in a sequence specific manner, and (iii) a dye for which the rate of change in an optical property is different in the presence and absence of a polynucleotide/PNA hybrid or whose optical property is affected by the content and/or conditions of the present invention are combined to produce a mixture. The mixture may further include a non-specific carrier polynucleotide such as, but not limited to, non-specific plant DNA, yeast DNA, salmon sperm DNA or tRNA. The rate of change in the optical property of the dye in the mixture is compared to a reference value characteristic of the rate of change in the optical property of the dye in a similar mixture containing a known amount (including a zero amount) of a polynucleotide/PNA hybrid to determine a relative rate of change in the optical property. In an alternative method for understanding a result when using this embodiment, the optical property of the mixture once fully constituted is compared before and after the exposure of the mixture to a stimulus means, as further described below. The relative rate of change in the optical property of dye in the mixture or the change in the optical property before and after exposure to the stimulus means is correlated with the presence or amount of the specified polynucleotide in a sample to determine the presence or amount of target polynucleotide in the sample, wherein the amount of polynucleotide may be an approximate amount.

A reference value can be a value characteristic of a property of a composition or compound having a known characteristic. For example, in various embodiments, a reference value can be determined using a mixture that does not contain a polynucleotide/nucleic acid hybrid; contains some amount (e.g., a known amount) of a polynucleotide/nucleic acid hybrid; contains a zero amount of a polynucleotide/nucleic acid hybrid; or is a reaction mixture from which one or more components (e.g., a nucleic acid analog, a target polynucleotide, or a dye) has been omitted. Further nonlimiting examples of reference values include a value characteristic of an optical property of a mixture that has not been exposed to light stimulus, or, in an alternative embodiment, an optical property of a mixture that has been exposed to light stimulus. The aforementioned examples are for illustration and are not intended to limit the invention, and other examples will be apparent to the practitioner guided by this disclosure. It will be appreciated that a reference value may be, but need not necessarily be, empirically determined (for example, if it is known that the optical properties of composition containing a dye do not change, or change minimally, in the absence of target polynucleotide/nucleic acid analog hybrid, the reference value may be calculated or inferred and not measured). The reference value may be a constant. Although in some cases it may be convenient to assay a "control" sample concurrently with test samples, it is not necessary to do so. A reference value can be determined at one time point, and the value recorded to comparison at later time points. It will be understood that the aforementioned examples are for illustration and not limitation. A variety of reference values are described throughout the specification.

In one aspect, the reference value is characteristic of the rate of change in the optical property of the dye in a similar mixture containing no polynucleotide/nucleic acid analog hybrid. In one embodiment, the reference value may be characterized by the optical property of the dye prior to the combination of all the components in the mixture. In another embodiment, the reference value may be a standard value. For embodiments in which the mixture is exposed to light stimulus, the reference value may be characteristic of the optical property of the dye prior to applying light stimulus. It will be clearly understood that the reference value need not be determined simultaneously with the optical property of the dye in the sample, nucleic acid analog, and dye mixture. In addition it is understood that the reference value may a constant.

Figure 4:
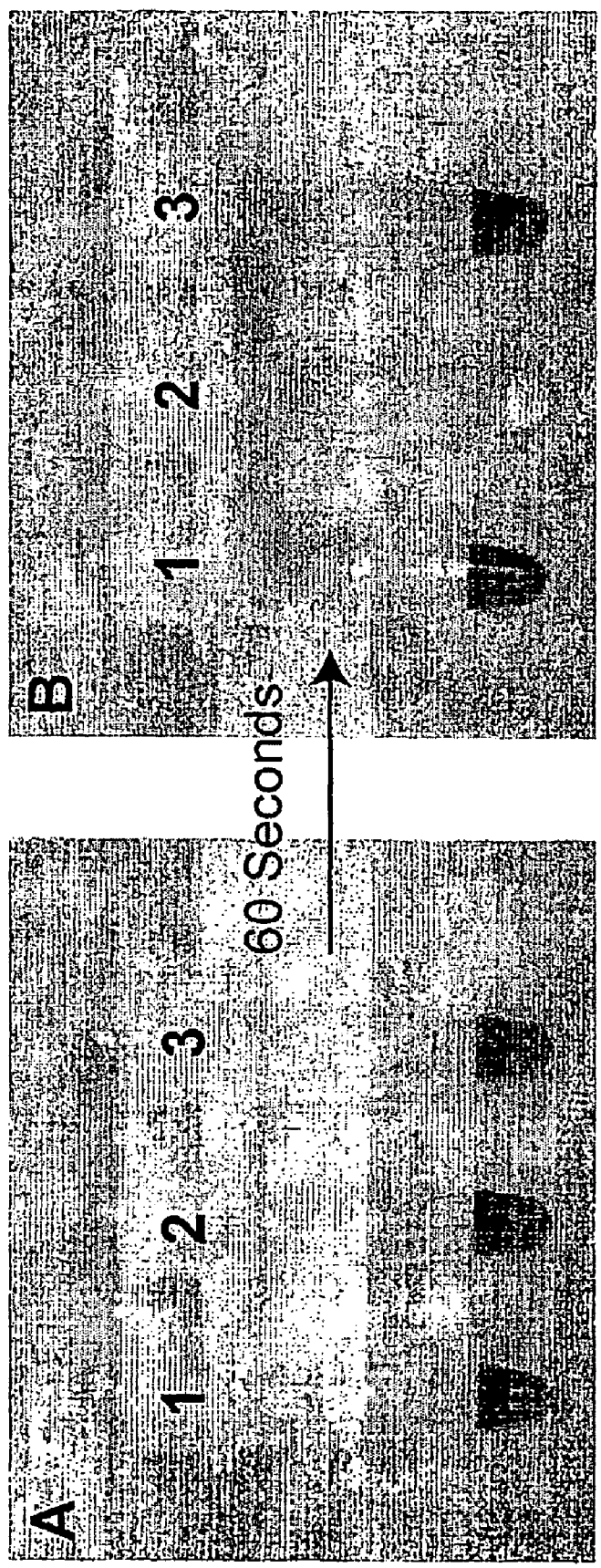
FIG. 4 depicts a light activated assay reaction.

Reference to a specific example will assist in the understanding of the invention. A liquid-based version of this method using PNA is illustrated in Example 1 and FIG. 4. Ten µM of a PNA molecule complementary to the cauliflower mosaic virus 35S promoter ("35S PNA"), and 1 µM 35S promoter DNA (35S DNA) were mixed in a microfuge tube and 150 µM dye was added. The tube was exposed to a light stimulus and over the course of 1 minute the color change was observed (FIG. 4); a change in the optical property of the dye. In the control tubes, the target polynucleotide was absent and the color remained pink even after 24 hours (without light stimulus), indicating a very slow rate of change in the optical property. Little change in an optical property (in this case color change) is observed in the tubes where the 35S PNA is either absent (Tube 3) or does not have a specific target (Tube 1).

A further example using a PNA probe is illustrated in FIG. 1. A) A membrane strip with discrete addresses of PNA sequences complementary to one or more target polynucleotide sequence is placed in the lysis/hybridization tube 1. B) A sample is added to the lysis/hybridization buffer and the mixture is heated to 95° C. for 3 minutes and C) cooled to room temperature. D) The strip is transferred to a fresh tube (tube 2), which contains washing buffer for incubation. Unbound DNA, RNA, and other cellular debris are removed. E) The strip is transferred to a fresh tube (tube 3) containing the detection dye and allowed to incubate for approximately 1 minute. F) The strip is briefly washed in washing buffer (tube 4) to remove residual unbound dye. G) Based on the pattern of hybridization the presence of specific target polynucleotides can be determined by the change of an optical property. The change of an optical property may include, for example, alteration, breakdown or conversion of the dye. By a comparison with a card of known patterns the presence and identity of the substance can be determined.

Figure 22:
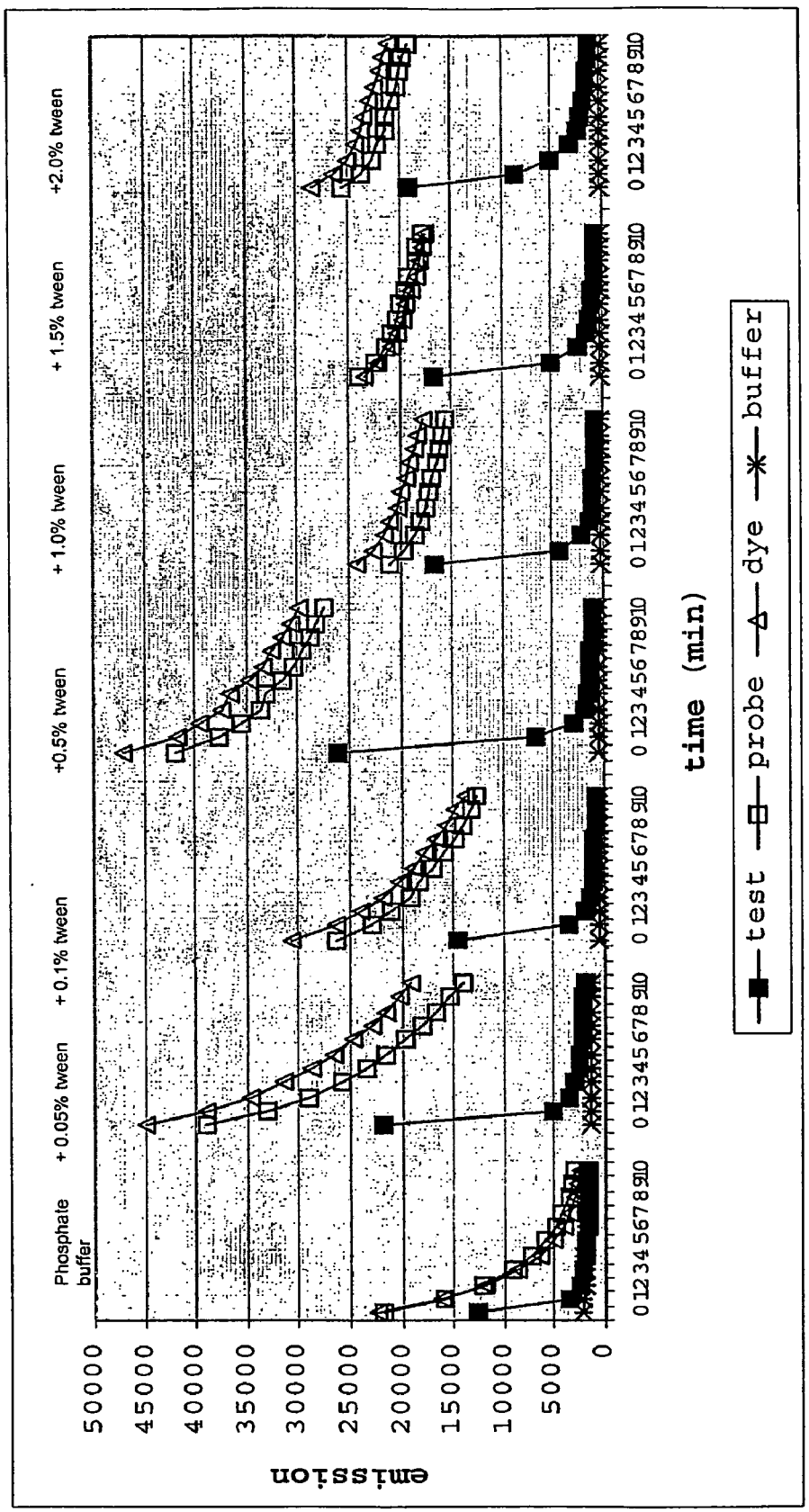
FIG. 22 depicts the effect of different concentrations of TWEEN® 20.

A further example is illustrated in FIG. 22. Ten μM of a PNA molecule complementary to a target nucleic acid sequence and 1 μM target polynucleotide were mixed in a microfuge tube. Two μM of dye and various amounts of a detergent (namely, TWEEN® 20; purchased from Sigma-Aldrich Corporation, St. Louis, Mo.) were added. The tubes were exposed to a light stimulus and over the course of 10 minutes the change in optical properties was observed (FIG. 22). When greater than 1.0% TWEEN® 20 is present, less of a change in the optical property is observed for samples containing dye or probe as compared to the sample containing the target polynucleotide/nucleic acid analog hybrid. When the sample containing the target polynucleotide/nucleic acid hybrid is exposed to light stimulus, the fluorescence (or other optical property) of the dye changes. The presence or amount of a target polynucleotide is detected by observing the change in the fluorescence (or other optical property). It will be appreciated that the presence or amount of target polynucleotide can be accomplished by a single measurement. The amount of target polynucleotide may be an approximate amount.

In a further embodiment, a plurality of nucleic acid analog sequence can be combined in the mixture to detect a plurality of target polynucleotides by multiplexing. Multiplex reactions involving known nucleic acid assay systems may be found at, for example, U.S. Pat. No. 5,582,989.

Without intending to be bound to a particular mechanism or theory, in one aspect the nucleic acid analog/polynucleotide hybrid may mediate a reaction involving the dye, for example, a chemical reaction. Mediating a reaction includes, for example, accelerating, such as in the presence of a catalyst, or decelerating, such as under reduced temperature. In one aspect the nucleic acid analog/polynucleotide hybrid may catalyze a chemical reaction involving the dye. The dye binds to the minor groove of the nucleic acid analog/polynucleotide hybrids, which acts as a catalytic site. Application of a light stimulus adds energy to the mixture and causes a change in the optical property of the dye in the nucleic acid analog/polynucleotide hybrid at a faster rate than in the absence of a nucleic acid analog/polynucleotide hybrid. 3,3'-diethylthiacarbocyanine iodide, for example, turns clear on application of a light stimulus. The higher rate of change in an optical property of the dye corresponds to an increased presence of target polynucleotide in the sample.

Without intending to be bound to a particular mechanism or theory, one theory by which a change in a property of a mixture comprising the sample, polynucleotide, nucleic acid analog and dye may occur is via a chemical reaction that alters the dye. The resultant change in the property of the mixture may be observed as a decrease in a property of the mixture as the dye is converted to a different chemical entity. Alternatively, the resultant change may be observed as an increase in a property. In the context of such a chemical reaction, there may be other properties of the mixture that indicate such a chemical reaction has occurred. Indicators include, for example, a change in the pH of the mixture, the detection of a new chemical entity, or a fragment thereof, a change in a secondary reaction, the formation of a precipitate, the dissolution of a precipitate, a change in conductivity, ionic strength, dipole moment, viscosity, temperature, or transparency of the mixture. One skilled in the art can look towards inherent properties of a given mixture and/or such a chemical reaction that takes place in the context of the mixture for identifying one of these or other properties by which to measure a change that is then correlated to the detection of a target entity.

The following sections describe aspects of the invention in further detail.

A. Designing Nucleic Acid Analog Sequences

For use in the present invention, nucleic acid analogs may be designed to be complementary, but possibly including some mismatched bases, or exactly complementary to a nucleic acid sequence in a target polynucleotide. In one embodiment, the nucleic acid analog is greater than about 4 nucleotides in length and less than about 24 nucleic acid bases in length excluding linkers, amino acids and labels. In other embodiments, the nucleic acid analog may be from about 5 to about 100, from about 8 to about 60, or from about 10 to about 25 nucleic acid bases in length. In another embodiment, the nucleic acid analog may be about 6, about 8, about 10, about 12, about 14, or about 18 nucleic acid bases in length, excluding linkers, amino acids and labels. In other embodiments, the target nucleic acid can be at least 4, at least 5, at least 6, at least 7, at least 8, at least 9, at least 10, at least 12, at least 14, at least 15, at least 18, at least 20, at least 25, at least 30, at least 35, at least 40, at least 45, or at least 50 bases in length. Nucleic acid analogs may be designed to have a portion that is non-complementary to the target polynucleotide, such as a sequence that hangs off the end of the polynucleotide.

The sequence of the nucleic acid analog molecules may be designed in a variety of ways. By way of example, and not limitation, the nucleic acid analog molecules may be designed to have sequences based on known primers used for PCR-based amplification and detection of specific target sequences. The nucleic acid analog molecule may also be designed to be complementary or exactly complementary to any target nucleic acid sequence of the polynucleotide. By way of example, the sequence of the nucleic acid analog molecule may be based on the sequence of PCR primers used to detect polynucleotides associated with pathogens, the presence of a pathogen in a host, a disease gene, or genetic condition. The nucleic acid analog molecule may also be complementary or exactly complementary to all or part of the sequence encoding the active or functional domains of a protein or the intact protein and or non-coding sequences (e.g., regulatory sequences, introns, etc.).

In one embodiment, nucleic acid analogs can be used to distinguish between polynucleotides having an exactly complementary sequence and one with a single base mismatch. For example and without limitation, nucleic acid analogs for use in the invention may be designed to detect single nucleotide polymorphisms (SNPs). Nucleic acid analog/polynucleotide hybridization is affected by base mismatches. According to the methods of the invention, upon the addition of a dye, a single base mismatch between a target sequence (e.g., a SNP) and a nucleic acid analog results in a different rate of change in optical property of the dye compared to a nucleic acid analog that does not have the mismatch. The identification of SNPs for diagnosis and other methods is well known in the art.

In another embodiment, the nucleic acid analog may be designed to detect the presence or amount of a class of organisms. By class of organisms, it is meant that all organisms have one or more sequences that are complementary to, or exactly complementary to, a nucleic acid analog sequence. Such classes of organisms can be distinguished from other organisms based on the complementarity to nucleic acid sequences.

In another embodiment, the nucleic acid analog molecule has a purine content of less than about 60%, including a maximum of 4 purine bases or three guanine bases in a row. Purine-rich nucleic acid analog molecules tend to aggregate and have low solubility in aqueous solutions. The nucleic acid analog molecules are selected to preferably minimize or avoid self-complementary sequences with inverse repeats, hairpins and palindromes since these types of probes are prone to aggregate.

Nucleic acid analog molecules may hybridize to polynucleotides in either orientation, but an anti-parallel orientation is preferred. Anti-parallel is the preferred configuration for antisense and DNA probe-type applications. When the orientation of the nucleic acid analog is anti-parallel, the N-terminal of the nucleic acid analog probe is equivalent to the 5'-end of the DNA. Both N' and 5' are used herein.

One of skill in the art, guided by this disclosure, will recognize that in addition to nucleic acid analogs specifically listed herein, other nucleic acid analogs (including nucleic acid analogs discovered or developed in the future) may be used in the methods of the invention. Nucleic acid analogs that form a polynucleotide/nucleic acid analog hybrid under the assay conditions described herein are suitable for the present methods, and affect the rate of change in an optical property.

Nucleic acid analogs suitable for use in the methods can be identified using any of a variety of screening methods. In one method, for example and not limitation, a sample containing a candidate nucleic acid analog, optionally at varying concentrations, is combined with a polynucleotide having a complementary sequence under conditions under which a nucleic acid analog/polynucleotide hybrid is formed. In an embodiment, a dye is then added. The rate of change in optical property of the dye is then determined. This rate is compared to a reference value characteristic of the rate of change in optical property of the dye in the absence of a nucleic acid analog/polynucleotide hybrid. In a further embodiment, the reference value is characteristic of the absence of polynucleotide. In a still further embodiment, the reference value is characteristic of the presence of target polynucleotide (single stranded or double stranded). It will be recognized that the order of addition is not critical and components can be added in other orders.

In another embodiment, the reference value is characteristic of a non-zero concentration of polynucleotide. In this embodiment, nucleic acid analogs/polynucleotide hybrids result in a different rate of change in optical property over time compared to a reference value (e.g., the presence of double-stranded polynucleotide but absence of nucleic acid analog/polynucleotide hybrid) are selected for use in the claimed methods. The relative rate of change in the optical property is correlated with the presence or amount of specific polynucleotide.

B. Peptide Nucleic Acids (PNAs)

In one aspect, the nucleic acid analogs are PNAs. The PNA hybridizes to all or part of a target nucleic acid sequence in a target polynucleotide by sequence specific hybridization. Alternatively, the conditions may be varied such that a single base pair change can be distinguished.

PNA molecules can hybridize rapidly to target polynucleotides. PNA hybridization to polynucleotides is independent of salt concentration (Demidov et al., BIOCHEM. PHARMACOL. 48:1310-3 (1994)). PNAs are resistant to nuclease and protease attack, and bind to polynucleotides more specifically than conventional DNA probes. Short probes can be used with great sequence specificity (Ray and Norden, FASEB J. 14:1041-60 (2000)). Furthermore, PNA/polynucleotide hybrids have higher thermal stability than the corresponding DNA/polynucleotide hybrids, and the melting point of PNA/polynucleotide hybrids is relatively insensitive to ionic strength, showing equal thermal stability under low (<10 mM NaCl) and moderate (500 mM NaCl) salt concentrations. This ability of PNA/polynucleotide hybrids to form under low salt conditions is significant because the internal structure of dsRNA and rRNA is significantly destabilized at salt concentrations below 200 mM. Therefore, assay conditions can be chosen that favor the disruption of the target nucleic acid while still promoting strong hybridization of PNA molecules (Stefano and Hyldig-Nielsen, *Diagnostic Applications of PNA oligomers*, in DIAGNOSTIC GENE DETECTION AND QUANTIFICATION TECHNOLOGIES 19-39 (Minden ed., 1997). PNA/polynucleotide hybridization is severely affected by base mismatches and PNA molecules can maintain sequence discrimination up to the level of a single mismatch.

PNA molecules may be purchased, for example, from Eurogentec (UK), Bio-Synthesis (Louisville, Tex.), and Applied Biosystems Inc. (Foster City, Calif.), or synthesized by methods known in the art.

C. Hybridization Conditions

Generally, the design and/or choice of hybridization conditions is governed by several parameters, such as, but not limited to, the degree of complementarity of the nucleic acid analog molecule to the target polynucleotide, the length of the of the nucleic acid analog molecule to be utilized and the target polynucleotide itself. Preferred hybridization conditions allow for one or more of the following: efficient binding of nucleic acid analogs to target polynucleotides, minimization of RNA or DNA secondary structure, minimization of RNA degradation and either discrimination of one or more base pair changes or inclusion of one or more base pair changes.

Hybridization reactions can be performed under conditions of different "stringency". Conditions that effect stringency of a hybridization reaction are widely known and published in the art. See, for example, Sambrook et al. (2000), supra. Examples of relevant conditions include but are not limited to, salt concentrations, pH (buffers) and temperature. Hybridization conditions utilizing lower salt concentrations generally enhance double stranded DNA instability and promote PNA/polynucleotide stability. Examples of buffers that may be used include, but are not limited to, $Na_3PO_4$, $NaHSO_4$, $K_2HPO_4$, $K_2SO_4$, or $CaSO_4$. By way of example, the molarity of the buffers may range between about 0.5 mM and about 0.5 M and have a pH between about 4 to about 10, or between about 7 to about 10, such as about 7.0 or about 7.5. By way of example, $Na_3PO_4$ may be used at between about 0.5 mM and about 0.5 M, such as for example, 2.5 mM, and at a pH between about 4 to about or between about 7 to about 10, such as about 7 or about 7.5.

Examples of sample conditions include but are not limited to (in order of increasing stringency): incubation temperatures of about 25° C., about 37° C., about 50° C. and about 68° C.; buffer concentrations of about 10×SSC, about 6×SSC, about 4×SSC, about 1×SSC, about 0.1×SSC (where 1×SSC is 0.15 M NaCl and mM of any buffer as described herein) and their equivalents using other buffer systems; formamide concentrations of 0%, about 25%, about 50%, and about 75%; incubation times from about 5 minutes to about 24 hours; 1, 2, or more washing steps; wash incubation times of about 1, about 2, or about 15 minutes; and wash solutions of about 6×SSC, about 1×SSC, about 0.1×SSC, or deionized water. In a preferred embodiment hybridization and wash conditions are done at high stringency. By way of example hybridization may be performed at about 50% formamide and about 4×SSC followed by washes of about 2×SSC/formamide at about 50° C. and with about 1×SSC.

Buffers may contain ions or other compounds, or different buffering capacity. Alternatively a component in the buffer may have a stabilization capacity; such as neomycin or other aminoglycosides, that stabilizes triplex DNA, (Arya et al., J. AM. CHEM. SOC. 125:3733-44 (2003)) or naphthalene diimides that enhance triplex stability (Gianolio and McLaughlin, BIOORG. MED. CHEM. 9:2329-34 (2001)), or naphthylquinoline dimers (Keppler et al., FEBS LETT. 447:223-6 (1999)).

D. Dyes

The presence or amount of a polynucleotide may be determined by using one or more dyes for which the rate of change in an optical property is different in the presence of a nucleic acid analog/polynucleotide hybrid compared to the a known concentration of nucleic acid analog/polynucleotide hybrid. In one aspect, the optical property may be a change in color, absorbance, fluorescence, reflectance, or chemiluminescence. The optical property may also be measured at a single or multiple times during an assay.

The rate of change in an optical property of the dye may be compared to a reference value characteristic of the rate of change in the optical property of the dye in a mixture containing a known amount of a nucleic acid analog/polynucleotide hybrid or polynucleotide/PNA hybrid to determine a relative rate of change in the optical property. The reference value may be a qualitative or approximate value (e.g. the presence or absence of color). Alternatively, the reference value may be a numerical value. As another example, the reference value may be measured or determined before, during, or after the determination of the rate of change in the optical property of the dye for the sample. In a further example, the reference value may be a constant, such as a rate constant. The reference value may also be the rate of change in the optical property of dye in the absence of a target polynucleotide or polynucleotide/nucleic acid analog hybrids or nucleic acid analog (i.e., the known amount of a nucleic acid analog/polynucleotide hybrid is zero) or in the presence of nucleic acid analog of different sequence composition.

In some cases, the dye has a higher rate of change in the optical property in the presence of nucleic acid analog/polynucleotide hybrid than a reference value characteristic of the absence of a nucleic acid analog/polynucleotide hybrid. The presence or amount of the polynucleotide can thus be detected by an increase in the relative rate of change in the optical property compared to a reference value. Examples of dyes in which an optical property changes more rapidly in the presence of a nucleic acid analog/DNA hybrid include carbocyanine dyes, which are multi-ring aromatic compounds. These dyes absorb intensely in the visible range and bind preferentially to nucleic acid analog/polynucleotide hybrids in solution, changing color upon binding, Wilhelmsson et al., NUCLEIC ACID RES. 30:E3 (2002)). Examples of cyanine dyes include but are not limited to 3,3'-diethylthiacyanine iodide (Sigma, Milwaukee), 3,3'-diethylthiacarbocyanine iodide, 3,3'-diethylthiadicarbocyanine iodide, and 3,3'-diethylthiatricarbocyanine iodide.

In one embodiment, the dye is 3,3'-diethylthiacyanine iodide.

In one embodiment, the dye is 3,3'-diethylthiacarbocyanine iodide.

In one embodiment, the dye is 3,3'-diethylthiadicarbocyanine iodide.

In one embodiment, the dye is 3,3'-diethylthiatricarbocyanine iodide.

In one exemplary embodiment, under assay conditions described herein, 3,3'-diethylthiacarbocyanine turns from hot pink to clear with light stimulus in the presence of target nucleic acids and complementary PNA. In the absence of target nucleic acids the rate of change of the dye is slower. Light stimulus also decreases the fluorescent emission of the dye in the presence of target nucleic acids and complementary PNA. In the absence of light stimulus the dye immediately turns from hot pink to dull pink in the presence of target nucleic acids, and the fluorescent emission of the dye immediately decreases in the presence of target nucleic acids.

Under assay conditions described herein, 3,3'-diethylthiadicarbocyanine turns from blue to purple in the presence of target nucleic acids.

Under assay conditions described herein, 3,3-diethylthiatricarbocyanine remains aqua blue in the presence of target nucleic acids and turns clear in the absence of target nucleic acids.

In other cases, the dye has a lower rate of change in the optical property in the presence of nucleic acid analog/polynucleotide hybrid than in the absence of a nucleic acid analog/polynucleotide hybrid. The presence or amount of the polynucleotide can thus be detected by a decrease in the relative rate of change in the optical property compared to a reference value characteristic of the rate in the absence of a nucleic acid analog/polynucleotide hybrid.

Dyes may be selected from, for example, molecules that associate with nucleic acids in any of a variety of ways. Useful dyes include minor groove binders, major groove binders, intercalators and other polynucleotide-binding molecules, derivatives thereof, and conjugates thereto. Some dyes useful in the methods of the invention bind the minor groove of nucleic acid analog/polynucleotide hybrids. These dyes include carbocyanine dyes, such as 3,3'-diethylthiacarbocyanine iodide, 3,3'-diethylthiadicarbocyanine iodide, and 3,3'-diethylthiatricarbocyanine iodide. Examples include, but are not limited to, ethidium bromide (Fiebig et al., PROC. NATL. ACAD. SCI. USA 96:1187-92 (1999)), flourescein, phenothiazine dyes, such as methylene blue (Wagner, TRANSFUS. MED. REV. 16:61-66 (2002)), DAPI (Kapuscinski, J. BIOTECH. HISTOCHEM. 70:220-233 (1995)), thiazole orange (Boger et al., BIOORG. MED. CHEM. 9:2511-18 (2001); Carreon et al., ORG. LETT. 6:517-519 (2004)), Hoechst 33258 (Adhikary et al., NUCLEIC ACIDS RES 31:2178-86 (2003), Maiti et al., BIOCHEM. BIOPHYS. RES. COMMUN. 310:505-512 (2003), Morozkin et al., ANAL. BIOCHEM. 322:48-50 (2003), Tanious et al., J. AM. CHEM. SOC. 126:143-153 (2004), Tawar et al., BIOCHEMISTRY 18:13339-46 (2003)), SYBR Green II (Morozkin et al., supra), BEBO, BETO, BOXTO, BO, BO-PRO, TO-PRO, YO-PRO (Karlsson et al., NUCLEIC ACIDS RES. 31:6227-34, (2003), Eriksson et al., NUCLEIC ACIDS RES. 31:6235-42 (2003)), PicoGreen (Tolun and Myers, NUCLEIC ACIDS RES. 31:e 111 (2003)), TO-PRO-3 (Sovenyhazy et al., NUCLEIC ACIDS RES. 31:2561-9 (2003)), biscyanine dye (Schaberle et al., BIOPHYS. ACTA 1621:183-191 (2003)), methyl green-pyronin Y (Prento et al., BIOTECH. HISTOCHEM. 78:27-33 (2003)), ethidium bromide and acridine orange (Johnson et al., J. BIOMOL. STRUCT. DYN. 20:677-686 (2003), Lauretti et al., J. VIROL. METHODS 114:29-35 (2003), Luedtke et al., BIOCHEMISTRY 42:11391-403 (2003)), neutral red (Wang et al., BIOPHYS. CHEM. 104:239-48 (2003)), BO (Karlsson et al., BIOORG. MED. CHEM. 11: 1035-40 (2003)), mono- and bis-lexitropsins and pentamidine (Puckowska et al., EUR. J. MED. CHEM. 39:99-105 (2004)), 2-(methylthio) phenylsalicylaldimine Schiff base copper (II) (Reddy et al., J. INORG. BIOCHEM. 98:377-86 (2004)), a bifunctional platinum (II) complex (Ma and Che, CHEMISTRY 9:6133-44 (2003)), bis(9-aminoacridine-4-carboxamides) (Wakelin et al., J. MED. CHEM. 46:5791-802 (2003)), bisimidazoacridones (Tarasov et al., PHOTOCHEM. PHOTOBIOL. 78:313-22 (2003)), parallel or anitparallel carboxamide minor groove binders (Boutorine et al., NUCLEOSIDES NUCLEOTIDES NUCLEIC ACIDS 22:1267-72 (2003)), conjugates of oligo (2'-O-methylribonucleotides) with minor groove binders (Novopashina et al., NUCLEOSIDES NUCLEOTIDES NUCLEIC ACIDS 22:1179-82 (2003)), pyrrole-imidazole polyamines (Briehn et al., CHEMISTRY 9:2110-22 (2003), Dervan et al., CURR. OPIN. STRUCT. BIOL. 13:284-299 (2003), Reddy et al., J. AM. CHEM. SOC. 125:7843-48 (2003), Renneberg et al., J. AM. CHEM. SOC. 125:5707-16 (2003)), pyrrole (Huang et al., BIOORG. CHEM. 28:324-37 (2000)), bispyrrole (Carrasco et al., CHEMBIOCHEM. 3:50-61 (2003)), ruthenium complex (Kuwabara et al., ANAL. BIOCHEM. 314:30-37 (2003)), thallium (Ouameur et al., J. BIOMOL. STRUCT. DYN. 20:561-565 (2003)), aromatic diamidine (Nguyen et al., J. AM. CHEM. SOC. 124:13680-81 (2002)), chartreusin (Barcelo et al., NUCLEIC ACIDS RES. 30:4567-73 (2002)), platinum complex (Silverman et al., J. BIOL. CHEM. 277:49743-49 (2002)), S-3-nitro-2-pyridinesulfenyl-N-acetyl-cysteine (Shim et al., ORG. BIOMOL. CHEM. 2:915-21 (2004)), methylsulfonate esters (Varadarajan et al., BIOCHEMISTRY 42:14318-27 (2003)), peptide bis-intercalator (Guelev et al., CHEM. BIOL. 8:415-25 (2001)), metallointercalators (Proudfoot et al., BIOCHEMISTRY 40:4867-78 (2001), 2,2'-binaphthalene (Kondo et al., BIOORG. MED. CHEM. LETT. 14:1641-43 (2004)), intercalating nucleic acid (Christensen et al., NUCLEIC ACIDS RES. 30:4918-25 (2002), Nielsen et al., BIOCONJUG. CHEM. 15:260-9 (2004)), ruthenium (II) complex (Liu et al., INORG. CHEM. 43:1799-806 (2004)), cyclic polyamine neotrien/copper (II) complex (Biver et al., J. INORG. BIOCHEM. 98:33-40 (2004)), 2,6-disulfonic acid anthraquinone (Wong et al., ANAL. CHEM. 75:3845-52 (2003)), ferrocenyl anthracene, ferrocenyl, and other naphthalene diimide derivatives (Gianolio et al., supra; Takanaka et al., NUCLEIC ACIDS RES. SUPPL. 2002:291-2 (2002), Tok et al., BIOORG. MED. CHEM. LETT. 11:2987-91 (2001)), doxorubicin (Patolsky et al., ANGREW. CHEM. INT. ED. ENGL. 41:3398-402 (2002); Xiao et al., CHEM. COMMUN. (CAMB.) 7:1540-41 (2003)), acridin-9-ylthiourea (Baruah et al., NUCLEIC ACIDS RES. 31:4138-46(2003)), naphthalene diimide (Nojima et al., NUCLEIC ACIDS RES. SUPPL. 2001:105-6(2001), M. E. Numez et al., BIOCHEMISTRY 39:6190-99 (2000)), mitoxantrone (Wang et al., ACTA A. MOL. BIOMOL. SPECTROSC. 59:949-56 (2003)), cryptolepine and neocryptolepine (Guittat et al., BIOCHIMIE. 85:535-47 (2003)), iminodiacetic acid-linked polyamides (Woods et al., J. AM CHEM. SOC. 124:10676-82 (2002a)), dendritic polyamine conjugates (Brana et al., EUR. J. MED. CHEM. 37:541-51 (2002)), bis-intercalator delta-delta [mu-C49cpdppz)(2)-(phen)(4)Ru(2)] (Onfelt et al., J. AM CHEM. SOC. 123:3630-37 (2001); Onfelt et al., MUTAGENESIS 17:317-20 (2002)), ditercalinium (Berge et al., NUCLEIC ACIDS RES. 30:2980-86 (2002)), 8-methoxypsoralen (Arabzadeh et al., INT. J. PHARM. 237:47-55 (2002)), daunomycin and ellipticine (Reha et al., J. AM CHEM. SOC. 124:3366-76 (2002)), 1,4,5,8-naphthalene tetracarboxylic diimide (Guelev et al., J. AM CHEM. SOC. 124:2864-65 (2002)), cryptolepine (Lisgarten et al., NAT. STRUCT. BIOL. 9:57-60 (2002)), AMAC (Ferry et al., J. CHROMATOGR. B. BIOMED. SCI. APPL. 763:149-56 (2001)), (−)-6-[[(aminoalkyl)oxy]methyl]-4-demethoxy-6,7-dideoxydaunomcinones(1) (Dienes et al., J. ORG. CHEM. 61:6958-6970 (1996)), NLCQ-1 (Papadopoulou et al., ONCOL. RES. 12:325-33 (2000)), YOYO-1 (Wong et al., BIOCHIM. BIOPHYS. ACTA 1527:61-72 (2001)), DACA (Hicks et al., J. PHARMACOL. EXP. THER. 297:1088-98 (2001)), cyclometalated Rh(III) (Kisko et al., INORG. CHEM. 39:4942-49 (2000)), CI-958 (Dees et al., CLIN. CANCER RES. 6:3885-94 (2000)), pyrazoloacridine (Pelley et al., CANCER CHEMOTHER. PHARMACOL. 46:251-4 (2000)), cis-dichloroplatinum (II) complexes (Perrin et al., J. INORG. BIOCHEM. 81:111-7 (2000)), imidazoacridinones (Mazerski et al., ACTA BIOCHIM. POL. 47:65-78 (2000)), carbazole (Sajewicz et al., J. APPL. TOXICOL. 20:305-12 (2000)), 5,11-dimethyl-5H-indole[2,3-b]quinoline (Osiadacz et al., BIOORG. MED. CHEM. 8:937-43 (2000)), YOYO-3, netropsin, SN6999, A3 and SN6113 (Kirschstein et al., J. MOL. RECOGNIT. 13:157-63 (2000)), oxazole yellow (Inoue et al., BIOORG. MED. CHEM. 7:1207-11 (1999)), 5,6-chrysenequinone diimine complexes of rhodium (E) (Jackson et al., BIOCHEMISTRY 39:6176-82 (2000)), Nile blue (Chen et al., ANALYST. 124:901-6 (1999)), usambarensine (Dassonneville et al., ANTICANCER RES. 19:5245-50 (1999)), 3-methosybenzanthrone (Yang et al., SPECTOCHIM. ACTA A MOL. BIOMOL. SPECTROSC. 55A:2719-27 (1999)), 1,8-dihydroxyanthraquinones (Mueller et al., BIOCHIM. BIOPHYS. ACTA 1428:406-14 (1999)), cyclopropapyrroloindole (Dempcy et al., NUCLEIC ACIDS RES. 27:2931-37 (1999)), anthracene (Ostaszewski et al., BIOORG. MED. CHEM. LETT. 8:2995-6 (1998)), pyrrolizines and imidazoles (Atwell et al., J. MED. CHEM. 41:4744-54 (1998)), anthracycline complexes (Milano et al., Radiat. Re. 150:101-14 (1998)), heterodimers such athizole orange-thiazole blue, thiazole orange-ethidium and flourescein-ethidium (Benson et al., NUCLEIC ACIDS RES. 21:5720-26 (1993a); Benson et al., NUCLEIC ACIDS RES. 21:5727-35 (1993b)). In addition companies (e.g. Molecular Probes) sell many types of nucleic acid stains that may be compatible with the system. Other classes of cyanine dyes and state reactive dyes may be found in JOURNAL OF THE AMERICAN CHEMICAL SOCIETY 125:4132-4145 (2003) and BIOCONJUGATE CHEMISTRY 13:387-391 (2002). Examples of additional dyes include, but are not limited to, ternary copper(II) complexes (Dhar et al., J. AM CHEM. SOC. 125:12118-24 (2003)), distamycin A (Hiraku et al., NUCLEIC ACIDS RES. SUPPL. 2002: 95-96 (2002); Woods et al., BIOORG. MED. CHEM. LETT. 12:2647-50 (2002b)), indolo [2,3-b]-quinolizinium bromide (Viola et al., CHEMBIOCHEM. 3:550-8 (2002)), ecteinascidins (Anthoney et al., AM. J. PHARMACOGENOMICS 1:67-81 (2001)), metal amines (Barry et al., INORG. CHEM. 41:7159-69 (2002)), or 2-phenylquinoline-carbohydrate hybrids (Toshima et al., ANGEW. CHEM. INT. ED. ENGL. 38:3733-3735 (1999)). In some embodiments, the dye is not a compound that promotes cleavage.

Dyes may also include malachite green, red biarsenical dye and flourescein. In some embodiments, the dye is not malachite green, red biarsenical dye or flourescein.

One of skill in the art will recognize that dyes may be screened to identify those dyes that may be used in the present methods. Dyes that bind nucleic acid analog/polynucleotide hybrids and exhibit a change in an optical property over time, optionally after being provided with a stimulus, may be readily identified and selected.

One of skill in the art, guided by this disclosure, will recognize that in addition to the dyes listed herein, other dyes (including dyes discovered or developed in the future) may be used in the methods of the invention. Dyes for which the rate of change in an optical property is different in the presence and absence of a target polynucleotide/nucleic acid analog hybrid under the assay conditions described herein are suitable for the present methods.

Suitable dyes can be identified using any of a variety of screening methods. For example and not limitation, a sample containing a nucleic acid analog is combined with a polynucleotide having a complementary sequence under conditions under which a nucleic acid analog/polynucleotide hybrid is formed. In an embodiment, the candidate dye is then added, optionally at varying concentrations. The order of addition is not critical and components can be added in other orders. The rate of change in optical property over time is then determined. This rate is compared to a reference value characteristic of the rate of change in optical property of the dye in the absence of a nucleic acid analog/polynucleotide hybrid. In one embodiment, the reference value is characteristic of the absence of polynucleotide. In one embodiment, the reference value is characteristic of the presence of polynucleotide (single stranded or double stranded). In another embodiment, the reference value is characteristic of a non-zero concentration of polynucleotide. Dyes that exhibit a different rate of change in optical property over time compared to a reference value are selected for use in the claimed methods. The relative rate of change in the optical property is correlated with the presence or amount of specific polynucleotide.

E. Stimulus

The stimulus to the mixture that includes the nucleic acid analog that specifically binds a target polynucleotide, and a sample that may include a target polynucleotide, can be any form of energy that can trigger a chemical reaction of the substrate, such as a dye. Stimulus means usefully employed in the present invention include appropriate wavelengths of the visible and invisible light spectrum, heat, and the like. Preferred stimulus means include light as further set forth herein below. The stimulus means is provided to a sample, nucleic acid analog, and dye mixture either concurrently with the production of the mixture, or at a specified time after the production of the mixture. The stimulus causes a change in the rate of change in an optical property of the dye.

The stimulus, such as a light stimulus, may be applied to a mixture of the sample, nucleic acid analog, and dye in a continuous manner or over a discrete time period. The change in the optical property of the mixture may be observed while or after the mixture is exposed to the stimulus. The resultant change of the optical property in response to the stimulus does not substantially alter upon removal of the stimulus.

The light stimulus may be in the visible spectrum or outside the visible spectrum. The light stimulus may be white light of a number of wavelengths. Alternatively, the light stimulus may be a specific wavelength, or range of wavelengths. The light stimulus may also have a specific intensity.

Light sources are known in the art. Different light sources result in different reaction rates because of differences in intensity or wavelengths of the light sources. Examples of light sources, in ascending order of reaction rate, include Sylvania Cool White T8-CW, General Electric T8-C50, and Fritz Aurora 50/50. Other light sources include a Sylvania dulux S9W CF9DS/blue and a Osram F9TT/50K, which both result in faster light stimulated reaction rates than the General Electric T8-C50. Other examples of light sources include LEDs, including for example, Hebei 520 PGOC, 540IB7C and the Xenon USHIO UXL-553 lamp.

Those of skill in the art will recognize the optimal light stimulus may be determined without undue experimentation for a specific dye, or a specific nucleic acid analog, polynucleotide, and dye mixture. A single set of temperature and concentration conditions can be tested for a specific mixture.

IV. Forming a Target Polynucleotide/Nucleic Acid Analog Hybrid

Assays for detection of target polynucleotides can be carried out using a variety of hybridization schemes. In one format, the polynucleotide sequence may be identified by hybridization of a target polynucleotide directly to a nucleic acid analog to form a target polynucleotide/nucleic acid analog hybrid.

In one format, the nucleic acid analog may be PNA. PNA/PNA has a distance or pitch that is different from the DNA/DNA distance or pitch and from the PNA/DNA distance or pitch. The detailed structure of PNA/PNA and PNA/DNA duplex hybrids have been solved by NMR and X-ray crystallography. A PNA/PNA duplex hybrid has a very wide and deep major groove and a very narrow and shallow minor groove, and the duplex has a very large pitch of 18 base pairs per turn and a large pitch height (57.6 Å). A canonical B-form helix seen for a DNA/DNA duplex hybrid has a pitch of 10 base pairs per turn and 34 Å of pitch height, whereas a PNA/DNA duplex hybrid has a pitch of 13 base pairs per turn and 42 Å of pitch height. Because base pairs in a PNA/DNA duplex hybrid possess a different geometry compared with DNA double helices, the strength of the stacking interaction of PNA/DNA duplex hybrids is expected to be different from that of DNA/DNA duplex hybrids. CD spectra of 10, 12, and 16 mer PNA/DNA duplex hybrids suggest different base configuration for these duplex hybrids.

Depending on the dye and its binding site, a nucleic analog/polynucleotide hybrid can affect whether the reaction proceeds. For example, dyes that bind the major or minor groove of a hybrid may require the hybrid to contain a certain number of base pairs in order to bind effectively. The minimum number of base pairs can be determined easily by those of ordinary skill in the art.

In one aspect, a target nucleic acid analog molecule is complementary to a partially complementary nucleic acid analog. The nucleic acid analog hybridizes to both a nucleic acid analog molecule and a target polynucleotide, as depicted in FIG. 18A. This may be accomplished in a one step or multistep process. In a one step process, the target polynucleotide and nucleic acid analogs are combined in a single step. In a multistep process, the target polynucleotide and nucleic acid analogs are combined sequentially.

In a further aspect, the presence of a target polynucleotide may be detected by forming branched reaction crucifix form structure, an example of which is depicted in FIG. 18B. In this format, a target polynucleotide is hybridized to two intermediate polynucleotides that are partially complementary to the target polynucleotide. The intermediate polynucleotides form a branched structure that hybridizes to a target polynucleotide and a primary nucleic acid analog molecule. The target hybridizing regions of the intermediate polynucleotides may be designed to be too short for a dye to bind the nucleic acid analog molecule separately, but large enough to bind the nucleic acid analog molecules when hybridized. The rate of optical change of a dye may be then determined. In one embodiment, the single nucleic acid analog molecule may be a universal nucleic acid analog that is used for all assays, and optimized for effective changes in the optical property of a dye. The universal nucleic acid analog could be used for any target nucleic acid, and the intermediate sequences could be varied. This scheme can be adapted to a format using an immobilized nucleic acid analog.

In another format, multiple nucleic acid analog molecules form a nucleic acid analog/polynucleotide hybrid with adjacent regions of a target polynucleotide. In this format, each nucleic acid analog molecule is too short for a dye to bind and result in a change in the rate of optical property of the dye, but multiple nucleic acid analog molecules may provide a large enough region for a rate of change in optical property to result. As depicted in FIG. 18C, a target polynucleotide as a single molecule may be bound to form a nucleic acid analog/polynucleotide duplex by three separate nucleic acid analog molecules that hybridize to adjacent sequences. If the center nucleic acid analog molecule cannot hybridize as in FIG. 18D, however, then a change in optical property may not be observed. In this format, one of the nucleic acid analog molecules may be immobilized.

V. Quantifying the Amount of a Target Polynucleotide

The methods, compositions, and assay systems may be used to quantify the amount of target polynucleotide in a sample. In one embodiment, the amount of a target polynucleotide may be detected by establishing serial dilutions of the nucleic acid analog molecule, adding various amounts of the target polynucleotide samples, and comparing the samples to controls of known concentrations. In another embodiment, the amount of a target polynucleotide may be detected by establishing serial dilutions of the target polynucleotide, adding various amounts of the nucleic acid analog molecules, and comparing the samples to controls of known concentrations.

Alternatively, the amount of a target polynucleotide can be detected by measuring the kinetics of the assay based on time. Measurements of the dye in the combined mixture are taken at regular intervals after preparation of the mixture, or after application of light stimulus. The dye may be detected at distinct times after combination of the mixture, or after application of the light stimulus. The time may be any time period, for example the total time for the change in optical property, or the time required for the optical property to have changed by a certain percentage, such as, but not limited to, about 20%. The reactions can be frozen (further change stopped), for example with the addition of solvents such as 20% methanol, 15% isopropanol, 15% DMSO, or 10% butanol.

The reaction can also include a range of buffers and solvents. These buffers and solvents include phosphate buffers, water, 0.1% SDS, 0.1% Triton® X, 0.1% TWEEN® 20, 0.05% TWEEN® 80, 3% butanol, 10% methanol, 10% isopropanol, 10% DMSO, 1× blood lysis buffer (0.15 M $NH_4Cl$, 10 mM $NaHCO_3$, 0.1 mM EDTA pH 7.4), sucrose lysis buffer (0.32 M sucrose, 10 mM Tris, 1% Triton® X-100, 5 mM $MgCl_2$), and 5 mM phosphate buffer (pH 5.5) with 0.05% TWEEN® 80).

The quantity of polynucleotide in a sample may be determined after exposure to the light stimulus. The change in the optical property of the dye may be measured following pre-exposure to the light stimulus for the starting optical property. Measurements may be taken at distinct times (for example, taken at 30 second intervals) after exposure to the light stimulus. The reactions can be frozen (further change stopped) as described above.

Changes in the sample due to exposure to the light stimulus can be observed in several ways. The change in the optical property may be observed as a change in color, absorbance, fluorescence, reflectance, chemiluminescence, or a combination thereof. Alternatively, the change in optical property can be read using a reader. This change is measured using a spectrophotometer, such as Tecan Genios or a Tecan Safire. Specific wavelengths may be observed, for example by a filter. A positive control expresses a change in absorbance faster than a negative test. It can be measured as a difference in the rate of change, or the difference in the change at a set time. If fluorescent properties are observed, the light stimulus (excitation stimulus) provided to the sample is at a higher energy (lower wavelength) than the observed emission. The excitation may be at, for example, 535 nm and the emission may be read at 590 nm. The fluorescence may be measured as a difference in the rate of change or the difference in the change at a set time.

In addition the mixture may have a change that occurs before exposure to the light stimulus. This difference may be observed in either a spectrophotometric system, a fluorescence emission system, or a chemiluminescent system.

VI. Assay Formats

A. Liquid-Based Assay System

As demonstrated in Examples 1-4, the methods and assay system for detecting a target polynucleotide may be liquid-based. The sample, a nucleic acid analog that binds a target nucleic acid sequence of the polynucleotide in a sequence specific manner, and a dye for which the rate of change in the optical property is different in the presence and absence of a nucleic acid analog/polynucleotide hybrid, are combined to produce a mixture in liquid solution. The rate of change in the optical property of the dye in the mixture is compared to a reference value characteristic of the rate of change in the optical property of the dye in a similar mixture containing a known amount of a nucleic acid analog/polynucleotide hybrid to determine a relative rate of change in the optical property. The relative rate of change in the optical property of dye in the mixture correlates to the presence or amount of the specified polynucleotide in a sample to determine the presence or amount of polynucleotide in the sample.

The method and assay system may also be prepared in any vessel, such as microfuge tubes, test tubes, and chips that hold a liquid by surface tension. The methods and assay system may also be prepared in multiwell plates. The plates may contain any number of wells. In one format, 96 well plates are used. In another format, 384 plates are used. When the assay format is in a microwell format, the liquid is retained in each well of a microtiter plate.

B. Solid Support-Based Assay System

The methods and assay system may be solid based (e.g. one or more components are immobilized on a solid support). Most often, the nucleic acid analog or target polynucleotide is immobilized. There are many types of solid supports that the nucleic acid analog or target polynucleotide molecules may be attached to, including but not limited to: cast membranes (nitrocellulose, nylon), ceramic, track-etched membranes (TEM), polyvinylidenedifloride, latex, paramagnetic beads, plastic supports of all types, glass; powdered silica or alumina on a support matrix. If a grid pattern is used, the nucleic acid analog molecule/solid support forms a microarray. In another variation, the nucleic acid analog or target polynucleotide molecules may be covalently modified to include a linking moiety, such as a biotin or amide linkage, which binds to membranes. In a further variation, the nucleic acid analog or target polynucleotide molecules may be immobilized via sequence specific hybridization to one or more sequences.

Figure 17:
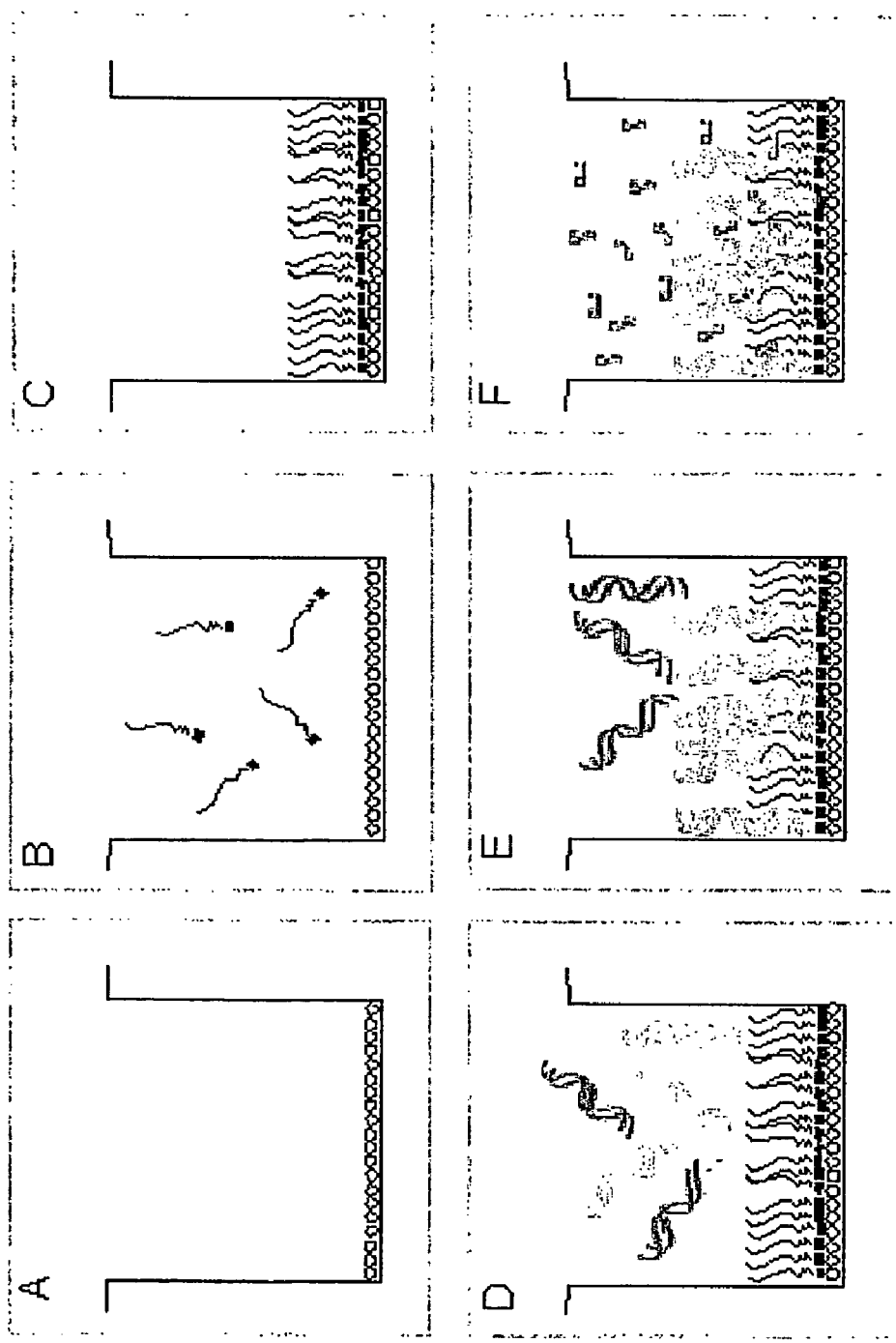
FIG. 17 depicts a schematic representation of light activated, surface immobilized detection of nucleic acid analogs.

FIG. 17 depicts a schematic representation of light stimulus activated, surface immobilized detection of polynucleotides captured by nucleic acid analogs. A) Streptavidin well.

B) Biotinylated nucleic acid analogs are added to the well and allowed to attach to the support. C) The well is washed and excess nucleic acid analogs are removed. D) Sample polynucleotide is added and specific sequence target attaches to the complementary nucleic acid analogs. E) Nonspecific and excess polynucleotide is washed off. F) Dye mixture is added and exposed to the light stimulus.

Any means of attaching a nucleic acid analog molecule to a support is contemplated by the instant invention. In one aspect, the nucleic acid analog molecule may be attached directly to a membrane. The nucleic acid analog may be a PNA (e.g., A Giger et al., NUCLEOTIDES AND NUCLEOSIDES 17:1717-1724 (1998)). A solution of nucleic acid analog molecules (in water) is simply applied to a charged or chemically modified filter and allied to air dry. The filter is then used for hybridization.

In another aspect, a biotin labeled nucleic acid analog molecule may be attached to a streptavidin-coated surface, such as a bead or well (see, e.g., Chandler et al., ANAL. BIOCHEM. 283:241-249 (2000)). Biotin labeled nucleic acid analog molecules mixed with streptavidin-labeled latex or polycarbonate beads. The Biotin binds strongly with streptavidin, allowing the nucleic acid analog molecule to bind to the bead in a unidirectional fashion. The beads are then applied to a non-charged membrane with a mesh size 25-30% greater that the diameter of the bead. Beads become trapped in the mesh, hence making a localized area of "attached nucleic acid analog molecules." Direct synthesis of nucleic acid analog molecules on a solid support such as a polypropylene membrane may be accomplished using standard 9-fluorenylmethoxycarboyl (Fmoc) protein synthesis chemistry (see, e.g., S. Matysiak et al., BIOTECHNIQUES 31:896-904 (2001)) or tboc protein synthesis chemistry (Nielsen, 1991, supra).

In another aspect, the nucleic acid analog molecules may be fixed to a glass or other solid support by applying a solution containing nucleic acid analog molecules in water directly to the glass or other support and letting it air dry.

In one variation, the nucleic acid analog molecule is designed to produce a net positive charge, and may bind a negatively charged membrane. For example, a positively charged lysine or glycine at a 5' or 3' end of the nucleic acid analog molecule may be used to attach the nucleic acid analog molecule to a negatively charged nylon membrane. The negatively charged membrane repels any nucleic acid that is not complementary and/or exactly complementary to the nucleic acid analog, thus minimizing non-specific binding.

Any target polynucleotide, or group of target polynucleotides, may be detected by the solid support-based system. In this case, a solid support contains multiple nucleic acid analog molecules immobilized on a solid support. A control nucleic acid analog that does not form nucleic acid analog/polynucleotide hybrid molecules, may be included on the solid support.

The solid support-based assay system may be used to detect at least one target polynucleotide. In other variations, the solid support-based system detects or measures the expression of at least about 8, at least about 10, at least about 20, at least about 30, at least about 40, at least about 50, or at least about 60 different target polynucleotides. In another variation, the solid support-based system detects and distinguishes expression of 60 or more target polynucleotides.

Figure 3:
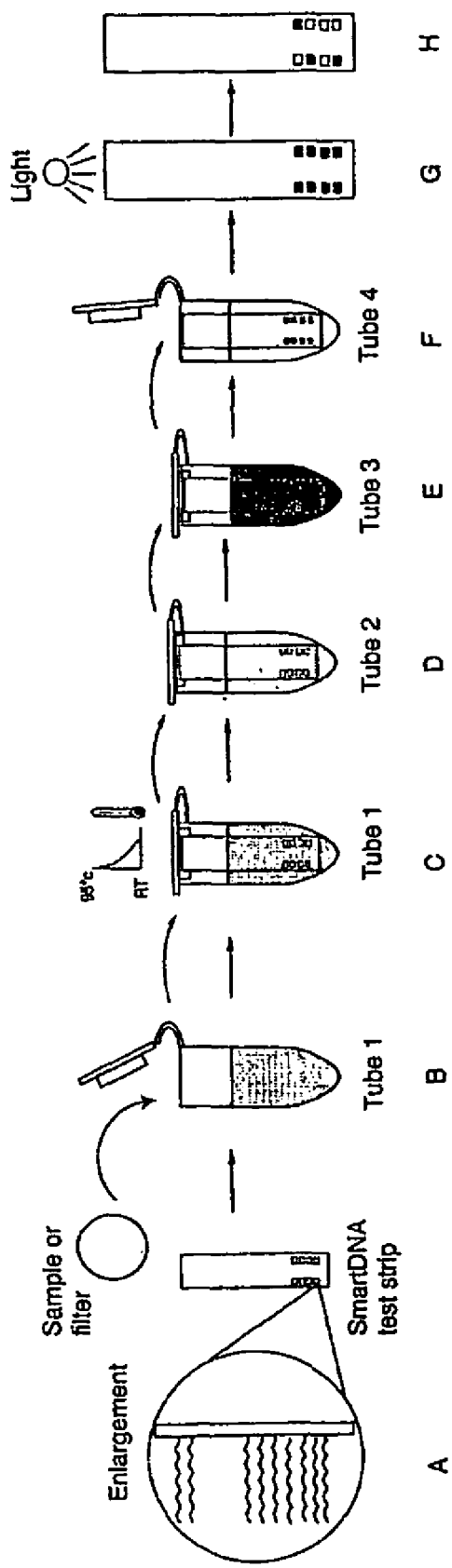
FIG. 3 is a schematic representation of a light activated PNA-based assay system.

As an example, and not for limitation, a solid support-based version of this assay using a membrane as a solid support is depicted in FIG. 3. The assay detects the presence of a target polynucleotide. The system allows small amounts of specific target polynucleotide to be identified and/or quantified within minutes, and gives a visual signal (e.g. rate of pink color changes to clear) without the need for extensive equipment. After sample lysis, hybridization, and introduction of the dye, a light stimulus is provided, and the rate of change of the colored pattern on the membrane is observed. The rate of change in the pattern of the colored bands on the membrane allows the user to easily determine the presence and identity of target polynucleotides. Optionally, the method or a variation thereof may be performed on a small battery operated hand-held device. In an automated robotic version all steps can be performed by a machine without human intervention.

The solid support based assay system may be in a microtiter plate arrangement. Any microtiter plate known in the art may be used. The assay components may remain liquid in such an assay system. In one format, 96-well plates are used. In another format, 384-well plates are used. When the assay is in a microtiter format, all components except for those bound to the solid surface remain in solution in each well of a microtiter plate.

VII. Target Polynucleotides and Sources of Target Polynucleotides

The target polynucleotide may be any polynucleotide, including naturally occurring, synthetic, and amplified. Other types of polynucleotides may be single or double stranded. Non-limiting examples of target polynucleotides include DNA, RNA, regulatory RNA, mRNA, regulatory microRNA, siRNA, artificial RNA, and chimeric RNA. Other non-limiting examples of target polynucleotides include epigenomic DNA, epigenetic DNA, in vitro amplified DNA, and chimeric DNA. The target polynucleotide may contain SNPs that are identified or quantitated by the methods disclosed herein.

The methods, systems, and assays described herein have a variety of uses. Non-limiting examples of these uses include detecting and quantifying organisms, pathogens, such as foodborne pathogens, environmental pathogens, waterborne pathogens, or pathogens implicated in agroterrorism. Other non-limiting uses include disease diagnosis such as sexually transmitted disease diagnosis, detection of genes conferring anti-biotic resistance, detection of genes conferring a predisposition for drug responses, detection of genes implicated in an effective drug response, detection of genetically modified organisms, and detection of non-indigenous flora or fauna. Additional non-limiting applications include agricultural applications and veterinary applications.

Examples, for illustration and not for limitation, are described below.

A. Pathogens

In one aspect, the invention relates to methods, compositions and assay systems for detecting the presence of a pathogen and/or the infection of a host by a pathogen. Generally, the presence of a pathogen and/or the presence of a pathogen in a host is detected by analysis of target polynucleotides in a sample. More specifically, the invention relates to methods, compositions of matter and assay systems for analyzing target polynucleotides by sequence specific hybridization to a nucleic acid analog molecule and addition of the dye to form a mixture. The rate of dye change in optical property is then observed to detect the presence or quantity of the target polynucleotide.

Examples of pathogens or presence of the pathogen in a host that may be detected by the methods and assay systems includes, but is not limited to, *Staphylococcus epidermidis, Escherichia coli*, methicillin-resistant *Staphylococcus aureus* (MSRA), *Staphylococcus aureus, Staphylococcus hominis, Enterococcus faecalis, Pseudomonas aeruginosa, Staphylococcus capitis, Staphylococcus warneri, Klebsiella pneumo-*

*niae, Haemophilus* influnzae, *Staphylococcus simulans, Streptococcus pneumoniae* and *Candida albicans*.

Additional examples include, but are not limited to, *Bacillus anthracis* (Anthrax), *Clostridium botulinum* (Botulism), Brucellae (Brucellosis), *Vibrio cholera* (Cholera), *Clostridium perfringens* (gas gangrene, Clostridial myonecrosis, enteritis necroticans), Ebola virus (Ebola Hemorrhagic Fever), *Yersinia pesits* (Plague), *Coxiella burnetii* (Q Fever), and Smallpox virus (Smallpox). In a preferred variation, infection by *Bacillus anthracis* is detected.

Examples of host response polynucleotides for *Bacillus anthracis* include, but are not limited to, those disclosed by M. Mock and T. Mignot (CELL MICROBIOL. 5:15-23 (2003)) and D. S. Reed et al. (CYTOMETRY 49:1-7 (2002)), or are easily obtained by methods known in the art.

Pathogens may be distinguished from other pathogens based on their target polynucleotides. Specific pathogens have specific target polynucleotides that are not found in other pathogens. Nucleic acid analog molecules are designed to be complementary or exactly complementary to one or more target polynucleotides that identify a specific pathogen. When contacted with the target polynucleotides of the pathogen, the nucleic acid analog molecule hybridizes to the polynucleotides containing the target polynucleotide, but not to polynucleotides that do not contain the target polynucleotide. Specific pathogens that contain a target polynucleotide may thus be distinguished from pathogens that do not contain the target polynucleotide.

In addition, different strains of the same pathogen may be distinguished. Different strains of the same pathogen have different polynucleotide sequences. Frequently, the differences are as few as a single nucleotide. Nucleic acid analog molecules are designed to be complementary or exactly complementary to one or more target polynucleotides that identify a specific strain of pathogen. When contacted with the target polynucleotides of the pathogen, the nucleic acid analog molecule hybridizes to the polynucleotides containing the target polynucleotide, but not to polynucleotides that do not contain the target polynucleotide. When the target polynucleotide is specific to a specific pathogen strain, nucleic acid analog molecules hybridize to the target polynucleotides contained in the pathogen strain, and do not hybridize to target polynucleotides of the different strain.

Examples of pathogens of clinical importance and the references for the PCR-based detection are listed below. Nucleic acid analog molecules may be designed to have the sequence of specific pathogen PCR primer sequences, and can be used in combination in many of the embodiments of the invention described herein.

In one embodiment, the pathogen may be *Staphylococcus epidermidis*. Nucleic acid analogs may be designed to have sequences or fragments of sequences similar or identical to PCR primers used to identify *Staphylococcus epidermidis*. Examples of these PCR primers are disclosed in the art (see, e.g., P. Francois et al., J. CLIN. MICROBIOL. 41:254-60 (2003); F. Fitzpatrick et al., J. HOSP. INFECT. 52:212-8 (2002); and J. Yugueros et al., J. CLIN. MICROBIOL. 38:4351-5 (2000).

The pathogen may be *Escherichia coli*. Nucleic acid analogs may be designed to have sequences or fragments of sequences similar or identical to PCR primers used to identify *Escherichia coli*. Examples of these PCR primers are disclosed in the art (see, e.g., L. C. Heller et al., APPL. ENVIRON. MICROBIOL. 69:1844-6 (2003); H. Rahman, INDIAN J. MED. RES. 115:251-4 (2002); and E. Frahm and U. Obst., J. MICROBIOL. METHODS 52:123-31 (2003)).

The pathogen may be methicillin-resistant *Staphylococcus aureus* (MSRA). Nucleic acid analogs may be designed to have sequences or fragments of sequences similar or identical to PCR primers used to identify *Staphylococcus aureus* (MSRA). Examples of these PCR primers are disclosed in the art (see, e.g., W. B. van Leeuwen et al., J. CLIN. MICROBIOL. 37:3029-30 (1999); P. Francois et al., J CLIN. MICROBIOL. 41:254-60 (2003); and M. Tsuruoka and I. Karube, COMB. CHEM. HIGH THROUGHPUT SCREEN 6:225-34 (2003)).

The pathogen may be *Candida*. Nucleic acid analogs may be designed to have sequences or fragments of sequences similar or identical to PCR primers used to identify *Candida*. Examples of these PCR primers are disclosed in the art (see, e.g., S. Ahmad et al., J. CLIN. MICROBIOL. 40:2483-9 (2002); and U. H. Tirodker et al., J. PERINATOL. 23:117-22 (2003)).

The pathogen may be *Candida albicans*. Nucleic acid analogs may be designed to have sequences or fragments of sequences similar or identical to PCR primers used to identify *Candida albicans*. Examples of these PCR primers are disclosed in the art (see, e.g., P. L. White et al., J. MED. MICROBIOL. 52:229-38 (2003); M. Grijalva et al., HEART 89:263-8 (2003); and B. Willinger et al., J. CLIN. MICROBIOL. 41:581-5 (2003)).

The pathogen may be *Staphylococcus aureus*. Nucleic acid analogs may be designed to have sequences or fragments of sequences similar or identical to PCR primers used to identify *Staphylococcus aureus*. Examples of these PCR primers are disclosed in the art (see, e.g., P. D. Francois et al., J. CLIN. MICROBIOL. 41:254-60 (2003); C. Palomares et al., DIAGN. MICROBIOL. INFECT. DIS. 45:183-9 (2003); and J. Xu et al., J. APPL. MICROBIOL. 94:197-206 (2003)).

The pathogen may be *Staphylococcus hominis*. Nucleic acid analogs may be designed to have sequences or fragments of sequences similar or identical to PCR primers used to identify *Staphylococcus hominis*. Examples of these PCR primers are disclosed in the art (see, e.g., R. Marsou et al., PATHOL. BIOL. (PARIS) 49:205-15 (2001); J. Yugueros et al., J. CLIN. MICROBIOL. 38:4351-5 (2000); and M. Wieser and H. J. Busse, INT. J. SYST. EVOL. MICROBIOL. 50:1087-93 (2000)).

The pathogen may be *Enterococcus faecalis*. Nucleic acid analogs may be designed to have sequences or fragments of sequences similar or identical to PCR primers used to identify *Enterococcus faecalis*. Examples of these PCR primers are disclosed in the art (see, e.g., C. R. Hudson et al., LETT. APPL. MICROBIOL. 36:245-50 (2003); S. M. Donabedian et al., J. CLIN. MICROBIOL. 41:1109-13 (2003); and V. Gauduchon et al., J. CLIN. MICROBIOL. 41:763-6 (2003)).

The pathogen may be *Pseudomonas aeriginosa*. Nucleic acid analogs may be designed to have sequences or fragments of sequences similar or identical to PCR primers used to identify *Pseudomonas aeriginosa*. Examples of these PCR primers are disclosed in the art (see, e.g., M. E. Corbella et al., APPL. ENVIRON. MICROBIOL. 69:2269-75 (2003); G. Agarwal et al., INDIAN J. MED. RES. 116: 73-81 (2002); and W. Dabrowski et al., FEMS MICROBIOL. LETT. 218:51-7 (2003)).

The pathogen may be *Staphylococcus capitis*. Nucleic acid analogs may be designed to have sequences or fragments of sequences similar or identical to PCR primers used to identify *Staphylococcus capitis*. Examples of these PCR primers are disclosed in the art (see, e.g., M. Wieser and H. J. Busse, INT. J. SYST. EVOL. MICROBIOL. 50:1087-93 (2000); and F. Martineau et al., J. CLIN. MICROBIOL. 34:2888-93 (1996)).

The pathogen may be *Staphylococcus warneri*. Nucleic acid analogs may be designed to have sequences or fragments of sequences similar or identical to PCR primers used to identify *Staphylococcus warneri*. Examples of these PCR primers are disclosed in the art (see, e.g., M. Wieser and H. J. Busse, supra; and T. Sashihara et al., BIOSCI. BIOTECHNOL. BIOCHEM. 64:2420-8 (2000)).

The pathogen may be *Klebsiella pneumoniae*. Nucleic acid analogs may be designed to have sequences or fragments of sequences similar or identical to PCR primers used to identify *Klebsiella pneumoniae*. Examples of these PCR primers are disclosed in the art (see, e.g., F. J. Perez-Perez and N. D. Hanson, J. CLIN. MICROBIOL. 40:2153-62 (2002); C. D. Steward et al., J. CLIN. MICROBIOL. 39:2864-72 (2001); and J. S. Carter and D. J. Kemp, SEX TRANSM. INFECT. 76:134-6 (2000)).

The pathogen may be *Haemophilus influenzae*. Nucleic acid analogs may be designed to have sequences or fragments of sequences similar or identical to PCR primers used to identify *Haemophilus* influnzae. Examples of these PCR primers are disclosed in the art (see, e.g., S. Shoma et al., J. HEALTH POPUL. NUTR. 19:268-74 (2001); C. E. Corless et al., J. CLIN. MICROBIOL. 39:1553-8 (2001); and J. S. Carter and D. J. Kemp., supra.

The pathogen may be *Staphylococcus simulans*. Nucleic acid analogs may be designed to have sequences or fragments of sequences similar or identical to PCR primers used to identify *Staphylococcus simulans*. Examples of these PCR primers are disclosed in the art (see, e.g., J. Yugueros et al., J. CLIN. MICROBIOL. 38:4351-5 (2000); and P. Szweda et al., PROTEIN EXPR. PURIF. 22:467-71 (2001)).

The pathogen may be *Streptococcus pneumoniae*. Nucleic acid analogs may be designed to have sequences or fragments of sequences similar or identical to PCR primers used to identify *Streptococcus pneumoniae*. Examples of these PCR primers are disclosed in the art (see, e.g., J. Xu et al., J. APPL. MICROBIOL. 94:197-206 (2003); O. Greiner et al., J. CLIN. MICROBIOL. 39:3129-34 (2001); and P. E. Corless, supra.

The pathogen may be Coronavirus, an RNA virus, for the detecting SARS. The sequence of coronavirus may be found, for example at the Center for Disease Control website. Examples of these target polynucleotides are disclosed in the art (see, e.g., T. G. Ksiazek et al., N. ENGL. J. MED. 348:1953-66 (2003); C. Drosten et al., N. ENGL. J. MED. 348:1967-1976 (2003)).

The pathogen may be *Bordetella pertussis*, or whooping cough. Examples of these target polynucleotides are disclosed in the art (Doucet-Populaire et al., ARCH. PEDIATR. 9:1145-52 (2002); J. R. Lingappa et al., J. CLIN. MICROBIOL. 40:2908-12 (2002).

The pathogen may be *Phytophthora ramorum* (the cause of sudden oak death). Examples of these target polynucleotides are disclosed in the art (see, e.g., L. Levy and V. Mavrodieva, Evaluation of the PCR Detection and DNA isolation methods for use in the *Phytophthora ramorum*, in 2003 NATIONAL PILOT SURVEY, available at the Purdue University website; B. A. McPherson et al., *Sudden Oak Death in California,* 2003 Home & Landscape, available at the University of California at Davis website).

The pathogen may be norwalk virus. Examples of these target polynucleotides are disclosed in the art (see, e.g., A. S. Khan et al., J. CLIN. MICROBIOL. 32:318-22 (1994); B. L. Herwaldt et al., J. CLIN. MICROBIOL. 32:861-6 (1994)).

The pathogen may be HIV. Nucleic acid analogs may be designed to have sequences or fragments of sequences similar or identical to PCR primers used to identify HIV. Examples of these PCR primers are disclosed in the art (see, e.g., K. M. Smith et al., J. NEUROVIROL. 6:164-71 (2000); R. Cuchacovich et al., RHEUM. DIS. CLIN. NORTH AM. 29:1-20 (2003); P. Cunningham et al. J. CLIN. VIROL. 26:163-9 (2003).

The pathogen may be *Mycobacterium tuberculosis*. Nucleic acid analogs may be designed to have sequences or fragments of sequences similar or identical to PCR primers used to identify tuberculosis. Examples of these PCR primers are disclosed in the art (see, e.g., M. J. Torres et al., DIAGN. MICROBIOL. INFECT. DIS. 45:207-12 (2003); B. Bhattacharya et al., TROP. MED. INT. HEALTH 8:150-7 (2003); M. Kafwabulula et al., INT. J. TUBERC. LUNG DIS. 6:732-7 (2002)).

In another embodiment, nucleic acid analogs are designed that bind to target polynucleotides common to an entire group of pathogens. For example, nucleic acid analogs may be designed to detect bacteria (BP6), gram positive bacteria (BP19), gram negative bacteria (BP3), and Fungi (FP8). Examples of the sequences of the nucleic acid analogs for BP6, BP19, BP3, and FP8 are shown below.

| | | |
|---|---|---|
| BP6 | oI2018 | 5'gaaSSMYcYaacacYtagcact [SEQ ID NO:3] |
| | oI2019 | 5'tacaaMgagYYgcWagacSgYgaS [SEQ ID NO:4] |
| BP19 | oI2021 | 5' gcagYWaacgcattaagcact [SEQ ID NO:5] |
| | oI2022 | 5'acgacacgagctgacgacaa [SEQ ID NO:6] |
| BP3 | oI2003 | 5' tctagctggtctgagaggatgac [SEQ ID NO:7] |
| | oI2004 | 5' gagttagccggtgcttcttct [SEQ ID NO:8] |
| FP8 | OI2055 | 5' cctgcggcttaatttgactca [SEQ ID NO:9] |
| | OI2057 | 5'tagcgacgggcggtgtgta [SEQ ID NO:10] |

The nucleic acid analogs can be used in clinical applications for the diagnosis of the microbial cause of sepsis or in other applications where the microbial content of products in important in evaluating their shelf-life and stability or other products where the sterility is being assessed.

Target polynucleotides may be specific to ribosomal RNA sequences, such as 16S RNA in *E. coli*. Ribosomal RNA contains specific sequences that are characteristic to their organism. By using nucleic acid analog sequences that are complementary or exactly complementary to a target polynucleotide characteristic of the ribosomal RNA sequence, pathogens may be identified based on their ribosomal RNA sequences. Ribosomal RNA sequences characteristic of different pathogens or strains of pathogens, may be found, for example, at (D. J. Patel et al., J. MOL. BIOL. 272:645-664 (1997)).

B. Host Response Polynucleotides

The target nucleotide may also be a host response polynucleotide. After a host is infected with a pathogen, host genes may be differentially expressed in response to the pathogen to produce a pattern of mRNA expression (gene expression profile). The host genes whose pattern of expression correlates with infection by a specific pathogen are referred to as "diagnostic marker genes" for that agent. The mRNA is typically derived from white blood cells in the sample. Methods of identifying a host response and altered gene expression profiles may be found, for example, in 1) R. Das et al., PROCEEDINGS: 21ST ARMY SCI. CON. 1998:61-62 (1998); and C. Mendis et al., MOL. BIOL. CELL. 9:450_(1998).

Methods for gene expression profiling have been developed to diagnose various medical conditions, as described, for example, in U.S. Pat. No. 5,723,290 to Eberwine et al., U.S. Pat. No. 6,218,122 to Friend et al., WO 99/10536 to Yarramilli et al., and WO 99/57130 to Prashar et al. Briefly, the method involves obtaining the level of mRNA expression in selected cells associated with a selected condition and comparing the relative levels obtained with established controls. A diagnosis is then made based upon the comparison of the mRNA expression levels. The mRNA is isolated from cells by any one of a variety of techniques well known in the art, but in general, lyse the cells and then enrich for or purify RNA. Gene expression profiles are then produced by any means known in the art, including, but not limited to the methods disclosed by: Prashar et al. in WO 97/05286; Liang et al. in SCIENCE 257:967-971 (1992); Ivanova et al. in NUCLEIC ACIDS RES. 23:2954-2959 (1995); and Prashar et al. in PROC. NATL. ACAD. SCI. USA 93: 659-663 (1996). These techniques typically produce gene expression profiles using northern analysis, FRET detection, hybridization to an oligonucleotide array, hybridization to a cDNA array, cDNA sequencing, cDNA fingerprinting, and the like. Oftentimes, the gene expression profile refers to a representation of the expression of mRNA species such as may be found in an autoradiograph of labeled cDNA fragments produced from total cellular mRNA separated on the basis of size by slab gel electrophoresis, capillary gel electrophoresis, HPLC, and other separation methods.

The assay systems and methods of this invention provide an alternative way to assess mRNA expression. As further described below, levels of mRNA expression (i.e., gene expression profiles) are compared, or alternatively alterations in mRNA expression from diagnostic marker genes are detected by assaying for hybridization of host response mRNAs to their complementary or exactly complementary nucleic acid analogs.

C. Foodborne and Environmental Pathogens

Any foodborne or environmental pathogens may be detected by the present invention. Foodborne pathogens include, but are not limited to, *Listeria, Campylobacter, E. coli* and *Salmonella*. The nucleic acid analog methods disclosed herein readily allow the detection of specific foodborne pathogens. For example, *Listeria* may be readily distinguished from *Salmonella*. Further, specific strains of foodborne pathogens, such as specific strains of *L. monocytogenes*, may be detected.

Any target polynucleotide associated with foodborne pathogens may be identified by the methods of the present invention. Target polynucleotides that characterize specific pathogens and strains of pathogens may be identified, as discussed above. The method may be used to detect target polynucleotides associated with *Listeria, Campylobacter, E. coli* and *Salmonella*. For example, specific *Listeria* genes that may be identified by the methods disclosed herein include hly (listeriolysin O) and iap (invasion associated protein) genes and mRNA (HLYPNA and IAPPNA, respectively).

Target polynucleotides having polynucleotide sequences corresponding to *Salmonella* spp may be detected. Sequences specific to *Salmonella* spp are known in the art (see, e.g., F. J. Perez-Perez, supra; S. D. Oliveira et al., LETT. APPL. MICROBIOL. 36:217-21 (2003); and C. M. Strapp et al., J. FOOD PROT. 66:182-7 (2003)).

In another embodiment, target polynucleotides having polynucleotide sequences corresponding to *Escherichia coli* may be detected. Sequences specific to *Escherichia coli* are known in the art (see, e.g., L. C. Heller et al., APPL. ENVIRON. MICROBIOL. 69:1844-6 (2003); H. Rahman, INDIAN J. MED. RES. 115:251-4 (2002); and E. Frahm and U. Obst, J. MICROBIOL. METHODS 52:123-31 (2003)).

In another embodiment, target polynucleotides having polynucleotide sequences corresponding to *Campylobacter* spp. may be detected. Sequences specific to *Campylobacter* spp. are known in the art (see, e.g., J. S. Carter and D. J. Kemp, supra; Y. Moreno et al., APPL. ENVIRON. MICROBIOL. 69:1181-6 (2003); and D. D. Bang et al., MOL. CELL PROBES 16:359-69 (2002)).

In a further embodiment, target polynucleotides having polynucleotide sequences corresponding to *Bacillus* spp. may be detected. Sequences specific to *Bacillus* spp. are known in the art (see, e.g., V. Mantynen and K. Lindstrom, APPL. ENVIRON. MICROBIOL. 64:1634-9 (1998); H. Schraft and M. W. Griffiths, APPL. ENVIRON. MICROBIOL. 61:98-102 (1995); and B. E. Ley et al., EUR. J. CLIN. MICROBIOL. INFECT. DIS. 17:247-53 (1998)).

The target polynucleotides having sequences corresponding to *Pseudomonas* spp. may also be detected. Sequences specific to *Pseudomonas* spp. are known in the art (see, e.g., J. Xu et al., J. APPL. MICROBIOL. 94:197-206 (2003); B. E. Ley et al., Eur. J. CLIN. MICROBIOL. INFECT. DIS. 17:247-53 (1998); and K. Johnsen et al., APPL. ENVIRON. MICROBIOL. 65:1786-8 (1999).

The target polynucleotides may also have polynucleotide sequences corresponding to *Enterococcus* spp. may be detected. Sequences specific to *Enterococcus* spp. are known in the art (see, e.g., C. R. Hudson et al., LETT. APPL. MICROBIOL. 36:245-50 (2003); S. M. Donabedian et al., J. CLIN. MICROBIOL. 41:1109-13 (2003); and S. B. Vakulenko et al., ANTIMICROB. AGENTS CHEMOTHER. 47:1423-6 (2003)).

Target polynucleotides may also have polynucleotide sequences corresponding to *E. coli* O157. Sequences specific to *E. coli* O157 are known in the art (see, e.g., T. M. Pan et al., J. FORMOS. MED. ASSOC. 101:661-4 (2002); D. J. Bopp et al., J. CLIN. MICROBIOL. 41:174-80 (2003); A. M. Ibekwe and C. M. Grieve, J. APPL. MICROBIOL. 94:421-31 (2003)).

Target polynucleotides may have polynucleotide sequences corresponding to *Listeria* spp. and *L. monocytogenes*. Sequences specific to *Listeria* spp. and *L. monocytogenes* are known in the art (see, e.g., D. Volokhov et al., J. CLIN. MICROBIOL. 40:4720-8 (2002); L. Cocolin et al. APPL. ENVIRON. MICROBIOL. 68:6273-82 (2002); A. E. Shearer et al., J. FOOD PROT. 64:788-95 (2001); A. Bubert et al., APPL. ENVIRON. MICROBIOL. 65:4688-92 (1999); Y. S. Jung et al., J. FOOD PROT. 66:237-41 (2003); and D. Pangallo et al., NEW MICROBIOL. 24:333-9 (2001)).

The target polynucleotides having polynucleotide sequences corresponding to coliforms may be detected. Sequences specific to coliforms are known in the art (see, e.g., N. Casas and E. Sunen, MICROBIOL. RES. 157:169-7 (2002); E. Schvoerer et al., RES. MICROBIOL. 152:179-86 (2001); A. E. Bernhard and K. G. Field, APPL. ENVIRON. MICROBIOL. 66:1587-94 (2000)).

In another embodiment, target polynucleotides having polynucleotide sequences corresponding to *Vibrio cholerae* and *V. parahaemolyticus* may be detected. Sequences specific to *Vibrio cholerae* and *V. parahaemolyticus* are known in the art (see, e.g., M. L. Myers et al., APPL. ENVIRON. MICROBIOL. 69:2194-200 (2003); G. M. Blackstone et al., J. MICROBIOL. METHODS. 53:149-155 (2003); and W. J. Lyon, APPL. ENVIRON. MICROBIOL. 67:4685-93 (2001)).

In a further embodiment, target polynucleotides having polynucleotide sequences corresponding to molds may be detected. Sequences specific to molds are known in the art (see, e.g., G. Zur et al., J. FOOD PROT. 2002 September; 65 (9):1433-40; L. Jimenez et al., J. MICROBIOL. METHODS 41:259-65 (2000); and N. Vanittanalcom et al., J. CLIN. MICROBIOL. 40:1739-42 (2002)).

The target polynucleotides may have polynucleotide sequences corresponding to *Legionella*. Sequences specific to *Legionella* are known in the art (see, e.g., S. Aoki et al., J. MED. MICROBIOL. 52:325-9 (2003); R. B. Raggam et al., MED.

MICROBIOL. IMMUNOL. (Berl) 191:119-25 (2002); and S. Alexiou-Daniel et al., CLIN. MICROBIOL. INFECT. 4:144-148 (1998)).

Host response mRNA may also be detected in response to infection by foodborne pathogens.

D. Waterborne Pathogens

The methods disclosed herein also provide a rapid and sensitive diagnostic test for the presence and enumeration of waterborne pathogens. Waterborne pathogens include bacteria, viruses, and protozoans. Examples of water-borne pathogens include *Enterococci, E. coli, Bacillus* spp., *Pseudomonas* spp., *Cryptosporidium,* and *Giardia*. Waterborne pathogens may be obtained from any water sample, including, but not limited to, swimming pools, aquatic parks, wells, home drinking water, reservoirs, beaches, lakes, oceans, fish and shellfish farms, agricultural water, dialysis water, medication reconstitution water, water treatment facilities, cruise ships, space shuttle effluent, and bottled water.

The methods disclosed herein readily allow the detection of waterborne pathogens. By way of example, specific strains may be detected. For example, specific strains of *Enterococci* that be can be detected over other strains include *Enterococci avium, E. casseliflavus, E. cecorum, E. columbae, E. dispar, E. durans, E. faecium, E. faecalis, E. gallinarum, E. hirae, E. malodoratus, E. mundtii, E. pseudovium, E. raffinosus, E. saccharolyticus,* and *E. sulfurous*.

Any polynucleotide associated with waterborne pathogens may be identified by the methods of the present invention. The method may be used to detect genes associated with *Enterococcus* spp., *E. coli, Bacillus* spp., and *Psuedomonas* spp., which have been described (re *Escherichia coli*: L. C. Heller et al., APPL. ENVIRON. MICROBIOL. 69:1844-6 (2003); H. Rahman, INDIAN J. MED. RES. 115:251-4 (2002); and E. Frahm and U. Obst, J. MICROBIOL. METHODS 52:123-31. Re *Bacillus* spp.: V. Mantynen and K. Lindstrom, APPL. ENVIRON. MICROBIOL. 64:1634-9 (1998); H. Schaft and M. W. Griffiths, APPL. ENVIRON. MICROBIOL. 61:98-102 (1995); and B. E. Ley et al., Eur. J. CLIN. MICROBIOL. INFECT. DIS. 17 (4):247-53, (1998). Re *Pseudomonas* spp.: J. Xu et al., J. APPL. MICROBIOL. 94:197-206 (2003); B. E. Ley et al., supra; and K. Johnsen et al., APPL. ENVIRON. MICROBIOL. 65:1786-8 (1999). Re *Enterococcus* spp.: C. R. Hudson et al., LETT. APPL. MICROBIOL. 36:245-50 (2003); S. M. Donabedian et al., J. CLIN. MICROBIOL. 41:1109-13 (2003); and S. B. Vakulenko et al., ANTIMICROB. AGENTS CHEMOTHER. 47:1423-6 (2003). For example, specific *Enterococci* genes that may be identified by the methods disclosed herein include 16S ribosomal RNA sequences that are conserved in *Enterococci*.

Host response mRNA may also be detected in response to infection by waterborne pathogens.

E. Agroterrorism

Nucleic acid analogs may be designed to have the sequences of primers used for PCR-based detection of specific pathogens implicated in agroterrorism. Examples of pathogens of clinical importance and the references for the PCR-based detection are listed below. Nucleic acid analogs may be designed to have the sequence of specific PCR primer sequences, and can be used in combination in many of the embodiments of the invention described herein.

Nucleic acid analogs may be designed, for example, to have the sequences of primers, or fragments thereof, used for PCR-based detection of *Toxoplasma gondii*. *Toxoplasma gondii* has very low host specificity, and probably infects almost any mammal. It has also been reported from birds, and has been found in virtually every country of the world. Like most of the *Apicomplexa, Toxoplasma* is an obligate intracellular parasite. In most humans infected with *Toxoplasma,* the disease is asymptomatic. However, under some conditions, toxoplasmosis can cause serious pathology, including hepatitis, pneumonia, blindness, and severe neurological disorders. Primers used in PCR-based detection of *Toxoplasma gondii* are known in the art (see, e.g., T. V. Aspinall et al., INT. J. PARASITOL. 32:1193-9 (2002); T. V. Aspinall, INT. J. PARASITOL. 33:97-103 (2003); I. Fuentes, J. CLIN. MICROBIOL. 39:1566-70 (2001); and M. R. Warnekulasuriya et al., INT J. FOOD MICROBIOL. 45:211-5 (1998)).

In another embodiment, nucleic acid analogs may be designed to have the sequences of primers, or fragments thereof, used for PCR-based detection of *Shingella* spp, a gram negative bacterium. Primers used in PCR-based detection of *Shingella* spp are known in the art (A. B. Hartman et al., J. CLIN. MICROBIOL. 41:1023-32 (2003); K. A. Lampel and P. A. Orlandi, METHODS MOL. BIOL. 179:235-44 (2002); R. F. Wang et al., J. APPL. MICROBIOL. 83:727-36 (1997); and K. A. Lampel et al., APPL. ENVIRON. MICROBIOL. 56:1536-40 (1990)).

In a further embodiment, nucleic acid analogs may be designed to have the sequences of primers, or fragments thereof, used for PCR-based detection of *Cyclospora cayetanensis*. *Cyclospora cayetanensis* is a parasite composed of one cell, too small to be seen without a microscope. The first known human cases of illness caused by *Cyclospora* infection (i.e., cyclosporiasis) were reported in 1979. Cases began being reported more often in the mid-1980s. In the last several years, outbreaks of cyclosporiasis have been reported in the United States and Canada. *Cyclospora* is spread by ingestion of water or food that was contaminated with infected stool. Outbreaks of cyclosporiasis have been linked to various types of fresh produce. *Cyclospora* needs time (days or weeks) after being passed in a bowel movement to become infectious. Therefore, it is unlikely that *Cyclospora* is passed directly from one person to another.

Primers used in PCR-based detection of *Cyclospora cayetanensis* are known in the art (see, e.g., M. L. Eberhard et al., ARCH. PATHOL. LAB. MED. 121:792-7 (1997); N. J. Pieniazek et al., EMERG. INFECT. DOIS. 2:357-9 (1996); W. Quintero-Betancourt et al., J. MICROBIOL. METHODS 49:209-24 (2002); and M. Varma et al., J. MICROBIOL. METHODS 53:27-36 (2003)).

F. Disease Diagnostics

The methods disclosed herein also provide a rapid and sensitive diagnostic test for the presence of genes (e.g., disease alleles) or altered expression of genes. The detected gene sequences may be implicated in genetic diseases, disorders, and predispositions. One example of target polynucleotides includes specific genomic sequences, including mutations, polymorphisms, additions and deletions. Another example of target polynucleotides is polynucleotide sequences that have altered gene expression (e.g., up-regulated or down-regulated expression) in a specific disease or disorder. Examples of disease and disorder-related genes include, but are not limited to, genes implicated in cancer, cystic fibrosis, and Down's syndrome, and disease-associated polymorphisms and mutations. Hereditary hemachromatosis, factor 11 and factor V, and HLA genotypes for tissue transplants may also be identified.

Nucleic acid analogs may be designed to have the sequences of primers, or fragments thereof, used for PCR-based detection of target polynucleotides implicated in cancer, or altered cell proliferation. Target polynucleotides corresponding to genes implicated in cancer, or altered cell proliferation, may be detected. Numerous genes implicated in cancer are known in the art.

In one embodiment, nucleic acid analogs may be designed to have the sequences of primers, or fragments thereof, used for PCR-based detection of pancreatic cancer. Primers used in PCR-based detection of pancreatic cancer, such as loss of DPC4, are known in the art (see, e.g., V. M. Barbera et al., BIOCHEM. BIOPHYS. ACTA 1502:283-96 (2000); D. Bartsch et al., CANCER LETT. 139:43-9 (1999); and D. Bartsch et al., ONCOGENE 18:2367-71 (1999)).

In another embodiment, nucleic acid analogs may be designed to have the sequences of primers, or fragments thereof, used for PCR-based detection of cervical cancer. Primers used in PCR-based detection of cervical cancer. Target polynucleotides corresponding to all or part of the genes associated with cervical cancer may also be identified (see, e.g., (H. X. Si et al., INT. J. CANCER 103 (4):496-500 (2003); and P. E. Castle et al., J. MED. VIROL. 68:417-23 (2002)).

Nucleic acid analogs may be designed to have the sequences of primers, or fragments thereof, used for PCR-based detection of breast cancer. Primers used in PCR-based detection of breast cancer. Target polynucleotides may be selected to have sequences corresponding to all or part of the genes associated with breast cancer (see, e.g., C. J. Min et al., CANCER RES. 58:4581-4 (1998); M. R. Abbaszadegan et al., GENET. TEST 1:171-80 (1997); and G. Tamura et al., PATHOL. INT. 44:34-8 (1994)).

Nucleic acid analogs may be designed to have the sequences of primers, or fragments thereof, used for PCR-based detection of melanoma. Primers used in PCR-based detection of melanoma. Target polynucleotides may be selected to have sequences corresponding to all or part of the genes associated with melanoma. For example, target polynucleotides may include mutations in CDKN2 (see, e.g., M. L. Gonzalgo et al., Cancer Res 57:5336-47 (1997); J. Chan et al., Mol. Carcinog. 31:16-26 (2001); and P. M. Pollock et al., Cancer Res 61:1154-61 (2001)).

In addition, nucleic acid analogs may be designed to have the sequences of primers, or fragments thereof, used for PCR-based detection of colorectal cancer. Primers used in PCR-based detection of colorectal cancer. Target polynucleotides may be selected to have sequences corresponding to all or part of the genes associated with colorectal cancer (see, e.g., S. Coli et al., J. EXP. CLIN. CANCER RES. 21:555-62 (2002); R. Shtoyerman-Chen et al., GENET. TEST 5:141-6 (2001); and W. M. Smith et al., GENET. TEST 2:43-53 (1998)).

Nucleic acid analogs may be designed to have the sequences of primers, or fragments thereof, used for PCR-based detection of retinoblastoma. Primers used in PCR-based detection of retinoblastoma. Target polynucleotides may be selected to have sequences corresponding to all or part of the genes associated with retinoblastoma (see, e.g., I. Acikbas et al., UROL. INT. 68:189-92 (2002); G. Tamura et al., PATHOL. INT. 44:34-8 (1994); and D. Lohmann et al., HUM. GENET. 89:49-53 (1992).

In a further embodiment, nucleic acid analogs may be designed to have the sequences of primers, or fragments thereof, used for PCR-based detection of hemopheilia. Primers used in PCR-based detection of hemophelia. Target polynucleotides may be selected to have sequences corresponding to genes associated with hemophelia (see, e.g., P. M. Mannucci, HEMATOLOGY (Am. Soc. Hematol. Educ. Program): 1-9 (2002); and M. Citron et al., HUM. MUTAT. 20:267-74 (2002)).

Target polynucleotides that have sequences corresponding to genes associated with phenylketylurea (PKU) may be selected (see, e.g., N. Pronina et al., HUM. MUTAT. 21:398-9 (2003); H. Sueoka et al., GENET. TEST 4:249-56 (2000); and R. C. Eisensmith et al., PRENAT. DIAGN. 14:1113-8 (1994)). R. L. Alford et al., AM. J. MED. GENET. 66:281-6 (1996); C. L. Vnencak-Jones, METHODS MOL. BIOL. 217:101-8 (2003); and I. Panagopoulos et al., HUM. MUTAT. 13:232-6 (1999)).

Target polynucleotides that have sequences corresponding to genes associated with Huntington's Disease may be selected, for example, due to increased CAG repeats (see, e.g., R. L. Alford et al., supra; C. L. Vnencak-Jones, supra; and I. Panagopoulos et al., supra).

Target polynucleotides that have sequences corresponding to genes associated with Tay-Sach's Disease may be selected (see, e.g., J. E. Rice et al., PRENA. DIAGN. 22:1130-4 (2002); S. Tamasu et al., KOBE J. MED. SCI. 45:259-70 (1999) and K. Sermon et al., HUM. REPROD. 10:2214-7 (1995)).

Target polynucleotides that have sequences corresponding to genes associated with Multiple Schlorosis (MS) may be selected (see, e.g., S. Lauwers et al., J. PHARM. BIOMED. ANAL. 29:659-68 (2002); H. Perron et al., PROC. NATL. ACAD. SCI. USA 94:7583-8 (1997); and B. S. Kuhne et al., BIOTECHNIQUES 33:1078, 1080-2, 1084 passim (2002)).

Target polynucleotides may be selected to have sequences corresponding to genes associated with Burkitt's lymphoma (see, e.g., Y. Wu, ZHONGHUA ZHONG LIU ZA ZHI 24:348-52 (2002); K. Basso et al., AM. J. PATHOL. 155:1479-85 (1999); and M. Asada et al., JPN. J. CANCER RES. 82:848-53 (1991)).

Target polynucleotides may be selected to have sequences corresponding to genes associated with cystic fibrosis (see, e.g., R. Tomaiuolo et al., CLIN. CHEM. LAB. MED. 41:26-32 (2003); M. C. Gonzalez-Gonzalez et al., PRENAT. DIAGN. 22:946-8 (2002); and C. Corbetta et al., J. MED. SCREEN 9:60-3 (2002)).

Target polynucleotides may be selected to have sequences corresponding to genes associated with juvenile onset diabetes (see, e.g., I. Knerr et al., PEDIATR. RES. 46:57-60 (1999); S. Lauwers et al., J. PHARM. BIOMED. ANAL. 29:659-68 (2002); and K. Salminen et al., J. MED. VIROL. 69:91-8 (2003)).

Target polynucleotides may be selected to have sequences corresponding to genes associated with Parkinson's disease (see, e.g., J. Hoenicka et al., ARCH. NEUROL. 59:966-70 (2002); C. B. Lucking et al., METHODS MOL. BIOL. 217:13-26 (2003); W. D. Le et al., NAT. GENET. 33:85-9 (2003); and T. Foroud et al., NEUROLOGY 60:796-801 (2003)).

Target polynucleotides may be selected to have sequences corresponding to genes associated with Alzheimer's Disease (see, e.g., G. A. Maresh et al., J. NEUROCHEM. 67:1132-44 (1996); and M. J. Smith et al., NEUROREPORT. 10:503-7 (1999)).

Target polynucleotides may be selected to have sequences corresponding to genes associated with thrombosis (see, e.g. J. Sanders Sevall, MOL. CELL. PROBES 14:249-53 (2000); A. Ferreira-Gonzalez et al., J. CLIN. LAB. ANAL. 11:328-35 (1997); I. Warshawsky et al., DIAGN. MOL. PATHOL. 11:152-6 (2002)).

Target polynucleotides may be selected to have sequences corresponding to genes associated with susceptibility to tuberculosis (see, e.g., R. Bellamy, GENES IMMUN. 4:4-11 (2003); A. A. Awomoyi et al., J. INFECT. DIS. 186:1808-14 (2002); R. Bellamy, Int. J. Tuberc. LUNG DIS. 6:747 (2002)).

Target polynucleotides may be selected to have sequences corresponding to genes associated with human immunodeficiency virus (HIV) (see, e.g., I. Ifergan et al., AIDS 16:2340-2 (2002); and M. Farzan et al., CELL 96:667-76 (1999)). The methods herein also provide a rapid and sensitive diagnostic test for the presence of genes or altered expression of genes in other kinds of genetic analysis. For example, the may be used to determine the identity of human samples, for example in paternity tests, forensics, or in matching related or unrelated organ donors. Diagnostics may also be conducted in non-human samples, such as to identify cattle lineages.

G. Sexually Transmitted Diseases

The nucleic acid analogs may be designed to have the sequences, or fragments of the sequences, of primers used for PCR-based detection of pathogens that cause sexually transmitted diseases (STDs). Examples of STDs of clinical importance and the references for the PCR-based detection are listed below. Nucleic acid analogs may be designed to have the sequence of specific PCR primer sequences, and can be used in combination in many of the embodiments of the invention described herein.

In one embodiment, the nucleic acid analogs are designed to have the sequences of primers used for PCR-based detection of chlamydia. Many such primers are known in the art (see, e.g., E. H. Koumans et al., J. CLIN. MICROBIOL. 41:1507-11 (2003); M. Puolakkainen et al., J. CLIN. MICROBIOL. 36:1489-93 (1998); F. Betsou et al., J. CLIN. MICROBIOL. 41:1274-6 (2003); J. Knox et al., SEX. TRANSM. DIS. 29:647-54 (2002); T. Mygind et al., BMC MICROBIOL. 2:17 (2002)).

In another embodiment, the nucleic acid analogs are designed to have the sequences of primers used for PCR-based detection of Treponema pallidum. Examples of primers used to identify Treponema pallidum by PCR based assays are known in the art (see, e.g., A. Centurion-Lara et al., J. CLIN. MICROBIOL. 35:1348-52 (1997); A. A. Martin et al., DIAGN. MICROBIOL. INFECT. DIS. 40:163-6 (2001); S. L. Orton et al., Prevalence of circulating Transfusion 42:94-9 (2002).

In another embodiment, the nucleic acid analogs are designed to have the sequences of primers used for PCR-based detection of HIV. Examples of primers used to identify HIV by PCR based assays are known in the art (see, e.g., L. Gibney et al., SEX TRANSM INFECT 77:344-50 (2001); A. Spinillo et al., BJOG 108:634-41 (2001)).

In a further embodiment, the nucleic acid analogs are designed to have the sequences of primers used for PCR-based detection of human papillomavirus (HPV). Examples of primers used to identify HPV by PCR-based assays are known in the art (see, e.g., R. L. Winer et al., AM. J. EPIDEMIOL. 157:218-26 (2003); J. E. Levi et al., J. CLIN. MICROBIOL. 40:3341-5 (2002); M. Skerlev et al., CLIN. DERMATOL. 20:173-8 (2002)).

In another embodiment, the nucleic acid analogs are designed to have the sequences of primers used for PCR-based detection of Neisseria gonorrhoeae. Examples of primers used to identify Neisseria gonorrhoeae by PCR based assays are known in the art (see, e.g., Mgone et al., SEX TRANSM DIS 29:775-9 (2002); J. P. Gomes et al., ACTA TROP 80:261-4 (2001); D. J. Diemert et al., J. CLIN. MICROBIOL. 40:4056-9 (2002)).

In another embodiment, the nucleic acid analogs are designed to have the sequences of primers used for PCR-based detection of genital herpes. Examples of primers used to identify genital herpes by PCR based assays are known in the art (see, e.g., M. H. Wolff et al., INTERVIROLOGY 45:20-3 (2002); A. Wald, CURR. CLIN. TOP. INFECT. DIS. 22:166-80 (2002); A. Scoular, SEX. TRANSM. INFECT. 78:160-5 (2002)).

The nucleic acid analogs may also be designed to have the sequences of primers used for PCR-based detection of Trichomonas vanginalis. Examples of primers used to identify Trichomonas vanginalis by PCR based assays are known in the art (see, e.g., K. A. Wendel et al., CLIN. INFECT. DIS. 35:576-80 (2002); K. A. Wendel et al., SEX TRANSM INFECT 79:151-153 (2003)).

Finally, the nucleic acid analogs may also be designed to detect general STDs. Examples of primers used to identify STDs by PCR based assays are known in the art (see, e.g., S. Mitrani-Rosenbaum et al., AM. J. OBSTET. GYNECOL. 171:784-90 (1994)).

H. Antibiotic Resistance

The methods, compositions, and assay systems may be used to detect the presence or change in expression of genes conferring antibiotic resistance. The target polynucleotide may correspond to genes that confer antibiotic resistance to a pathogen. Alternatively, the target polynucleotide may correspond to a gene in a host having an altered metabolism that may affect the efficacy of the antibiotic.

Examples of genes expressing antibiotic resistance can be found in the following references. Examples are provide but not limited to the examples provided. Genes encoding such as Beta Lactamases convey resistance to antibiotics including, but not limited to, penicillin, errythromycin, cefotaxime, ampicillin, piperacillin, cefoperazone, ceftazidime, cefepime, moxalactam, imipenem (see, e.g., D. M. Livermore, CLIN. MICROBIOL. REVIEWS 8:557-584 (1995); P. Hsuch et al., J. CLIN. MICROBIOL. 37:221-224 (1999); L. Setchanova et al., J. CLIN. MICROBIOL. 37:638-648 (1999); T. A. Wichelhaus et al., J. CLIN. MICROBIOL. 37:690-693 (1999); and G. A. Jacoby, EUR. J. CLIN. MICROBIOL. INFECT. DIS. 13:2-11 (1994)).

Other non-limiting examples of antibiotic confering genes include quinolones resistance genes, which convey resistance to antibiotics such as ceprofloxacin, ofloxacin, norfloxacin, enoxacin, sparfloxacin (see, e.g., E. E. C. Margerrison et al., J. BACTERIOL. 174:1596-1603 (1992); P. H. McWhinney et al., ANTIMICROB. AGENTS. CHEMOTHER. 37:2493-2495 (1993); and H. Yoshida et al., J. BACTERIOL. 172:6942-6949 (1990)).

Additional examples of antibiotic resistance genes include glycopeptide resistance genes, which convey resistance to antibiotics such as vancomycin and teicoplanin (see, e.g., C. H. Tremlett et al., J. CLIN. MICROBIOL. 37:818-820 (1999) and M. Arthur et al., GENE 154:87-92 (1995)) aminoglycoside resistance genes which convey resistance to antibiotics such as tobramycin, gentamicin, strepomycin, kanamycin, amikacin (M. Galimand et al., ANTIMICROB. AGENTS CHEMOTHER. 37:1456-1462 (1993); T. Lambert et al., ANTIMICROB. AGENTS CHEMOTHER. 38:702-706 (1994); and K. J. Shaw et al., ANTIMICROB. AGENTS CHEMOTHER. 37:708-714 (1993).

In some cases there are particular types of resistance that are of high concern. These include methicillin resistant Staphylococcus aureus (see, e.g., T. Ito et al., DRUG RESIST UPDATE 6:41-52 (2003); M. Kuroda et al., LANCET 357:1225-40 (2001); and R. A. Skurray et al., CIBA FOUND. SYMP. 207:167-83 (1997)).

Other antibiotic resistance conferring genes that may be detected include tuberculosis antibiotic resistance genes (see, e.g., I. Mokrousov et al., J. CLIN. MICROBIOL. 40:2509-12 (2002); G. Gong et al., DIAGN. CYTOPATHOL. 26:228-31 (2002); D. Garcia de Viedma et al., CLIN. MICROBIOL. 40:988-95 (2002)).

I. Genetic Screening for a Predisposition for Drug Responses

The methods, compositions, and assay systems may be used to detect genes conferring a predisposition to drug responses. The target polynucleotide may correspond to any polynucleotide sequence that confers a predisposition to the drug response. The target polynucleotide may correspond to sequences involved in predisposition to drugs that affect the cardiovascular system (see, e.g., C. Dudley et al., J. HYPERTENS. 14:259-62 (1996); P. R. Lima et al., BLOOD 90:2810-8 (1997); T. Sakaeda et al., PHARM. RES. 18:1400-4 (2001)). The target polynucleotide may also correspond to genes and other polynucleotide sequences implicated a predisposition to psychiatric drugs (see, e.g., D. Nikoloff et al., PHARMACOGENOMICS J. 2:400-7 (2002); L. Bertilsson et al., ACTA PSYCHIATR. SCAND. SUPPL. 391:14-21 (1997); S. Chen et al., CLIN. PHARMACOL. THER. 60:522-34 (1996)). The target polynucleotide may also correspond to gene sequences, or other polynucleotide sequences, corresponding to a predisposition to respond to analgesic drugs (see, e.g., M. J. Torres-Galvan et al., ANN. ALLERGY ASTHMA. IMMUNOL. 87:506-10 (2001)).

J. Genes Implicated in Effective Drug Response

The methods, compositions, and assays of the instant invention may be used in genetic testing is used a potential indication of a reaction to medication. The methods, compositions, and assays may be used to determine if a current treatment is working, or whether a resistance (or tolerance) is developing. Gene expression testing could be used to determine whether a tumor is becoming, or will become, resistant to a treatment. Gene based diagnostic testing may also includes pre-screening the likelihood of developing a disease or disorder in the future, pre-screening for genetic pre-disposition certain types of cancer, and identifying genetic polymorphisms.

Nucleic acid analogs may be designed to detect the presence and expression of specific genes. In one aspect, the methods may be used to determine the expression level of enzymes that can metabolize the associated drug. Polymorphic enzymes alter the effects of the drug and thus alter their ability to be used as a treatment. Genetic polymorphisms in the genes that influence the response of the associated drug, and thus affect the drugs ability to be used as a treatment, may be detected.

In one embodiment, nucleic acid analogs are designed to detect the sequences, or fragments of the sequences, encoding Cytochrome CYP2D6. Cytochrome CYP2D6 can metabolize Debrisoquin, which is used to treat antihypertension. Elevated expression of CYP2D6 indicates resistance to Debrisoquin (see, e.g., A. Mahgoub et al., LANCET 2:584-6 (1977); and A. Wennerholm et al., PHARMACOGENETICS 9:707-14 (1999)).

The presence or expression of Cytochrome CYP2D6 may be used to determine resistance to Sparteine, which is used to treat post-operative pain (see, e.g., M. Eichelbaum et al., EUR. J. CLIN. PHARMACOL. 16:183-7 (1979); F. Broly et al., PHARMACOGENETICS 5:373-84 (1995)).

The presence or expression of Cytochrome CYP2D6 may be used to determine resistance to Nortriptyline which is used to treat depression or cardiovascular disease (see, e.g., P. Dalen et al., CLIN. PHARMACOL. THER. 63:444-52 (1998); Q. Y. Yue et al., CLIN. PHARMACOL. THER. 64:384-90 (1998)).

The presence or expression of Cytochrome P459 may be used to determine altered codeine metabolism (see, e.g., S. H. Sindrup et al., Pharmacogenetics 5:335-46 (1995); 0. Mortimer et al., CLIN. PHARMACOL. THER. 47:27-35 (1990)).

In another embodiment, nucleic acid analogs are designed to detect the sequences, or fragments of the sequences, encoding Cytochrome CYP2C9. Cytochrome CYP2C9 can metabolize Warfarin which is used as an anticoagulant (see, e.g., G. P. Aithal et al., LANCET 353:717-9 (1999); R. Loebstein et al., CLIN. PHARMACOL. THER. 70:159-64 (2001)).

Cytochrome CYP2C9 can also metabolize Phenyloin, which is used to treat brain injury (see, e.g., J. van der Weide et al., PHARMACOGENETICS 11:287-91 (2001); R. Brandolese et al., CLIN. PHARMACOL. THER. 70:391-4 (2001)).

In addition, Cytochrome CYP2C19 can metabolize Omeprazole which I used to treat acid-reflux disease (see, e.g., J. D. Balian et al., CLIN. PHARMACOL. THER. 57:662-9 (1995); G. Tybring et al., CLIN. PHARMACOL. THER. 62:129-37 (1997)).

In a further embodiment, nucleic acid analogs are designed to detect the sequences, or fragments of the sequences, encoding dihydropyrimidine dehydrogenase. Dihydropyrimidine dehydrogenase can metabolize Fluorouracil, which is used to treat antineoplastic diseases (various cancer treatments) (see, e.g, M. Tuchman et al., N. ENGL. J. MED. 313:245-9 (1985); R. B. Diasio et al., J. CLIN. INVEST. 81:47-51 (1988)).

Nucleic acid analogs may also be designed to detect the sequences, or fragments of the sequences, encoding butyrylcholinesterase. Butyrylcholinesterase can metabolize Succinylcholine which is used as a muscle relaxant (see, e.g., O. Lockridge, PHARMACOL. THER. 47:35-60 (1990); and F. Ceppa et al., CLIN. CHEM. LAB. MED. 40:799-801 (2002).

Nucleic acid analogs may also be designed to detect the sequences, or fragments of the sequences, encoding N-Acetyltransferase 2. N-Acetyltransferase 2 can metabolize Isoniazid which is used to treat tuberculosis (see, e.g., Y. Furet et al., THERAPIE 57:427-31 (2002); T. Kita et al., BIOL. PHARM. BULL. 24:544-9 (2001); and Hiratsuka, M. Yakugaku Zasshi 122(7):451-63, (2002)).

N-Acetyltransferase 2 can also metabolize Hydralazine which is used to treat antihypertension (see, e.g., J. A. Timbrell et al. CLIN. PHARMACOL. THER. 28:350-5 (1980); and P. Zschieschang et al., PHARMACOGENETICS 12:559-63 (2002)).

N-Acetyltransferase 2 can metabolize Procainamide, which is used to treat antiarrhythmia (see, e.g., M. M. Reidenberg et al., CLIN. PHARMACOL. THER. 17:722-30 (1975); and D. Hickman et al., BIOCHEM. PHARMACOL. 50:697-703 (1995)).

In another aspect, nucleic acid analogs may also be designed to detect the sequences, or fragments of the sequences, encoding uridine disphosphate glucuronosyltransferase 1A1. Uridine disphosphate-glucuronosyltransferase 1A1 can metabolize Irinotecan which is used to treat colorectal cancer (see, e.g., L. Iyer et al., CLIN. PHARMACOL. THER. 65:576-82 (1999); Y. Ando et al., ANN. ONCOL. 9:845-7 (1998)).

Uridine disphosphate-glucuronosyltransferase 1A1 can also metabolize Bilirubin which is used to treat Gilbert's syndrome, a mild liver disorder (see, e.g., P. J. Bosma et al., N. ENGL. J. MED. 333:1171-5 (1995); Y. H. Kim et al., TAEHAN KAN HAKHOE CHI. 8:132-8 (2002)).

Nucleic acid analogs may also be designed to detect the sequences, or fragments of the sequences, encoding thiopurine S-methyltransferase. Thiopurine S-methyltransferase can metabolize Mercaptopurine which is used to treat Crohn's disease (see, e.g., R. M. Weinshilboum, XENOBIOTICA 22:1055-71 (1992); and A. Wennerholm et al., PHARMACOGENETICS 9:707-14 (1999)).

Thiopurine S-methyltransferase can also metabolize Azathioprine which is also used to treat Crohn's disease (see, e.g., B. A. Kaskas et al., GUT 52:140-2 (2003); and C. A. Marra et al., J. RHEUMATOL. 29:2507-12 (2002)).

Nucleic acid analogs may also be designed to detect the sequences, or fragments of the sequences, encoding catechol O-methyltransferase. Catechol O-methyltransferase can metabolize Levodopa, which is used to treat Parkinson's disease (see, e.g., D. K. Reilly et al. CLIN. PHARMACOL. THER. 28(2):278-86, (1980); and A. Wennerholm et al. PHARMACOGENETICS 9(6):707-14, (1999)).

Nucleic acid analogs may also be designed to detect the genetic polymorphisms associated with drug resistance. In one embodiment, the nucleic acid analogs may be designed to detect ACE polymorphisms which can influence the response of the ACE inhibitor antihypertensice, used to treat heart failure (see, e.g., P. Jacobsen et al., KIDNEY INT. 53:1002-6 (1998); M. Kohno et al., AM. J. MED. 106:544-9 (1999)).

ACE polymorphisms can also influence the response of Fluvastatin used to treat Coronary atherosclerosis (see, e.g., A. J. Marian et al., J. AM. COLL. CARDIOL. 35:89-95 (2000); Y. Bosse et al., CLIN. GENET. 62:45-52 (2002)).

In another embodiment, the nucleic acid analogs may be designed to detect Arachidonate 5-lipoxygenase polymorphisms, which can influence the response of Leukotriene inhibitors used as anti-inflammatories (see e.g. S. J. Fowler et al., EUR. J. CLIN. PHARMACOL. 58:187-90 (2002); and T. Koshino et al., MOL. CELL. BIOL. RES. COMMUN. 2:32-5 (1999)).

The nucleic acid analogs may be designed to detect B2-Adrenergic receptor polymorphisms which can influence the response of B2-Agonists used to treat asthma and pulmonary disease (see e.g. S. B. Liggett, AM. J. RESPIR. CRIT. CARE MED. 161:S197-201 (2000); V. Dishy et al., N. ENGL. J. MED. 345:1030-5 (2001).

The nucleic acid analogs may also be designed to detect Bradykinin B2 receptor polymorphisms which can influence the response of ACE-inhibitor used to treat heart failure (see e.g. S. Mukae et al., HYPERTENSION 36:127-31 (2000); S. Mukae et al., J. HUM. HYPERTENS. 16:857-63 (2002)).

The nucleic acid analogs may be designed to detect Dopamine receptors (D2, D3, D4) polymorphisms which can influence the response of Antipsychotics (see e.g. M. J. Arranz et al., LANCET 355:1615-6 (2000); V. S. Basile et al., NEUROPSYCHOPHARMACOLOGY 21:17-27 (1999)).

Nucleic acid analogs may also be designed to detect Estrogen receptor-a polymorphisms which can influence the response of Conjugated estrogens and are used in Hormone-replacement therapy for menopause, osteoporosis (see e.g. D. M. Herrington et al., N. ENGL. J. MED. 346:967-74 (2002); B. Ongphiphadhanakul et al., CLIN. ENDOCRINOL. (OXF.) 52:581-5 (2000)).

The nucleic acid analogs may also be designed to detect Glycoprotein nia subunit of glycoprotein IIb/IIIa polymorphisms, which can influence the response of Aspirin or glycoprotein IIb/IIIa inhibitors used to treat myocardial infarction (see e.g., A. D. Michelson et al., CIRCULATION 101:1013-8 (2000); G. Andrioli et al., BR. J. HAEMATOL. 110:911-8 (2000)).

In a further embodiment, the nucleic acid analogs may be designed to detect Serotonin(5-hydroxytryptamine) transporter polymorphisms which can influence the response of Antidepressants used to treat Alzheimer's disease and depression (see e.g. D. K. Kim et al., NEUROREPORT. 11:215-9 (2000); and E. Smeraldi et al., MOL. PSYCHIATRY 3:508-11 (1998)).

The nucleic acid analogs may be designed to detect addu-cin polymorphisms which can influence the response of Diuretics used to treat myocardial infarction, hypertension (see, e.g., M. T. Sciarrone et al., HYPERTENSION 41:398-403 (2003); B. M. Psaty et al., J. AMER. MED. ASSN. 287:1680-9 (2002)).

The nucleic acid analogs may further be designed to detect apolipoprotein E(APOE) polymorphisms which can influence the response of Statins used to treat coronary arterial disease, cholesterol, atherosclerosis (see, e.g., J. M. Ordovas et al., ATHEROSCLEROSIS 113:157-66 (1995); L. U. Gerdes et al., CIRCULATION 101: 1366-71 (2000)).

APOE polymorphisms which can influence the response of Tacrine used to treat Alzheimer's disease (see, e.g., J. Poirier et al., PROC. NATL. ACAD. SCI. U.S.A. 92:12260-4 (1995)); J. Poirier, MOL. DIAGN. 4:335-41 (1999); H. Soininen et al., NEUROSCI. LETT. 187:79-82 (1995)).

In another embodiment, the nucleic acid analogs may be designed to detect HLA polymorphisms which can influence the response of Abacavir used as an antiviral and to treat HIV (see, e.g., S. Mallal et al., LANCET 359:727-32 (2002); and S. Hetherington et al., LANCET 359:1121-2 (2002)).

The nucleic acid analogs may also be designed to detect Cholesterol ester transfer protein (CETP) polymorphisms which can influence the response of Statins used to treat coronary related disease, cholestrol, and atherosclerosis (see, e.g., J. A. Kuivenhoven et al., N. ENGL. J. MED. 338:86-93 (1998); P. Rump et al., NUTR. METAB. CARDIOVASC. DIS. 12:317-24 (2002); and F. V. van Venrooij et al., DIABETES CARE 26:1216-23 (2003)).

In another embodiment, the nucleic acid analogs may be designed to detect Ion Channel associated polymorphisms which can influence the response of Erythromycin, an antibiotic used to treat bacterial infections (see, e.g., F. Sesti et al. PROC. NATL. ACAD. SCI. USA 97:10613-8 (2000); G. W. Abbott et al., CELL 97:175-87 (1999)).

The nucleic acid analogs may further be designed to detect Methylguanine methyltransferase polymorphisms which can influence the response of Carmustine used to treat glioma (see, e.g., M. Esteller et al., N. ENGL. J. MED. 343:1350-4 (2000); S. L. Gerson, J. CLIN. ONCOL. 20:2388-99 (2002)).

Nucleic acid analogs may be designed to detect Parkin polymorphisms which can influence the response of Levodopa used to treat Parkinson's disease (see, e.g., C. B. Lucking et al., N. ENGL. J. MED. 342:1560-7 (2000); V. Bonifati et al., NEUROL. SCI. 22:51-2 (2001)).

Nucleic acid analogs may be designed to detect Prothrombin and factor V polymorphisms which can influence the response of oral contraceptives and indicate potential risk for development of thrombosis (see, e.g., J. Tassin et al., BRAIN 123:1112-21 (2000); I. Martinelli et al., N. ENGL. J. MED. 338:1793-7 (1998); and I. Martinelli et al., ARTERIOSCLER. THROMB. VASE. BIOL. 19:700-3 (1999)).

The nucleic acid analogs may also be designed to detect Stromelysin-1 polymorphisms which can influence the response of Statin used to treat atherosclerosis (see, e.g., C. Legnani et al., EUR. HEART J. 23:984-90 (2002); S. B. Liggett, AM. J. RESPIR. CRIT. CARE MED. 161: S197-201 (2000); S. E. Humphries et al., ATHEROSCLEROSIS 139:49-56 (1998)). S. Humphries et al. EUR. HEART J. 23:721-5, (2002); and M. P. de Maat et al., AM. J. CARDIOL. 83:852-6 (1999)).

K. Genetically Modified Organisms

The methods disclosed herein also provide a rapid and sensitive diagnostic test for the presence genetically modified organisms (GMOs). Examples of GMOs include, but are not limited to, organisms in which one or more genes have been modified, added, or deleted. GMOs may be characterized by the presence of one or more specific gene, absence of one or more specific genes, specific alteration, or altered expression of one or more specific genes. Nucleic acid analogs may be designed to complement target polynucleotides characteristic of the GMOs. The presence and number of GMOs may be measured using the methods of the reaction.

L. Non-Indigenous Fluora and Fauna

The methods disclosed herein also provide a rapid and sensitive diagnostic test for the presence and enumeration of non-indigenous fluora and fauna. Organisms that are not indigenous to a particular region present environmental and biological hazards to indigenous fluora and fauna. Nucleic acid analogs may be designed to complement target polynucleotides characteristic of the non-indigenous fluora and fauna. The presence and number of non-indigenous fluora and fauna may be measured using the methods of the reaction.

M. Agricultural Applications

The methods disclosed herein also provide a rapid and sensitive diagnostic test for the presence and enumeration of specific plants and plant varieties. Nucleic acid analogs may be designed to complement target polynucleotides characteristic of the specific plants or plant varieties. The presence and number of the plants and varieties may be measured using the methods of the reaction.

N. Veterinary Applications

The methods, compositions, and assays disclosed herein also provide a rapid and sensitive diagnostic test in veterinary applications. Nucleic acid analogs may be designed to complement target polynucleotides that correspond to animal based infections or to genetic diseases or disorders.

In one embodiment, the methods, compositions, and assays may be used to detect the presence of or infection by rabies virus. Nucleic acid analogs may be designed to have the sequences of primers used for PCR-based detection of rabies. Examples of primers used to identify rabies virus by PCR based assays are known in the art (see, e.g., M. Ito et al., J. CLIN. VIROL. 26:317-30 (2003); E. M. Black et al., J. VIROL. METHODS 105:25-35 (2002); D. David et al., VET. MICROBIOL. 87:111-8 (2002); M. Ito et al., J. VET. MED. SCI. 63:1309-13 (2001).

In another embodiment, the methods, compositions, and assays may be used to detect Porcine Stress Syndrome. Porcine Stress Syndrome is caused by a mutation of the ryanodine-receptor (RYR-1)-gene-homozygous or heterozygous. Nucleic acid analogs may be designed to have the sequences of primers used for PCR-based detection of Porcine Stress Syndrome. Examples of primers used to identify Porcine Stress Syndrome by PCR based assays are known in the art (see, e.g., S. H. Lee et al., ANIM. GENET. 33:237-9 (2002), H. Bu et al., ZHONGGUO XIU FU CHONG JIAN WAI KE ZA ZHI. 14:311-4 (2000).

The methods, compositions, and assays may be used to detect Hyperkalemic Periodic Paralysis Disease (HyPP). HyPP is a genetic disease in American Quarter horses or crossbreds. Data imply that HyPP is inherited as a codominant genetic defect, because the homozygotes showed more severe clinical signs of disease than heterozygotes. Nucleic acid analogs may be designed to have the sequences of primers used for PCR-based detection of HyPP.

In another embodiment, the methods, compositions, and assays may be used to detect FeCV (Feline Coronavirus). Nucleic acid analogs may be designed to have the sequences of primers used for PCR-based detection of Feline Coronavirus. Examples of primers used to identify Feline Coronavirus by PCR based assays are known in the art (see, e.g., M. Kennedy M et al., J. VET. DIAGN. INVEST. 14:520-2 (2002); D. D. Addie et al., VET. REC. 148:649-53 (2001); A. A. Herrewegh et al., VIROLOGY 234:349-63 (1997).

In another embodiment, the methods, compositions, and assays may be used to detect the presence of or infection by FIP virus, a mutant of the ubiquitous feline enteric coronavirus (FECV). Nucleic acid analogs may be designed to have the sequences of primers used for PCR-based detection of FIP virus. Examples of primers used to identify FIP virus by PCR based assays are known in the art (see, e.g., D. A. Gunn-Moore et al., VET. MICROBIOL. 62:193-205 (1998); M. Kennedy et al., VET. MICROBIOL. 81:227-34 (2001).

The methods, compositions, and assays may also be used to detect the presence of or infection by Equine infectious anemia virus (EIAV). Nucleic acid analogs may be designed to have the sequences of primers used for PCR-based detection of EIAV. Examples of primers used to identify EIAV by PCR based assays are known in the art (see, e.g., R. F. Cook et al., J. VIROL. METHODS 105:171-9 (2002); J. L. Langemeier et al., J. CLIN. MICROBIOL. 34:1481-7 (1996); M. M. Nagarajan et al., J. VIROL. METHODS 94:97-109.

The methods, compositions, and assays may also be used to detect the presence of or infection by *Brucella ovis*. Nucleic acid analogs may be designed to have the sequences of primers used for PCR-based detection of *Brucella ovis*. Examples of primers used to identify *Brucella ovis* by PCR based assays are known in the art (see, e.g., L. Manterola L et al., VET. MICROBIOL. 92:65-72 (2003); M. E. Hamdy et al., VET. J. 163:299-305 (2002); B. J. Bricker et al., J. CLIN. MICROBIOL. 32:2660-6 (1994).

The foregoing examples are only exemplary. Target polynucleotides may include polynucleotides corresponding to other antibiotic resistant conferring genes known in the art.

VIII. Kits

In one aspect, the present application provides a kit for detecting target polynucleotides. A kit may include one or more reagents useful in the present invention, for example, dyes, nucleic acid analogs, sources of light stimulus, buffers, standards used for controls, keys showing positives and negatives of control samples for interpreting reaction results. Optionally, one or more buffers are provided. Preferably the kit includes instructions for performing a method. The kits may further include suitable packaging of the respective compositions, instructions, and/or other optional components as disclosed below.

A. Dyes

The kits provided herein include one or more dyes.

The dyes can be provided in pre-packages amounts, or can be provided in a single tube from which aliquots can be apportioned.

The dyes may be further packaged in any suitable packaging for segregation from other components of the kit and to facilitate dispensing of the composition.

B. Nucleic Acid Analogs

The kits may also include one or more nucleic acid analogs.

The nucleic acid analog may be any nucleic acid analog, as described herein. In one embodiment, the nucleic acid analog is an LNA. In another embodiment, the nucleic acid analog is a PNA.

The nucleic acid analog may have any sequence that is complementary or fully complementary to a target nucleic acid sequence. The sequence may be any sequence known in the art. In one embodiment, the nucleic acid analog has a sequence disclosed herein.

The nucleic acid analog may be provided in any suitable container, and may be pre-aliquoted into usable amounts, or in a single tube to be apportioned. The container may be further packaged in any suitable packaging for segregation from other components of the kit and to facilitate dispensing of the cleansing composition. In another embodiment, two or more the nucleic acid analog sequences may be contained in the same package.

The kits may also include a vehicle to facilitate effective hybridization of the nucleic acid analog to the target polynucleotide, such as salmon sperm DNA.

C. Source of Light Stimulus

The kits may optionally further include a source of light stimulus. Non-limiting examples of light sources include the Sylvania Cool White T8-CW, General Electric T8-C50, and Fritz Aurora 50/50, a Sylvania dulux S9W CF9DS/blue, an Osram F9TT/50K, and LEDs including Hebei 520 PG0C, 540IB7C and the Xenon USHIO UXL-553 lamp.

D. Polynucleotide Manipulating Components

The kits may also include components used to manipulate polynucleotides, such as buffers, enzymes, columns, and other materials.

The buffers, enzymes, columns, and other materials can include those that are used to lyse cells or extract DNA or RNA from a cell. The buffers, enzymes, columns, and other materials can also include components used to manipulate polynucleotides, including DNA and RNA. Such components include, for example, those disclosed in Molecular Cloning: A Laboratory Manual, third edition (Sambrook et al., 2000) Cold Spring Harbor Press, or any other reference disclosed herein.

E. Instructions.

Kits may further include instructions for performing the methods described herein. Instructions may be included as a separate insert and/or as part of the packaging or container, e.g., as a label affixed to a container or as writing or other communication integrated as part of a container. The instructions may inform the user of methods for application and/or removal of the contents of the kit, precautions and methods concerning handling of materials, expected results, warnings concerning improper use, and the like.

F. Additional Optional Components of the Kits.

Kits may further contain components useful in the practicing the methods disclosed herein. Exemplary additional components include chemical-resistant disposal bags, tubes, diluent, gloves, scissors, marking pens and eye protection.

EXAMPLES

The following non-limiting examples serve to more fully describe the manner of using the above-described invention. It is understood that these examples in no way serve to limit the scope of this invention, but rather are presented for illustrative purposes.

All nucleic acid analog and DNA stock solutions in the following Examples were made in water unless otherwise noted. The stock dye was made in methanol or DMSO.

Example 1

Liquid-Based Assay System for Detection of PNA Polynucleotide Binding

The formation of a PNA/polynucleotide complex resulted in a color change of the indicator dye. Cauliflower mosaic virus 35S promoter DNA was used as the specific target polynucleotide. The dye was 3,3'-diethylthiacarbocyanine (Sigma, Milwaukee).

In a test tube, 15 µM PNA molecules complementary to cauliflower mosaic virus 35S promoter (35SPNA) was added to 5 µM 35S promoter DNA (35SDNA). The PNA sequence was CCCACCCACGAGG-LYS [SEQ ID NO:11]. 150 µM dye in 5 mM phosphate buffer, pH 7.5, was added. The 35SPNA, and dye, are present in excess in the system.

The color change indicated the presence of the polynucleotide.

The liquid based system was tested using 1 µl of 2.5 mM dye diluted in a 50 µl total volume of 5 mM $PO_4$ reaction buffer. The system and methods were tested and successful in the pH range of 4-10, however the system performed better in systems above the pH of 5. At time zero reactions across the 4-10 pH range looked nearly identical to each other but less vibrant than controls lacking the PNA/target polynucleotide hybrid. Upon exposure to light stimulus, the reactions began to become clear. Upon further exposure to light stimulus reactions with PNA/polynucleotide hybrid became completely clear at the same rate between pH 6-10. Reactions with PNA/polynucleotide hybrid from pH 4-5 had residual shades of pink.

A number of buffers at 10 mM concentrations have been used. Some of the buffers were tested with various pHs. $NaPO_4$ buffers were tested up to 0.5 M concentration. Buffers and salts which performed optimally include $NaPO_4$, $NaHSO_4$, $K_2HPO_4$, $K_2SO_4$, and $CaSO_4$. Buffers and salts which did not allow successful performance of the methods include Na Citrate, NaCl, $CaH_2PO_4$, $FeSO_4$, and $MgSO_4$. The method also may use pure water, 0.1% SDS, 0.1% Triton® X-100, 0.1% TWEEN® 20, 3% butanol, 10% methanol, 10% isopropanol, or 10% DMSO, 1× blood lysis buffer (0.15 M $NH_4Cl$, 10 mM $NaHCO_3$, 0.1 mM EDTA) pH 7.4 or sucrose lysis buffer (0.32 M sucrose, 10 mM Tris, 1% Triton® X-100, 5 mM $MgCl_2$).

Sodium phosphate buffer was tested at pH 4, 5, 5.5, 6, 7, 8, 9, 10. All other buffers were tested at pH 7.5. Sodium phosphate buffer pH 7 gave the fastest reaction.

300 target polynucleotides per microliter of reaction were detected. Concentrations of $1.5 \times 10^{14}$ target polynucleotides/reaction/50 µL; $10^8$ amplified target polynucleotides/reaction/50 µL were also detected.

Example 2

Determination of the Effect of PNA Molecules on PCR Reactions

This Example shows the effects of various PNA molecules on PCR reactions. The PCR components were as follows:

| Component | Volume | Final Concentration |
|---|---|---|
| Water | 38 µL | N/A |
| Upstream primer, 50 µM | 0.5 µL | 0.5 µM |
| Downstream primer, 50 µM | 0.5 µL | 0.5 µM |
| $MgCl_2$, 25 mM | 3 µL | 1.5 mM |
| 10× Reaction Buffer (Promega) | 5 µL | 1X |
| PCR Nucleotide Mix (Promega), 10 mM each dNTP | 1 µL | 800 µM |
| Taq DNA Polymerase in Storage Buffer B (Promega), 5 U/µL | 0.5 µL | 0.05 U/µL |
| BSA | 0.5 µL | 10 mg/mL |

The primer sequences were as follows:

| Primer | Primer Sequence |
|---|---|
| OI 17 | 5'GCTCCTACAAATGCCATCA [SEQ:12] |
| OI 18 | 5'GATAGTGGGATTGTGCGTCA [SEQ:13] |
| PNA | 5'CCCACCCACGAGGAACATC [SEQ: 14] |

Thermal cycler program (MJ Research PTC-200)

| | 95° for 1 minute |
|---|---|
| 42 cycles of: | |
| | 94° for 10 seconds |
| | 53° for 10 seconds |
| | 72° for 20 seconds |
| Hold at 4° | |

The following samples were analyzed by PCR to determine if PNA molecules inhibit PCR reactions;

1. 1 µL Bt/RR corn DNA (Bt/RR corn has been genetically modified))
2. 1 µl Bt/RR corn DNA, 1 µL PNA (100 mM)
3. 1 µl Bt/RR corn DNA, 5 µL PNA (100 mM)
4. 1 µL Water The PCR results were visualized using 2% TBEE agarose gel electrophoresis.

The following samples were analyzed to determine whether the presence of PNA inhibits PCR. In addition, the effects of PNA and methanol on PCR performance were determined.

1. 1 µL Bt/RR corn DNA
2. 1 µL Bt/RR corn DNA, 1 µL PNA (100 mM)
3. 1 µL BIRR corn DNA, 5 µL PNA (100 mM)
4. 1 µL Bt/RR corn DNA, 1 µL methanol
5. 1 µL Bt/RR corn DNA, 5 µL methanol
6. 1 µL Water The PCR results were visualized using 2% TBEE agarose gel electrophoresis.

The results indicate that PNA did not inhibit PCR when 1 µL PNA was added to the reaction (Tube 2). PNA did inhibit PCR when 5 µL PNA was added to the reaction (Tube 3). Methanol did not inhibit PCR when 1 µL PNA was added to the reaction (Tube 4). Methanol did inhibit PCR when 5 µL PNA was added to the reaction (Tube 5).

Example 3

The time course of light stimulated change in an optical property of 3,3'-diethylthiacarbocyanine iodide for different concentrations of DNA molecule was determined for a specific target polynucleotide sequence, and PNA sequence.

The target polynucleotide was 5' CTACGGGAGGCAG-CAGTG 3' [SEQ ID NO:2] and complementary the PNA molecule was CACTGCTGCCTCCCCGTAG-Lys [SEQ ID NO:1]. The target polynucleotide concentrations were those that are listed in the legend of FIG. 5. The PNA concentration was 14.4 pmole/reaction. The dye concentration was 6 nmole/reaction.

Figure 5:
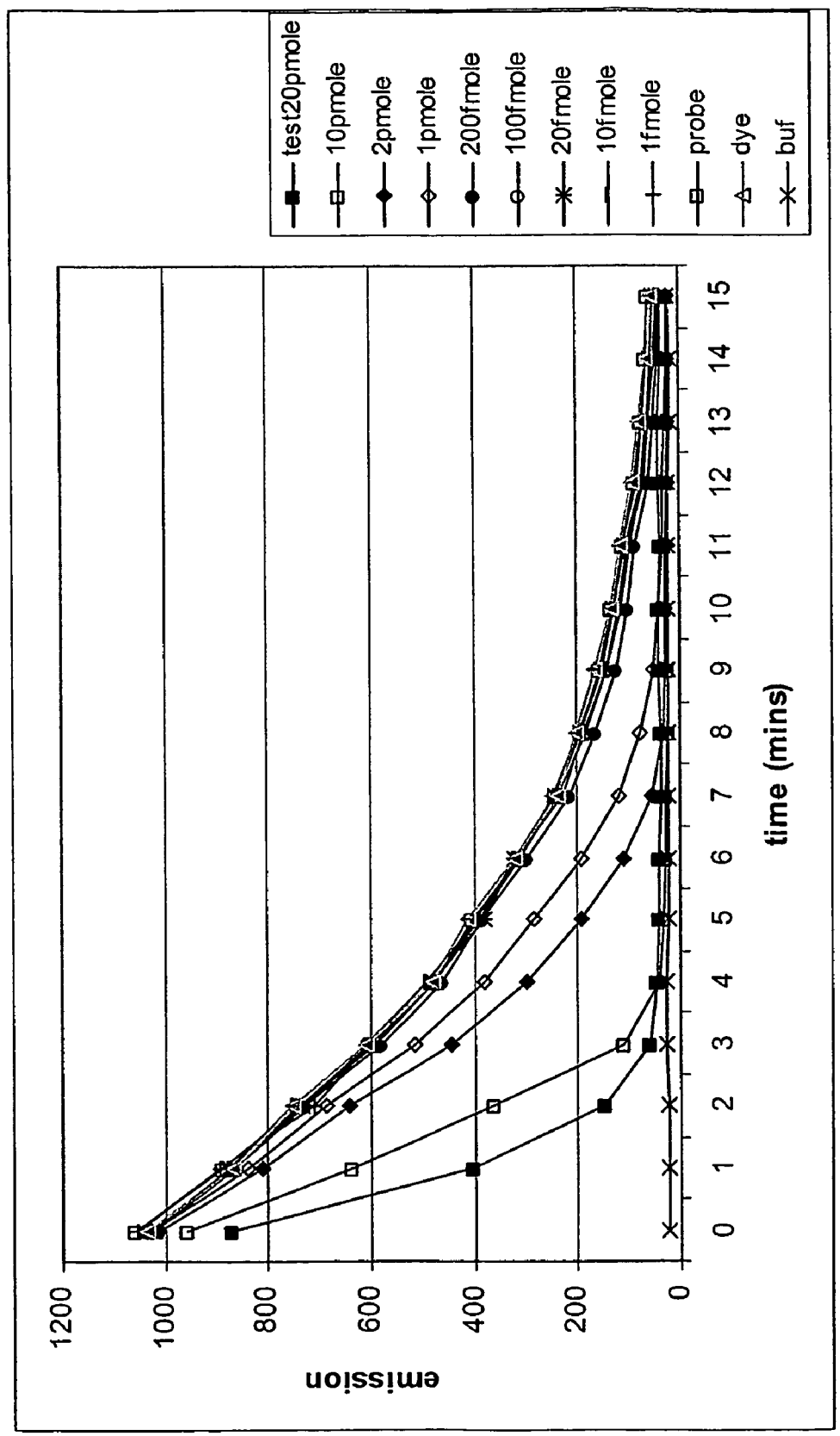
FIG. 5 depicts the time course of 3,3'-diethylthiacarbocyanine iodide dye emission after exposure to PNA and light stimulus for different concentrations of target polynucleotide.

FIG. 5 depicts the time course of 3,3'-diethylthiacarbocyanine iodide dye emission after exposure to light stimulus for different concentrations of DNA. Assay sensitivity with varying test DNA concentration using mixed wavelength light source to stimulate the change. Varying concentrations of polynucleotide (in this case, DNA) are depicted in the Figure legend. Legend represents the final DNA amount in each reaction. ( ) represents samples containing probe and dye only; (Δ) represents samples containing dye only; (x) represents samples containing buffer only.

Figure 6:
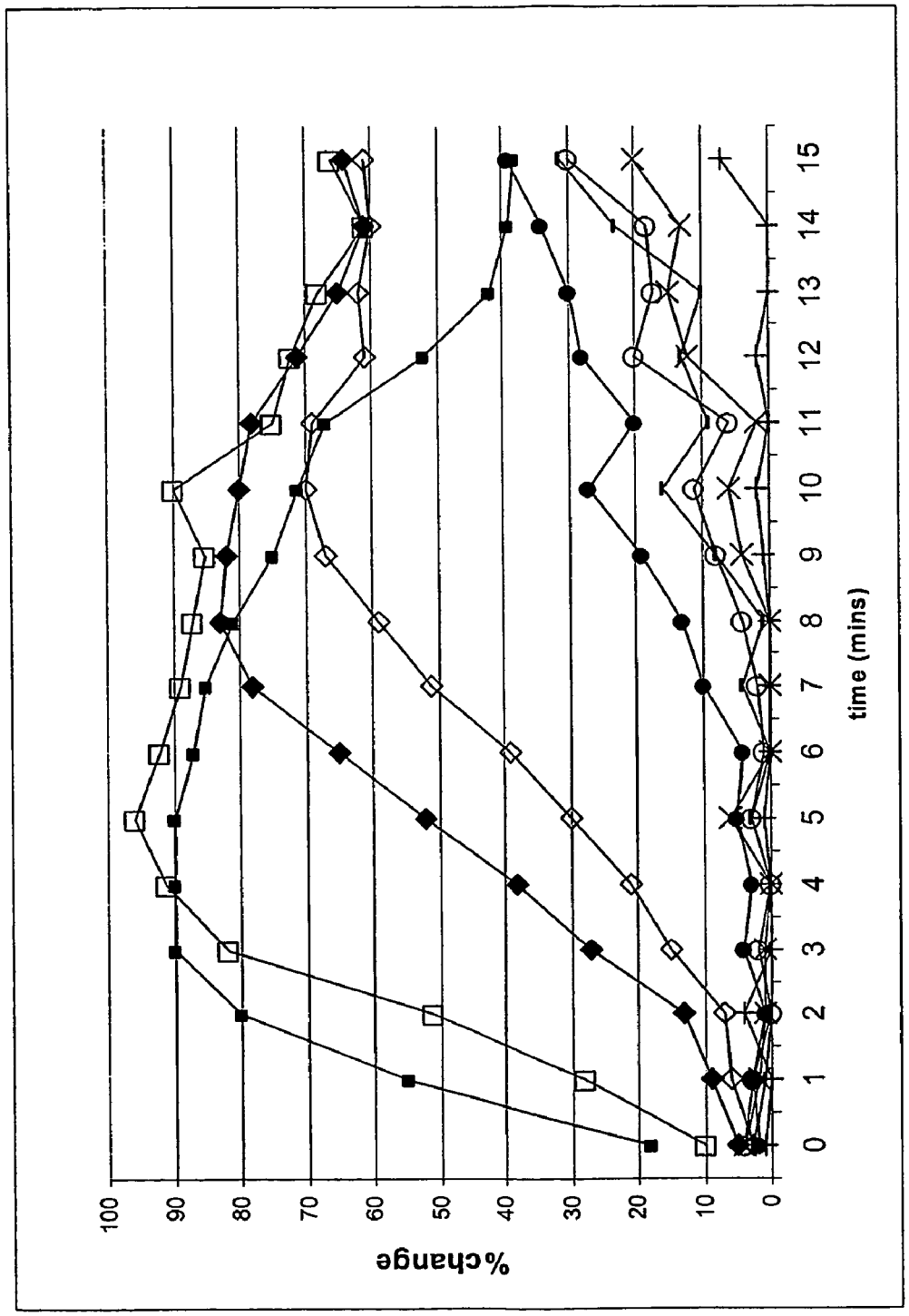
FIG. 6 depicts the percent change in 3,3'-diethylthiacarbocyanine iodide dye emission for different DNA concentrations.
Figure 10:
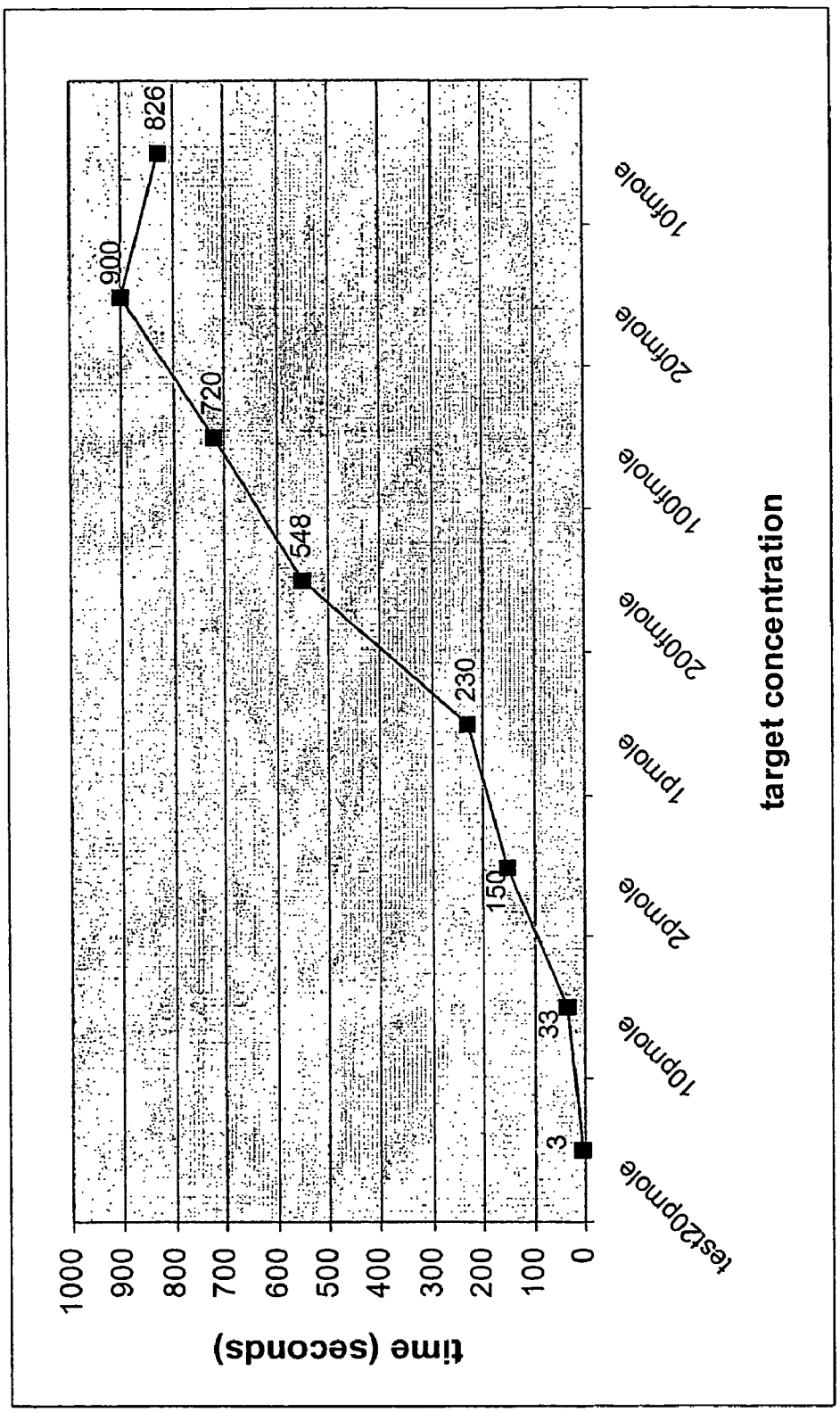
FIG. 10 depicts the time at which a 20% change in 3,3'-diethylthiacarbocyanine iodide emission occurs at different target polynucleotide concentrations.

FIG. 6 depicts the percent change in emission at different DNA concentrations. The dye had a higher rate of change of emission at higher DNA concentrations. By comparing the rate of change in an optical property of the dye at higher PNA concentrations to the rate of change in an optical property at lower PNA concentrations (or in the absence of PNA), the presence of the target polynucleotide was detected and could be quantitated as shown in FIG. 10. Polynucleotide concentrations are the same as depicted in the legend of FIG. 5.

Example 4

This example illustrates that rates of change in optical properties of dyes can differ for different wavelengths of light stimulus.

A target polynucleotide having the sequence 5' CTACGG-GAGGCAGCAGTG 3' [SEQ ID NO:2] at 20 pmole/reaction and the PNA molecule having the sequence CACTGCTGC-CTCCCCGTAG-Lys [SEQ ID NO:1] at 14.4 pmole/reaction were combined with 3,3'-diethylthiacarbocyanine iodide dye to form a mixture. The mixture was then exposed to the light stimulus produced by different light spectrum over 10 minutes, and the percent change in dye emission was measured over time.

Figure 7:
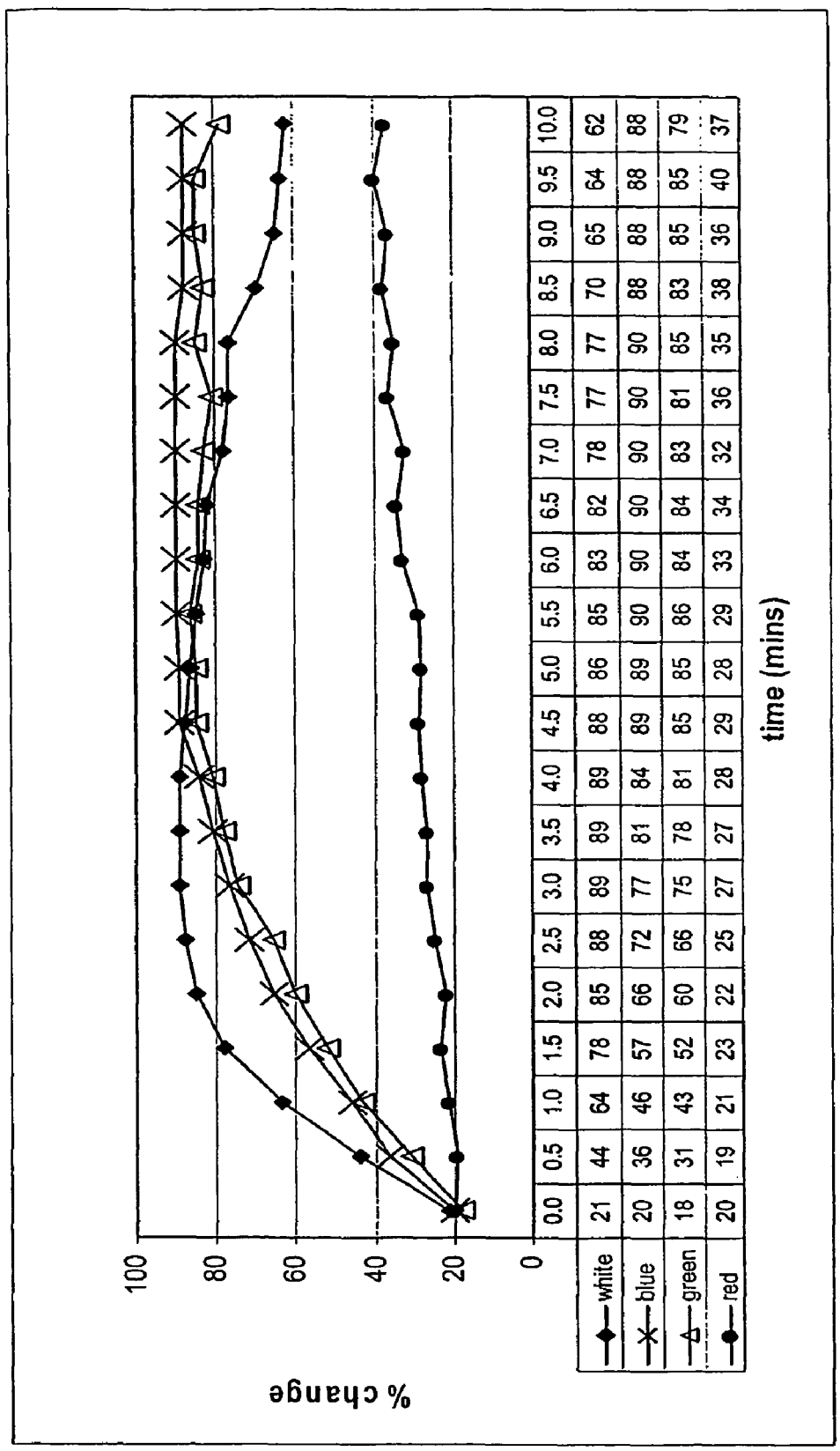
FIG. 7 compares the percent change in 3,3'-diethylthiacarbocyanine iodide emission in a test sample in which different wavelength ranges of light stimulus were used for stimulation.

FIG. 7 depicts the results of this experiment. White light stimulus was generated using the Fritz Aurora 50/50 bulb, and generated wavelengths from 350 nm to 700 nm. Blue light stimulus was generated using the Aurora bulb in conjunction with a blue filter with most light energy transmitted at a peak of approximately 460 nm. Green light stimulus was generated using the Aurora bulb in conjunction with a green filter with most light energy transmitted at a peak of approximately 510 nm. Red light stimulus was generated using the Aurora bulb in conjunction with a red filter with most light energy transmitted at a peak of approximately 620 nm.

White light stimulus resulted in the greatest percent change in emission. Blue and green wavelengths resulted in initially slower percent changes in emission. Red wavelengths showed a very slow percent change in emission.

Example 5

This Example demonstrates that the methods may also be used to detect differences in nucleic acid sequence.

Two samples were prepared. The first sample contained a mixture of PNA complementary to a GMO sequence found in GMO soy polynucleotide, GMO soy polynucleotide, and 3,3'-diethythiacarbocyanine iodide. The second sample contained a mixture of PNA complementary to a GMO sequence found in GMO soy polynucleotide, non-GMO soy polynucleotide, and 3,3'-diethylthiacarbocyanine iodide. Upon exposure to light stimulus, rate of change in emission over time was observed for both samples. The soy polynucleotides were obtained from soy leaf for both mixtures. In both mixtures, 1 µL of isolated DNA was used in a 100 µL reaction volume resulting in a DNA concentration of 0.25 ng/µL reaction.

Figure 8:
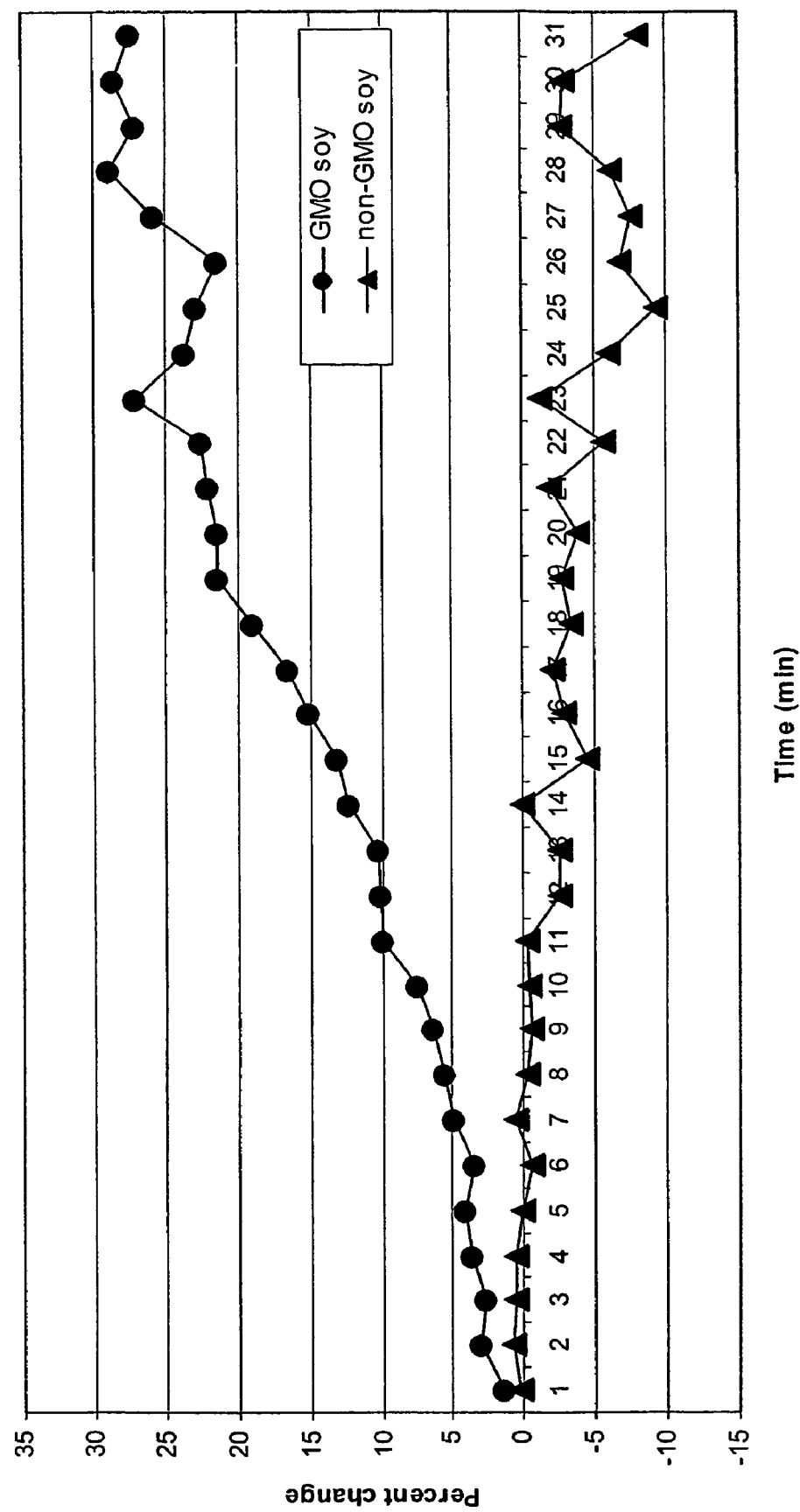
FIG. 8 compares the percent change in dye emission in a sample of DNA from GMO soy and DNA from non-GMO soy.

The resulting rate of change in emission over time is depicted in FIG. 8. The percent change in emission of 3,3'-diethythialcarbocyanine iodide was measured over time for a sample containing 3,3'-diethylthiacarbocyanine iodide, a PNA molecule complementary to a region of genetically modified organism (GMO) soy 35S polynucleotide, and either a genetically modified organism (GMO) soy polynucleotide or non-GMO polynucleotide. The change in emission of the dye results from the hybridization of the PNA to the GMO soy, and not to the non-GMO soy. The method detected the GMO soy, but not the non-GMO soy. The present methods provide means to detect differences in polynucleotide sequences present in DNA.

Example 6

This example shows that the quantity of polynucleotide in a sample may be determined by measuring the rate of change in an optical property of the dye in a sample having an unknown polynucleotide concentration and correlating the rate of change in the optical property to a curve of known rates of change in the optical property. The time may be fixed and the change may be measured at a particular time of reaction. The determination of the rate may also include determining the change in optical property at a single time and correlating the change in optical property to the concentration of one or more samples having a known concentration.

The time necessary for a 20% change in emission at a series of polynucleotide concentrations was calculated. The target polynucleotide sequence was 5' CTACGGGAGGCAG-CAGTG 3' [SEQ ID NO:2] and the PNA molecule sequence was CACTGCTGCCTCCCCGTAG-Lys [SEQ ID NO:1]. The time required for a 20% reduction as a function of target polynucleotide concentration is depicted in FIG. 10. The data correspond to the percent change data in FIG. 6. For one version of the assay, the point at which there is a 20% change in emission is measured for a sample having an unknown concentration. The quantity of polynucleotide in a given sample may be determined by extrapolating to a standard curve.

Example 7

This example demonstrates the target polynucleotide may be RNA.

A PNA, RNA, and 3,3'-diethylthiacarbocyanine iodide dye were combined. The target RNA sequence was 5' CUACGG-GAGGCAGCAGUG 3' [SEQ ID NO:15] and the PNA sequence was a universal bacterial PNA probe having the complementary sequence to the RNA sequence. The mixtures were exposed to light stimulus, and the percent change in emission of the dye over time was measured, and compared to a sample including a DNA polynucleotide sequence instead of an RNA polynucleotide sequence.

Figure 11:
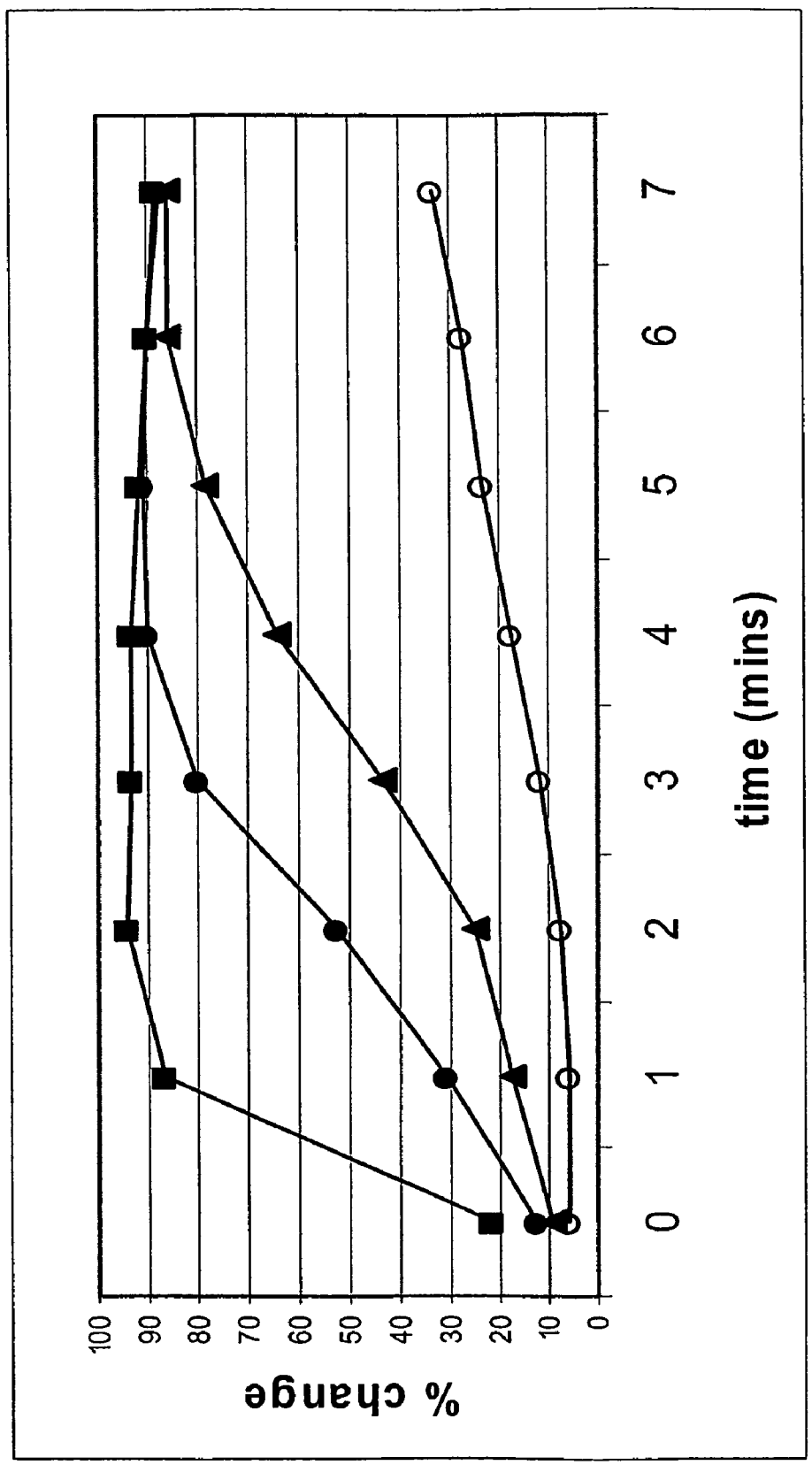
FIG. 11 depicts the percent change in dye emission in a sample of DNA and samples with varying concentrations of RNA.

The resulting percent change in the optical property over time is depicted in FIG. 11. Comparison of 20 pmole of target DNA per reaction (solid square), 20 pmole of target RNA per reaction (solid circle), 10 pmole/reaction of target RNA (solid triangle), and 2 pmole/reaction of target RNA (open circle). The Y-axis represents the percent change in fluorescence with time compared to probe and dye alone. RNA polynucleotides produced a change in emission of the dye over time. The presence of RNA was detected based on the rate of change in the optical property of the dye.

Example 8

This example demonstrates that the method works in the presence of a contaminating background.

The percent change in emission over time for 3,3'-diethylthiacarbocyanine iodide in a sample in a contaminating background of deli meat juices was determined. 3,3'-diethylthiacarbocyanine iodide dye, and a PNA molecule were prepared. The target polynucleotide sequence was 5' CTACGGGAGGCAGCAGTG 3' [SEQ ID NO:2] and the PNA sequence was CACTGCTGCCTCCCCGTAG-Lys [SEQ ID NO:1].

Figure 12:
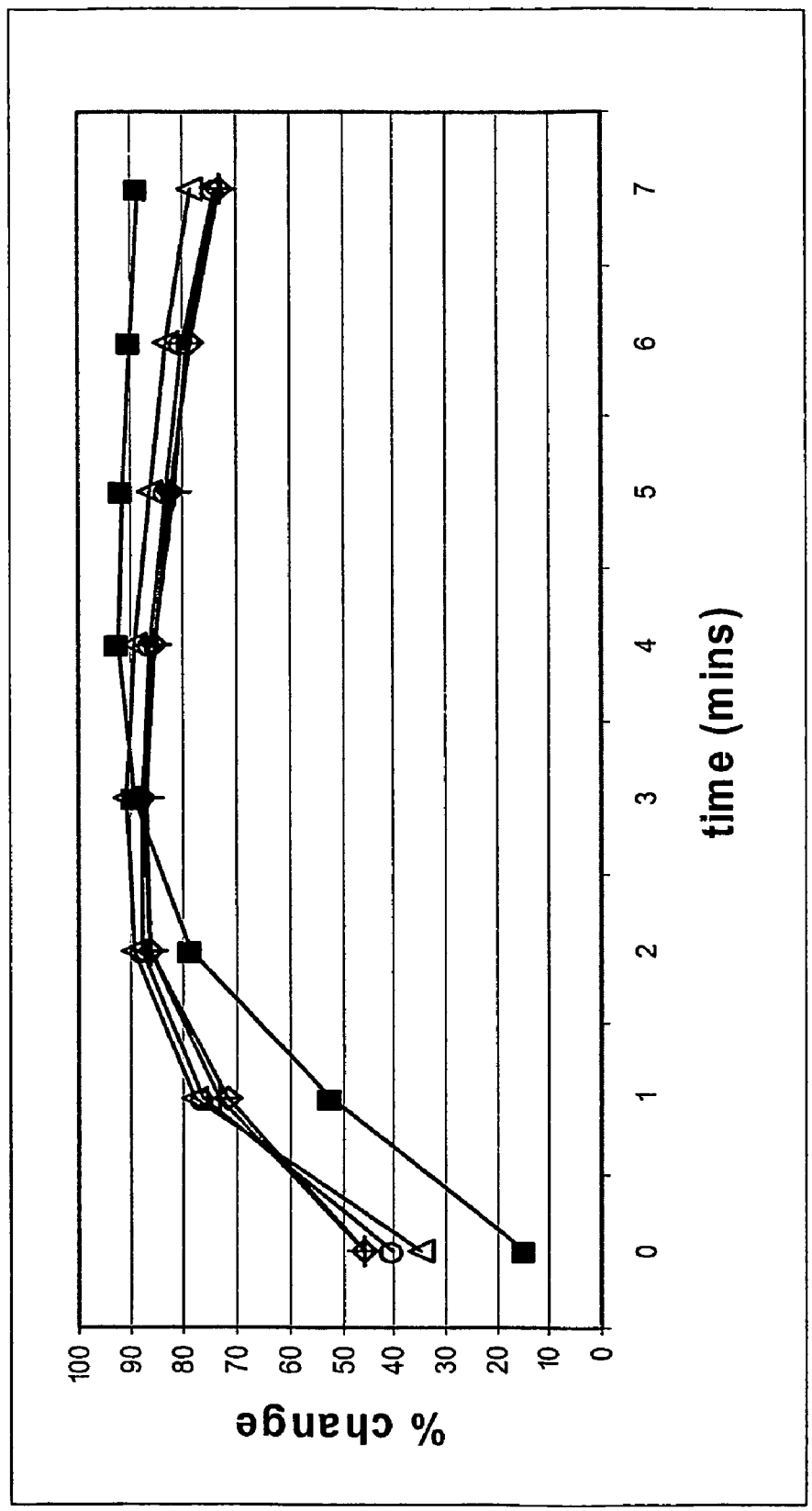
FIG. 12 compares the percent change in emission over time for 3,3'-diethylthiacarbocyanine iodide in a sample containing PNA and either DNA in the absence of a deli wash background or in the presence of deli wash background.

The results are depicted in FIG. 12. Percent changes in (■, solid square) an uncontaminated, clean system and in samples contaminated with background of 1 μL, 2 μL, and 4 μL (open symbols) of deli meat wash are depicted (open symbols). The example demonstrates that the presence of a polynucleotide was detected in a contaminated background.

Example 9

Figure 13:
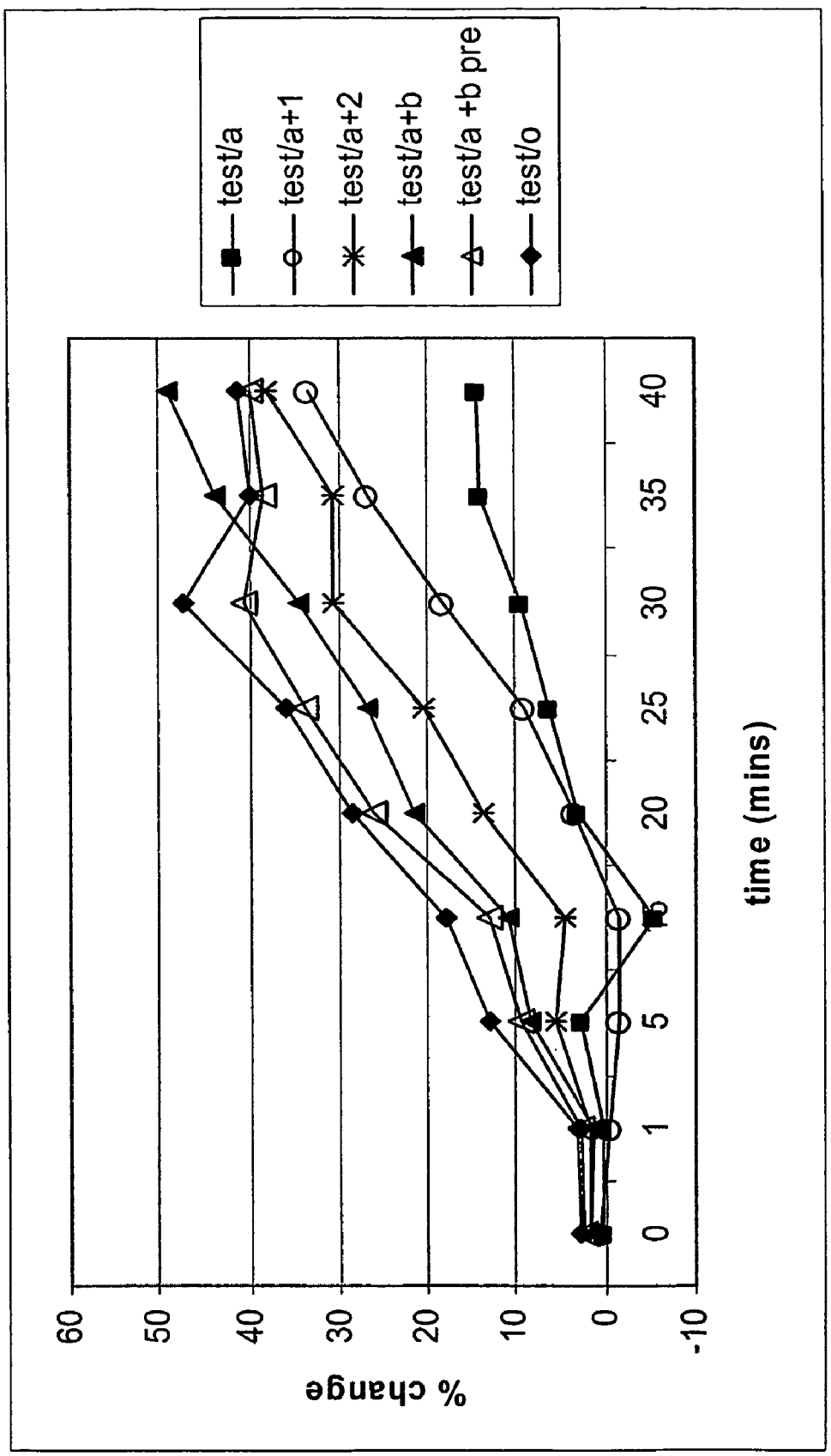
FIG. 13 depicts the addition of PNA "wedges".

FIG. 13 depicts the addition of PNA "wedges" in the system. Biotinylated PNA (5' bio-oo-gatagtgggattgtgcgt [SEQ ID NO:16]) is attached to a streptavidin well then reacted with a polynucleotide. After hybridization, the dye is added the system exposed to light stimulus and the percent change determined over time. The polynucleotide may be a synthesized polynucleotide or an amplicon polynucleotide. "Test a" represents 35S PNA 5' bio-oo-gatagtgggattgtgcgt [SEQ ID NO:16] and a 195 bp amplicon target polynucleotide. "Test a+1" includes both the 35S PNA 5' bio-oo-gatagtgggattgtgcgt [SEQ ID NO:16] with 195 bp amplicon target polynucleotide and PNA 5' tcacatcaatccact-LYS [SEQ ID NO:18]. "Test/a+2" includes 35S PNA 5' bio-oo-gatagtgggattgtgcgt [SEQ ID NO:16] with a 195 bp amplicon target polynucleotide and PNA 5' tcttcttttttccacg-LYS [SEQ ID NO:17]. "Test/a+b" includes 35S PNA 5' bio-oo-gatagtgggattgtgcgt [SEQ ID NO:16] with a 195 bp amplicon target polynucleotide, 5' tcttcttttttccacg-LYS [SEQ ID NO:17] and 5' tcacatcaatccact-LYS [SEQ ID NO:18]. "Test/a+b pre" includes 35S PNA 5' bio-oo-gatagtgggattgtgcgt [SEQ ID NO:16] with a 195 bp amplicon target polynucleotide, 5' tcttcttttttccacg-LYS [SEQ ID NO:17] and 5' tcacatcaatccact-LYS [SEQ ID NO:18] where 5' tcttcttttttccacg-LYS [SEQ ID NO:17] and 5' tcacatcaatccact-LYS [SEQ ID NO:18] are incubated with the amplicon target polynucleotide before hybridization with the attached PNA. "Test/o" represents 35S PNA 5' bio-oo-gatagtgggattgtgcgt [SEQ ID NO: 16] with a complementary polynucleotide. The linker-oo- was 8-amino-3,6-dioxaoctanoic acid. In this and other embodiments, linkers can be any chemical linking group known in the art. The addition of nucleic acid analogs to different sites on the target polynucleotide can alter the rate of change.

Example 10

This Example depicts the rate of change in an optical property of the dye when exposed to different wavelengths.

Figure 14:
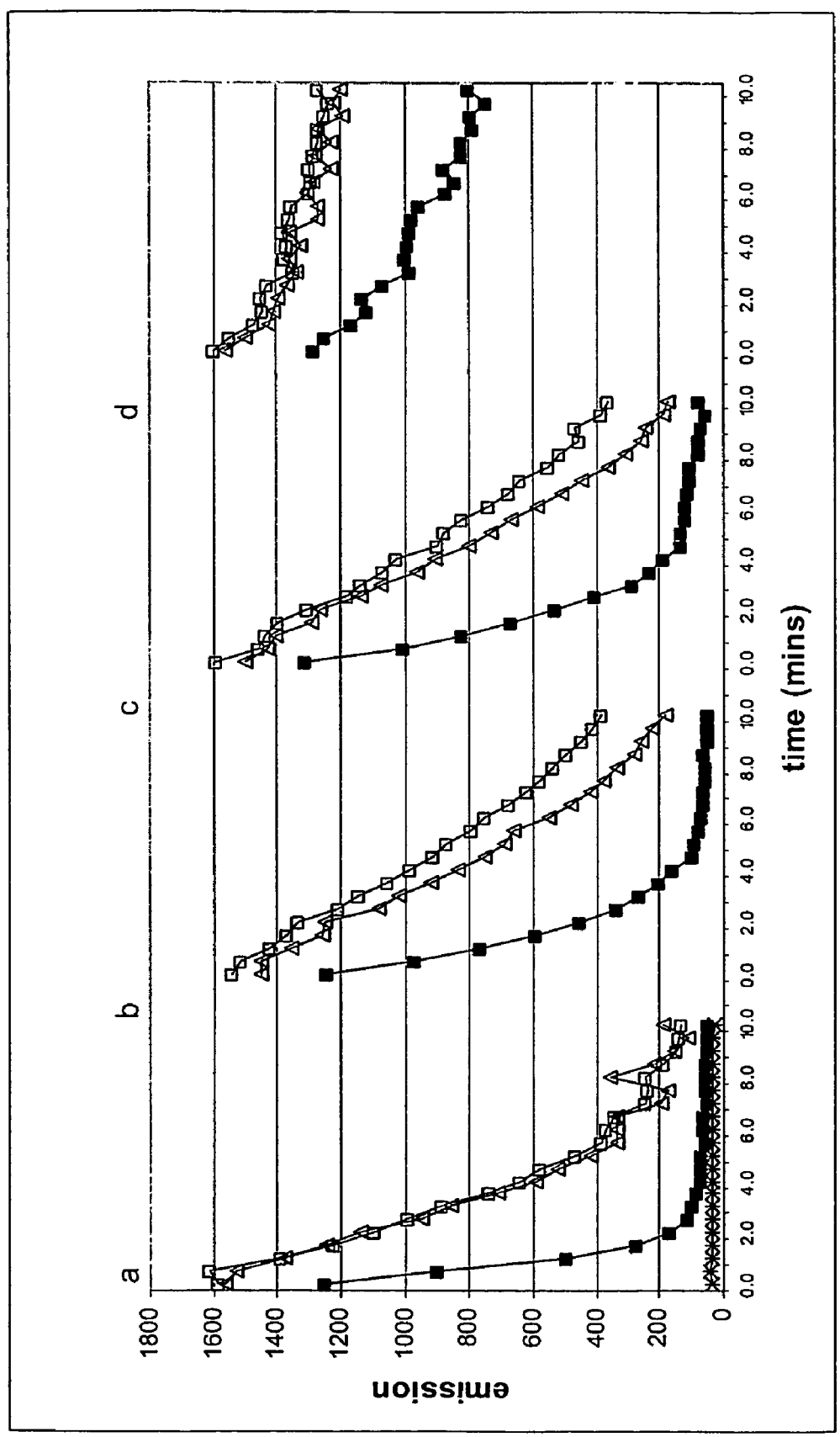
FIGS. 14A-D compares the emission after application of different lights with different peak wavelengths for a series of samples.

FIG. 14 depicts the comparison of exposure to light stimulus of different wavelengths for a series of samples. A mixture of target polynucleotide, PNA, and 3,3'-diethylthiacarbocyanine iodide dye was prepared, and a change in an optical property of the dye was observed. The target polynucleotide was 5' CTACGGGAGGCAGCAGTG 3' [SEQ ID NO:2] and the PNA molecule was CACTGCTGCCTCCCCGTAG-Lys [SEQ ID NO:1].

FIG. 14 a)-d) depict the dye emission over time at a series of wavelengths as follows: a) mixed light; b) mixed light through blue filter, 460 nm peak; c) mixed light through a green filter, 510 nm peak; d) mixed light through a red filter 720 nm peak. For each of a)-d), (■) depicts a positive control or test sample; (□) depicts the PNA probe only; (open triangle) depicts the 3,3'-diethylthiacarbocyanine iodide dye only; (x) depicts a buffer background. Percent change calculated from emission values is depicted in FIG. 7.

Example 11

This example shows that the methods may be used in a solid based format by preparing a PNA/polynucleotide hybrid either before or after binding to a solid support.

A universal bacterial PNA probe, and its complementary polynucleotide, were used in these experiments. The target polynucleotide was 5' CTACGGGAGGCAGCAGTG 3' [SEQ ID NO:2] and the PNA molecule was 5' bio-CACTGCTGCCTCCCCGTAG 3' [SEQ ID NO: 1]. In a first sample, a biotinylated PNA probe was immobilized to well by streptavidin-biotin binding. The polynucleotide and 3,3'-diethylthiacarbocyanine iodide dye were then added. The sample was exposed to light stimulus, and the percent change in fluorescent emission of the dye was measured.

In a second sample, a biotinylated probe and a target polynucleotide were allowed to hybridize together to form a PNA/polynucleotide hybrid. The PNA/polynucleotide hybrid was then added to a streptavidin-coated well, and the hybrid was allowed to bind to the well surface.

Figure 15:
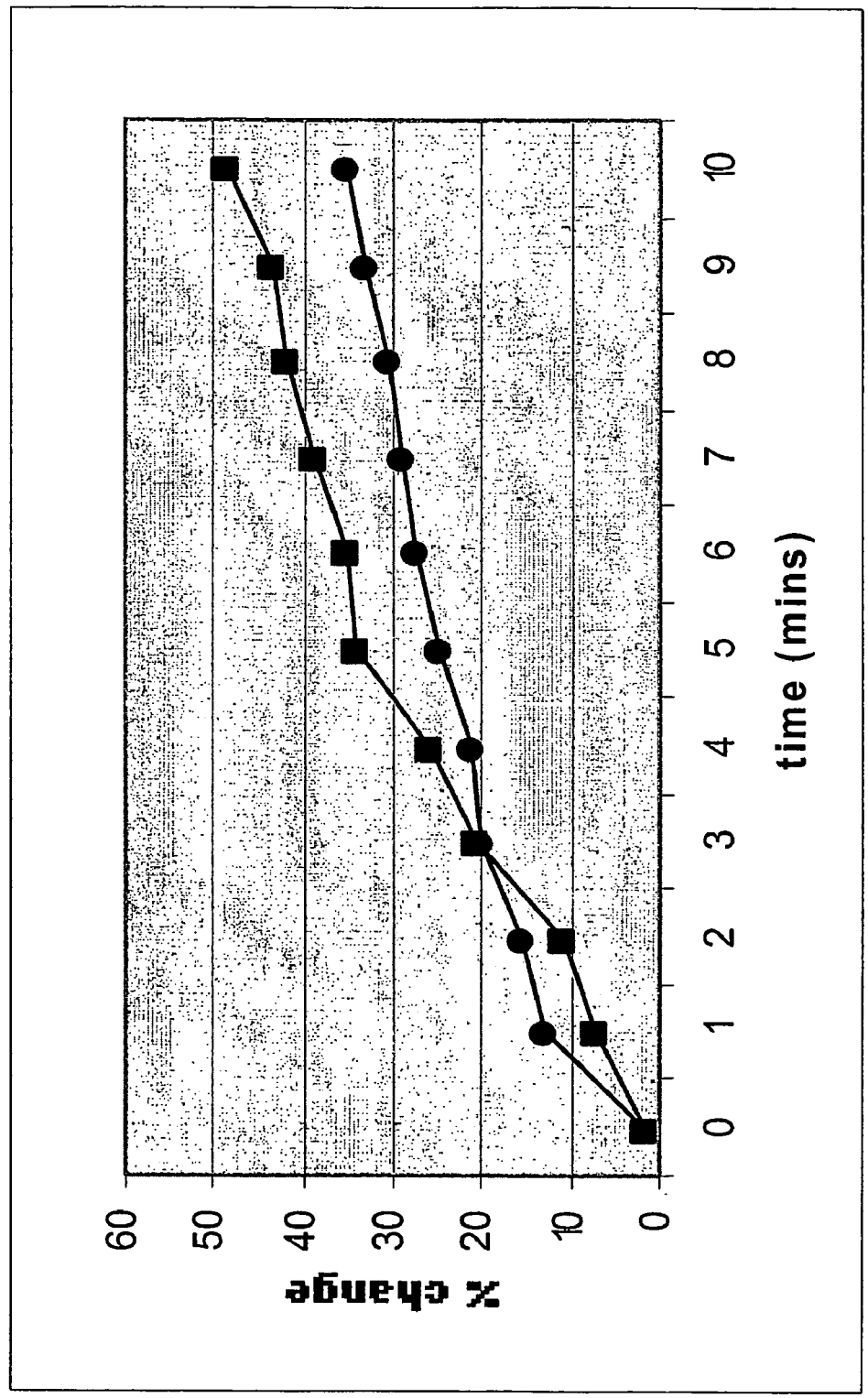
FIG. 15 depicts immobilized reactions over time using a universal bacteria PNA probe.

FIG. 15 depicts the percent change in emission over time observed in the first and second samples. In test 1 (■), the probe-bio immobilized to well by streptavidin-biotin binding before reacting to the target DNA and dye. In test 2 (●), the PNA molecule and target was allowed to hybridize together in solution before adding to the well. Y-axis represents the percent change in fluorescence with time compared to probe alone.

Example 12

This example demonstrates that the methods may be used to identify and/or quantify a target polynucleotide obtained from a blood sample.

Human blood was collected into EDTA tubes by venipuncture. 10 µL of male blood and 10 µL of female blood were added into a microfuge tube containing 180 µL of lysis buffer that was 6 M guanidinium thiocyanate; 20 mM EDTA; 10 mM Tris-HCl (pH 6.5); 40 g/L Triton® X-100; 10 g/L dithiothreitol. Prior to its addition to the blood the buffer was heated at 60° C. until dissolved. 10 µL of female blood was added into a microfuge tube containing 190 µL of the same lysis buffer. The reactions were allowed to incubate at room temperature for 10 minutes.

The reactions were centrifuged for 5 mins at 4000 rpm. Supernatant was discarded, and the pellet and wash with 500 µL of the lysis buffer. The pellet was centrifuged again for 2 mins at max speed. The supernatant was discarded, and the supernatant was washed with 500 µL of wash buffer (25% ethanol; 25% isopropanol; 100 mM NaCl; 10 mM Tris-HCl (pH 8.0)). The reactions were centrifuged for 2 mins at maximum speed, and the supernatant was discarded. The reactions were washed twice with 5 mM phosphate buffer used in the PNA hybridization reaction. After the final rinse, reactions were resuspended with 200 µL of 5 mM phosphate buffer.

The following table shows the test conditions for reaction in microwell. 2.5 µL of whole blood was used in a 50 µL reaction volume. This equates to 300 targets/µL of reaction and 100 ng of DNA total. PNA sequence 5' Bio-OO-TGAGTGTGTGGCTITCG 3' [SEQ ID NO:19].

|  | Test | Neg control | No PNA control |
|---|---|---|---|
| Sample | 48 µL of test | 48 µL of negative | 48 µL of negative |
| PNA | 1 µL | 1 µL | 0 |
| Dye | 1 µL | 1 µL | 1 µL |

Emission data was collected using a Genios spectrophotometer at an excitation wavelength of 535 nm and an emission wavelength of 590 nm. After an initial zero minute read, the samples were exposed to light stimulus from the Aurora 50/50 for 30 seconds. The fluorescence was measured every 30 seconds for 10 minutes.

Figure 16:
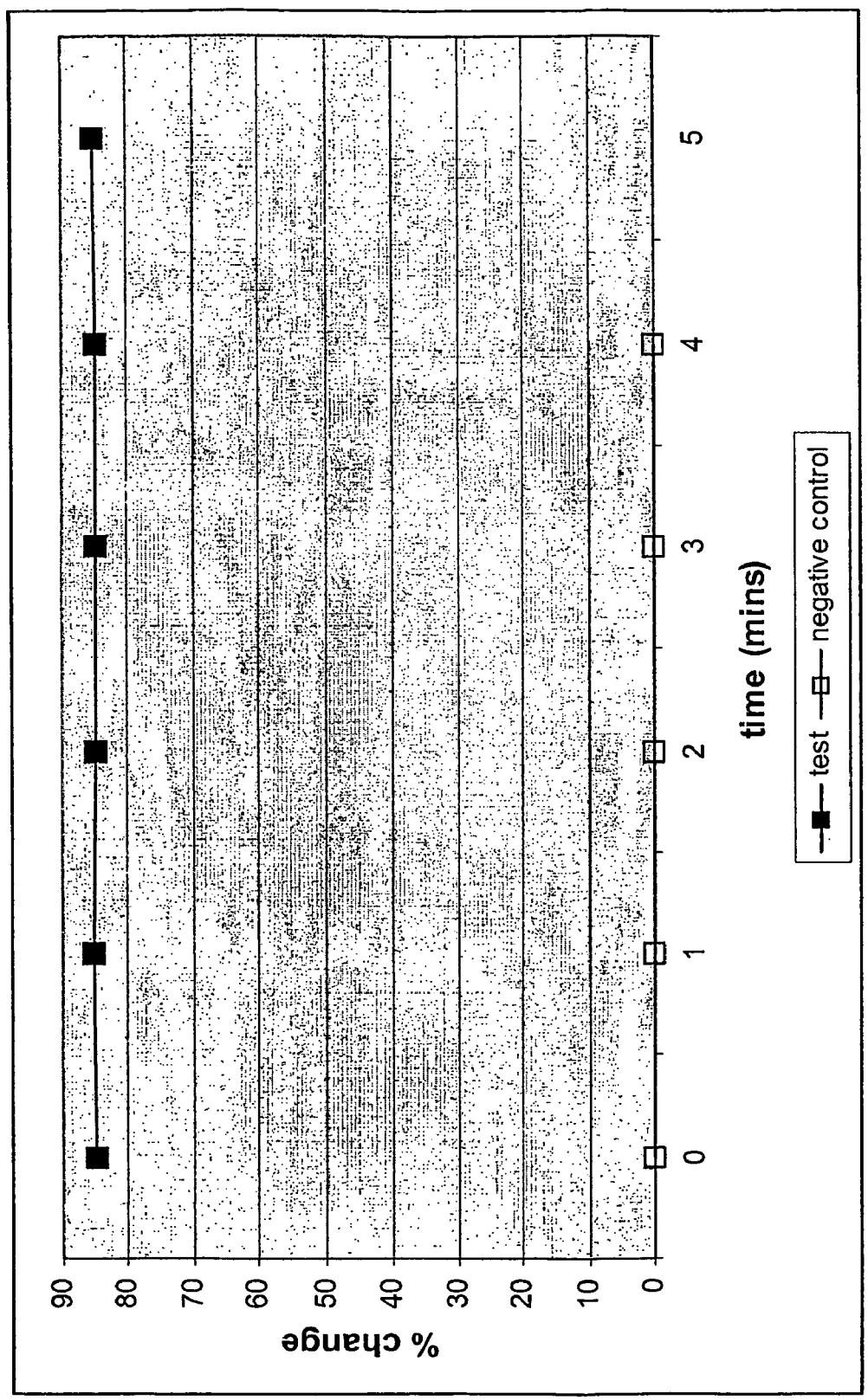
FIG. 16 depicts human SRY detection.

FIG. 16 shows that the sample of target male blood, depicted by (■), was detected by the assay, but the female blood depicted by (□) as a negative control was not detected.

Example 14

A number of nucleic acid sequences were or can be used to detect target polynucleotides. These sequences are listed below.

| PNA name | Seq | |
|---|---|---|
| PPI2101bio | 5' bio-oo-tgagtgtgtggctttcg [SEQ ID NO:19] | huSRY |
| PPI2024 | 5' cactgctgcctcccgtag-LYS [SEQ ID NO:1] | 16S |
| PPI2024bio | 5' bio-OO-actgctgcctcccgtag [SEQ ID NO:20] | |
| PPI2025bio4 | 5' bio-OOOO-tgcctcccgtag [SEQ ID NO:21] | |
| PPI2025bio6 | 5' bio-OOOOOO-tgcctcccgta [SEQ ID NO:22] | |
| PPI2025bio8 | 5' bio-OOOOOOOO-tgcctcccgta [SEQ ID NO:22] | |
| PPI2025bio10 | 5' bio-OOOOOOOOOO-tgcctcccgtag [SEQ ID NO:21] | |
| PPI2025 UL | 5' tgcctcccgtag [SEQ ID NO:21] | |
| PPI18bio | 5' bio-oo-gatagtgggattgtgcgt [SEQ ID NO:16] | 35S |
| PPI359 | 5' cccacccacgagg-LYS [SEQ ID NO:11] | |
| PPI485 | 5' tcttcttttttccacg-LYS [SEQ ID NO:17] | |
| PPI486 | 5'tcacatcaatccact-LYS [SEQ ID NO:18] | |
| PPI2202 | bio-(O)$_{10}$-ctcattgatggt [SEQ ID NO:23] | HIV |
| PPI911 | bio-(O)$_{10}$-cgcagaccacta [SEQ ID NO:24] | HCV |

Example 15

Figure 19:
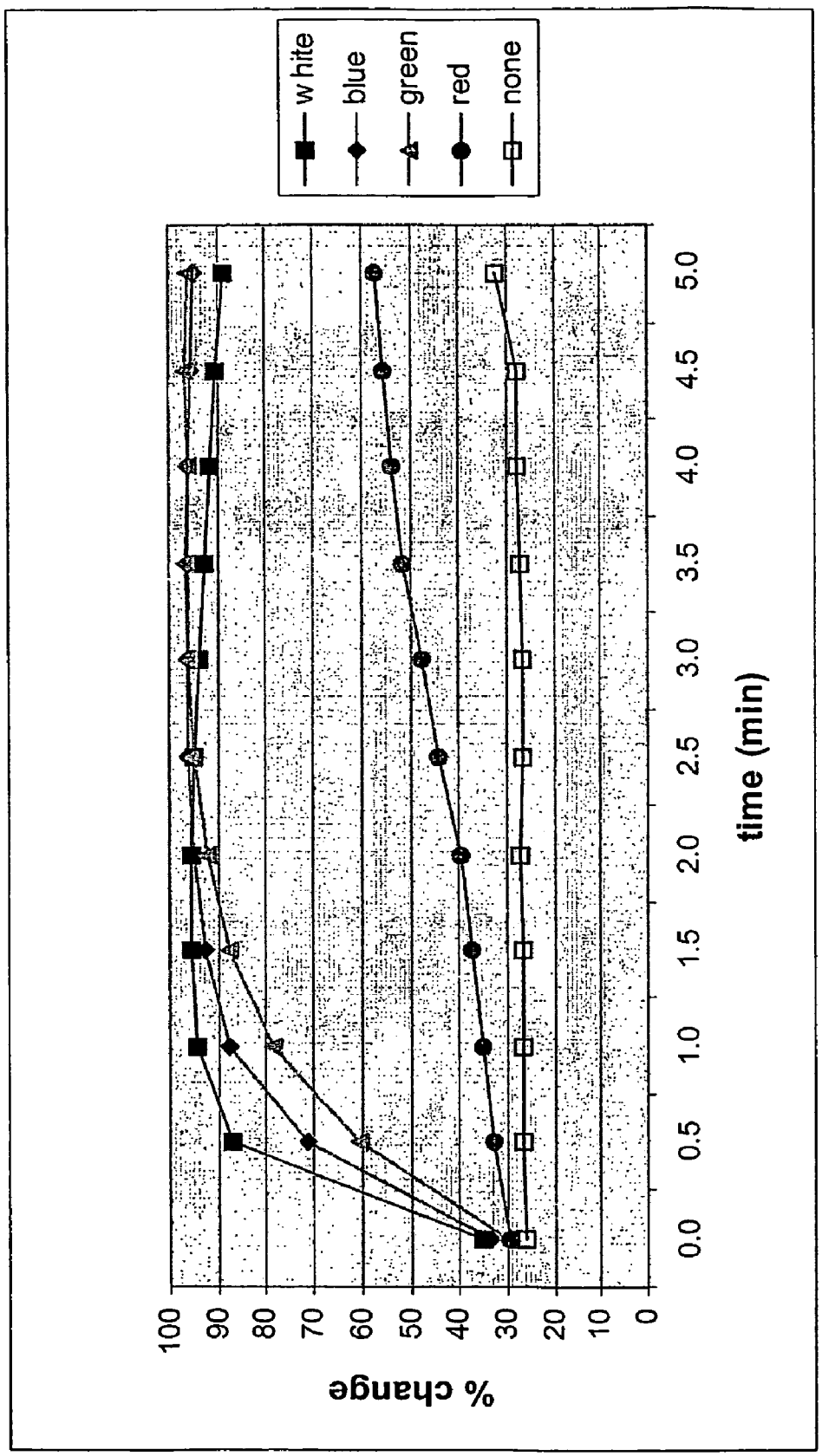
FIG. 19 depicts the effect of light stimulus with different peak wavelengths.

FIG. 19 depicts the effect of exposure to different wavelengths of light stimulus.

A mixture including 16S PNA (5' cactgctgcctcccgtag-LYS) [SEQ ID NO: 1], a polynucleotide (5' ctacgggaggcagcagtg) [SEQ ID NO:2], and 3,3'-diethylthiacarbocyanine iodide dye were exposed to a white light stimulus having all visible wavelengths, a blue light source (peak light energy transmission 460 nm), green light source (peak light energy transmission 510 nm), a red light source (peak light energy transmission 720 nm), and no light stimulus exposure. Light source for the mixed light was an Aurora 50/50 from FITZ. For the light sources blue, green or red, filters were placed on the Aurora 50/50. Reading was done on a Safire multiwell plate reader (produced by Tecan).

Mixtures exposed to light stimulus resulted in a different rate of change in an optical property of the dye compared to a reference value. Mixtures that were not exposed to light stimulus resulted in no measurable change over the time measurement. Different wavelengths resulted in different rates of change in optical properties. This example shows that light radiation may be used to cause different rates of change in an optical property of a dye.

Example 16

The PNA was immobilized on a solid substrate, and the amount of DNA was detected based on the change in rate of fluorescence of a dye.

The following reactants were used in this example: a) 10 µM probe-BIO (from Example 14); b) 2 mM dye Diethylthiacarbocyanine iodide (100 mM stock in DMSO; 2 mM working concentration in 5 mM buffer); c) 5 mM buffer (pH 5.5) (1 mL of 100 mM $Na_2HPO_4.7H_2O$+24 mL of 100 mM Na$_2$H$_2$PO$_4$.H$_2$O+475 mL H$_2$O pH to 5.5); d) 1×PBS+0.05% TWEEN® 20 (PBST) (1×PBS=0.137 M NaCl+2.68 mM KCl+4.3 mM NaH$_2$PO$_4$+1.47 mM KH$_2$PO$_4$); e) Streptavidin microtiter plates (NUNC); and f) test samples containing or lacking a target polynucleotide.

The number of wells was calculated. Each well was prepared by pre-washing wells 3× with 200 µL 1×PBST. 1 µL of PNA probe was used in 50 µL total reaction. 3 µL of probe was added to 147 µL PBST.

The PNA probes were attached to the solid surface of microtiter wells. The mixture was incubated 1 hour at room temperature shaking gently.

| +control | Test sample | Probe only | Buffer only |
|---|---|---|---|
| 50 µL | 50 µL | 50 µL | 50 µL buffer |

The wells were then washed 3× with 100 µL of PBST. The liquid was removed. The wells were then washed 3× with 5 mM phosphate buffer. For a positive control, 1 µL of the reaction was added in 49 µL of 5 mM phosphate buffer, then added to the positive control well. 1 µL of the sample was diluted in 49 µL of phosphate buffer then added to the test sample well. To probe and buffer only wells, 50 µL of phosphate buffer was added. All wells were incubated for 30 minutes at room temperature with gentle shaking. The wells were washed 5× with 100 µL of phosphate buffer as described above.

A dye solution was made by using 1 µL of 2 mM dye to 49 µL of phosphate buffer/well. The dye solution was added to all wells except the negative control buffer only well. 50 µL of phosphate buffer was added to the buffer only well.

The fluorescence of the dye was observed. An initial fluorescence reading was detected prior to providing exposure to light stimulus from an Aurora 50/50 light source. Excitation was at 535 nm and emission at 590 nm was observed every 2 minutes using a Genios multiwell plate reader.

Example 17

A. The following protocol was followed using a liquid PNA sample.

Sufficient wells for the number of samples to be tested plus 3 for controls were prepared. The DNA or RNA was isolated.

Each test reaction contained: 1 µL PNA probe, 47 µL buffer (5 mM 2 mL 100 mM Na$_2$HPO$_4$.7H$_2$O+48 mL NaH$_2$PO$_4$.H$_2$O/L (pH 5.5)), and 1 µL test sample. The samples were loaded into a Greiner 96-well strip plates (#705070).

The probe, dye and buffer were combined to form a mixture, and the wells were set up as follows:

| +control | Test sample | PNA only | Buffer only |
|---|---|---|---|
| 1 µL + control | 1 µL sample | 1 µL buffer | 50 µL buffer |

49 µL of the mixture was added to all wells EXCEPT buffer only well. The solution was gently mixed.

The absorbance or fluorescence without exposure to a light stimulus was determined at the following wavelengths: absorbance: 562 nm; fluorescence emission: 590 nm; and fluorescence excitation 535 nm.

The samples were exposed to light stimulus using an Aurora 50/50 and the absorbance or fluorescence was determined after every 30 seconds of exposure to a light stimulus.

B. The following protocol was conducted using PNA molecules that were immobilized on a solid surface.

The following items were used in the protocol: a) 10 µM PNA (ABI); b) 2 mM 3,3'-diethylthiacarbocyanine iodide (Sigma-Aldrich, catalog #173738) dye; c) 5 mM 1×PBS (0.137 M NaCl, 2.68 mM KCl, 4.3 mM NaH$_2$PO$_4$, 1.47 mM KH$_2$PO$_4$)+0.05% TWEEN® 20; d) 1×PBS (0.137 M NaCl, 2.68 mM KCl, 4.3 mM NaH$_2$PO$_4$) 1.47 mM KH$_2$PO$_4$)+ 0.05% TWEEN® 20; e) test samples including a target polynucleotide; and f) Streptavidin-coated plates (Nuncbrand Immobilizer™ (Catalog No. 436014)).

In one variation, the PNA was immobilized before introducing the polynucleotide samples. Enough wells were prepared for samples (n) to be tested plus 3 extra wells for controls by washing 3× with 300 µL of 1×PBST. The DNA or RNA to be tested was isolated. The biotinylated PNA was immobilized to the streptavidin-coated wells by adding 1 µL of 10 µM PNA stock into 49 µL of PBST.

A PNA master mix was made that included (n+2) (where "n" is the number of wells) times 1 µL of a 2 mM PNA stock, and (n+2)×49 µL of PBST. 50 µL of PNA mix was then added to all wells EXCEPT buffer only well.

The mixture was covered and incubated for 1 hour at room temperature on a gentle shaker.

Each well was washed 3× with 200 µL of PBST, then 3× with 5 mM phosphate buffer, and the nucleic acid samples were added to the immobilized probe. 1 µL of sample was added to 49 µL of 5 mM phosphate buffer.

Wells were prepared as diagramed below:

| | Test | +control | PNA only | Buffer only |
|---|---|---|---|---|
| Test sample | 1 µL | 1 µL | 0 | 0 |
| 5 mM phosphate buffer | 49 µL | 49 µL | 50 µL | 50 µL |

The wells were covered at room temperature for 30 minutes and incubated by gentle shaking. Each well was then washed with 100 µL 5 mM phosphate buffer 6×. A dye solution was prepared by adding 1 µL of 2 mM dye solution to 49 µL of 5 mM phosphate buffer per sample. 50 µL of 5 mM phosphate buffer was added to the buffer only well.

An initial read absorbance or fluorescence was detected prior to exposure to a light stimulus at the following wavelengths: absorbance of 562 nm; fluorescence emission of 590 nm, and fluorescent excitation of 535 nm.

Samples were exposed to light stimulus at the using an Aurora 50/50. The Aurora 50/50 can also be used with different colored filters (blue, green, red) to define the range of light of interest.

In another variation, PNA was immobilized and target polynucleotides were hybridized at the same time. Enough wells for samples (n) were prepared, along with 3 extra wells for controls by washing 3× with 300 µL of 1×PBST. The DNA or RNA was isolated.

A mixture of PNA probe and sample was prepared as diagramed below:

| | Test | +control | PNA only | Buffer only |
|---|---|---|---|---|
| PNA | 1 µL | 1 µL | 1 µL | 0 |
| Test sample | 1 µL | 1 µL | 0 | 0 |
| 5 mM phosphate buffer | 48 µL | 48 µL | 49 µL | 50 µL |

The mixture was incubate covered for 10-120 minutes (dependent on application) at room temperature gently shaking. The mixture was washed 6× with 100 µL 5 mM phosphate buffer. A dye was prepared as described above. 50 µL of the solution was added to each well except the buffer only well.

Example 18

The following protocol was conducted using plant DNA.

The line was RR 2701 soy. The DNA used was from a purified DNA extraction that contained 62 ng/µL. Samples were serial diluted from 62 ng/µL to 0.062 ng/µL. One µL of this dilution was used in a 50 µL reaction.

A streptavidin plate was washed 3× with 400 µL of Phosphate buffered saline buffer (PBS) (+0.5% TWEEN® (PBST)) at room temperature (RT). All washing, loading and unloading was done using a pipette. To wash, 400 µL of solution was added directly to the well. The solution was then sucked off using the same pipette and tip.

PNA bio-18 (35S) was diluted 1/10 in water (i.e., 1 µL of PNA stock to 9 µL water) (BIO-OO-GATAGTGGGATTGT-GCGT [SEQ ID NO:16], where OO are two linkers.) 1 µL of the diluted PNA was added per 49 µL of PBST. A master mix was made to include all wells to be bound plus one well in excess. Thus if we were to bind 10 wells enough mix was made for 11 wells. (11 µL of the diluted PNA+539 µL PBST). 50 µL of this mix was added to each well. The plate was incubated 1 hour at room temperature ("RT") with gentle shaking on an orbital shaker. DNA was prepared by making serial dilutions (1/10, 1/100, 1/1000) of each DNA sample in water in micro-PCR tubes. Tubes were placed in a thermal cycler and a denature program was run (95° C. for 5 min). Upon completion tubes were placed on ice until needed. After incubation the plate was washed 3× with PBST as described above. The plate was then washed 3× with 5 mM $PO_4$ buffer (pH 5.7) as described above. One µL of DNA or diluted DNA sample was added to each well, (GM or non GM DNA, one sample per well). 49 µL of $PO_4$ buffer was added. Plate was gently mixed and incubated 30 min at RT with gentle shaking on an orbital shaker. After incubation the plate was washed 5× with $PO_4$ buffer as described above. 1 µL of 3,3'-diethylthiacarbocyanine dye (3 mM) was added to 49 µL of $PO_4$ buffer (A master mix was made to include all wells plus enough for one more well). 50 µL of dye/buffer was added to each well using a pipette. The plate was then placed in Tecan scanner to monitor fluorescence of the reaction at 535 nm excitation and 590 nm emission. An initial read was conducted at time zero. The plate was then exposed to light stimulus and read in intervals of 1 minute. Data as analyzed in Excel and plotted based on percent change vs time using the equation 100-(sample/PNA dye only)×100.

Figure 20:
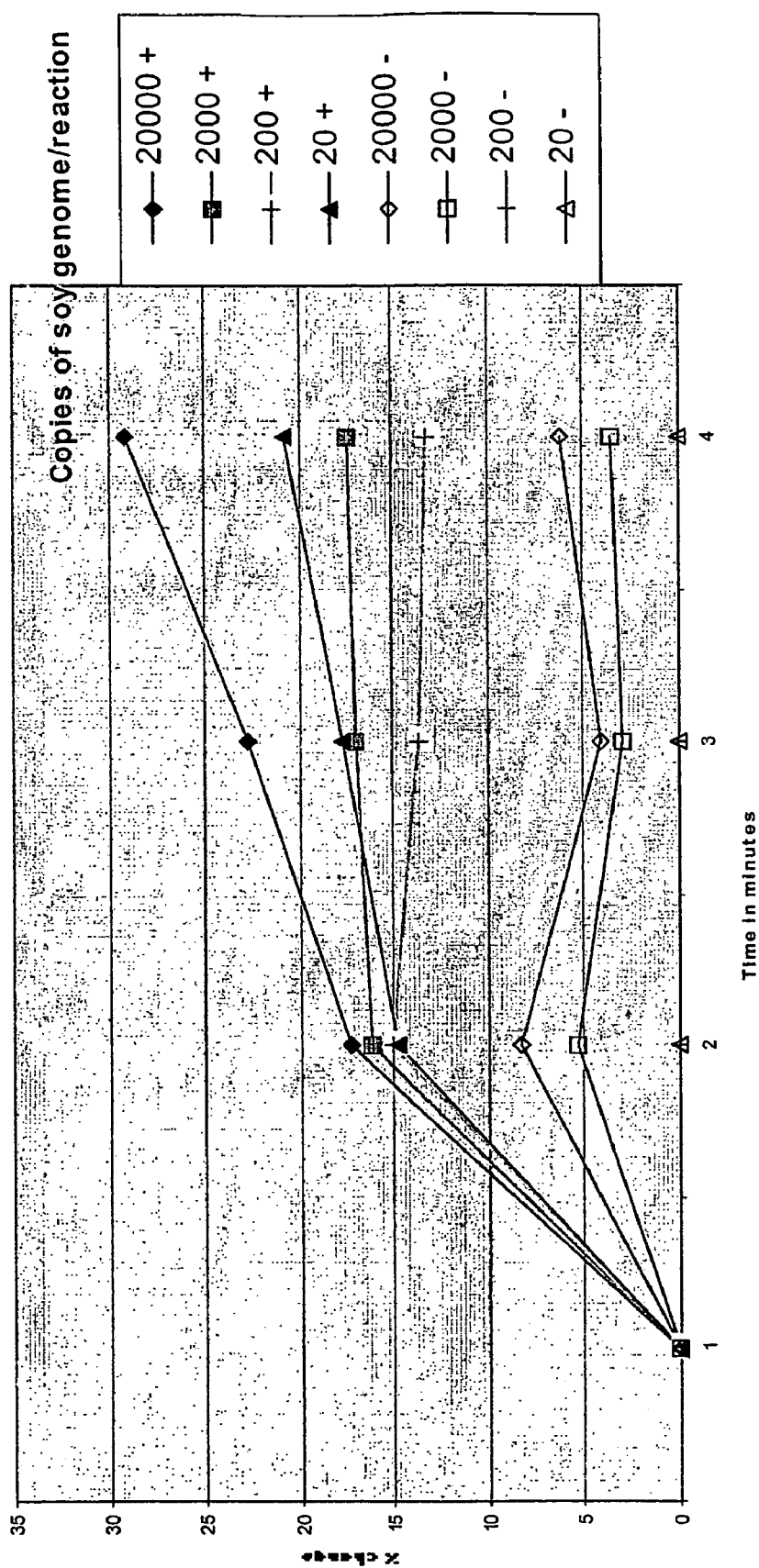
FIG. 20 depicts the detection of different concentrations of soy DNA.
Figure 21:
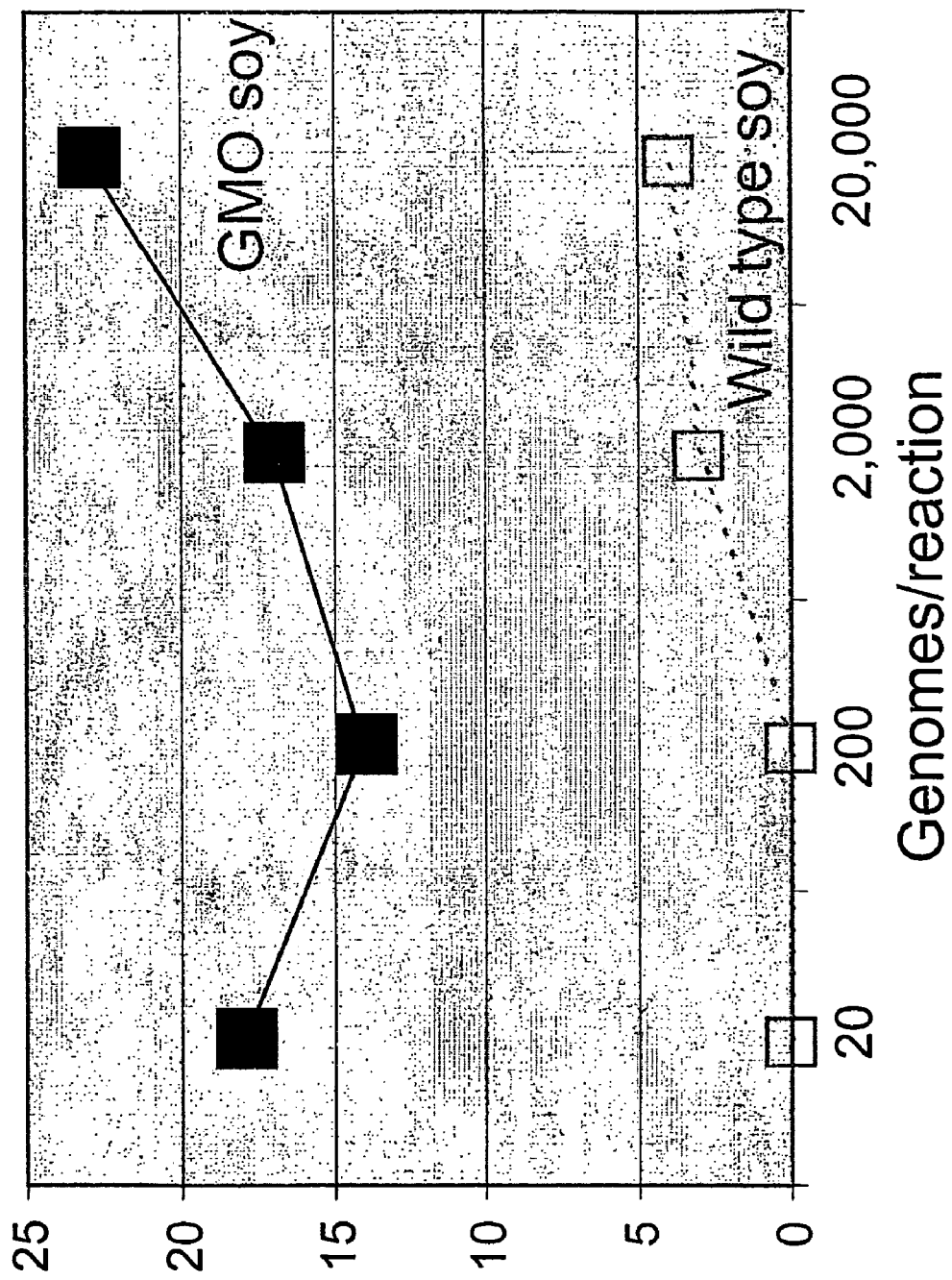
FIG. 21 depicts the percent change in optical property versus the number of genomes of GMO positive soy.

FIG. 20 depicts the detection of different concentrations of soy DNA. These are indicated by the +. Soy DNA that did not contain the GMO sequence was close to background levels. These are indicated by the −. The method was able to detect 0.0625 ng GMO soy DNA, which corresponds to approximately 21 genomes. FIG. 21 depicts the percent change in optical property versus the number of genomes of GMO positive soy and wild type soy that does not contain the PNA target sequence.

Example 19

The following reaction shows detection of a target polynucleotide in phosphate buffer alone and with various TWEEN® 20 concentrations. Similar experiments were done with other nonionic detergents including NP-40 and Triton® X-100.

The following items were used in the protocol: a) 10 µM PNA (ABI); b) 2 mM 3,3'-diethylthiacarbocyanine iodide (Sigma-Aldrich, catalog #173738) dye; c) 5 mM buffer (pH 5.5) (2 mL 100 mM $Na_2HPO_4.7H_2O$+48 mL $NaH_2PO_4.H_2O$/L); d) test samples.

Enough wells were prepared for the number of samples to be tested plus 3 for controls. The DNA or RNA was isolated. Each test reaction contained: 1 µL probe, 47, µL buffer, and 1 µL sample to form a mixture.

| +control | Test sample | PNA only | Buffer only |
|---|---|---|---|
| 1 µL + control | 1 µL sample | 1 µL buffer | 50 µL buffer |

To all wells EXCEPT buffer only well, add 49 µL of mixture was added, and the solution was mixed gently.

An initial fluorescence measurement was made without exposure to a light stimulus at an emission setting at 590 nm and an excitation setting at 535 nm. The samples were exposed to light stimulus using an Aurora 50/50 and the absorbance and/or fluorescence was measured after every 60 seconds of exposure to a light stimulus. The standard 5 mM phosphate buffer (pH 5.5) was used and compared with reactions in phosphate buffer containing 0.05%, 0.1%. 0.5%. 1.0%, 1.5%, and 2% TWEEN® 20.

FIG. 22 depicts the emission using different concentrations of TWEEN®. (■) represents the reaction with target DNA, (□) represents probe alone, (Δ) represents dye in buffer, and (*) represents buffer alone.

Figure 23:
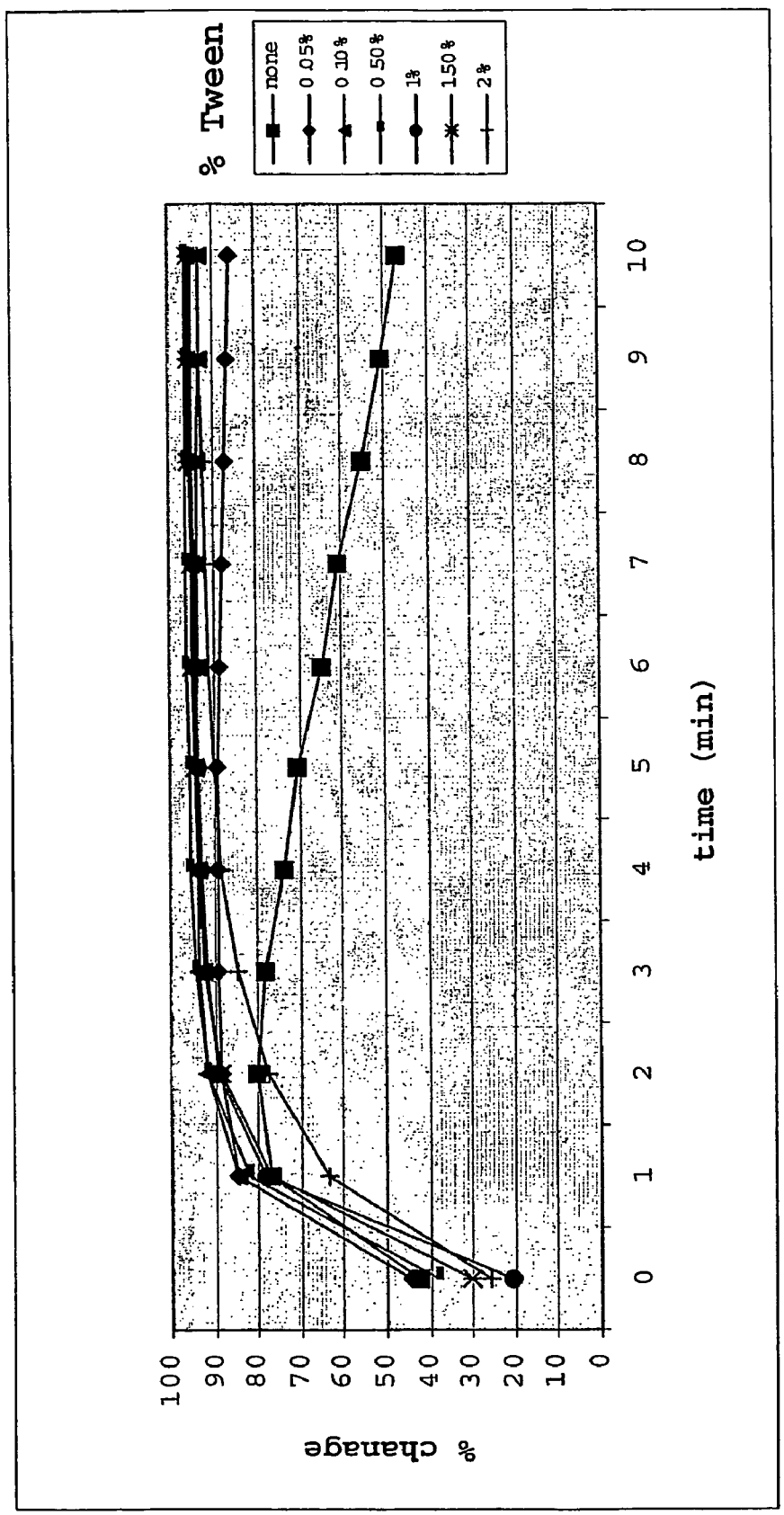
FIG. 23 depicts the percent change in emission for different concentrations of TWEEN® 20.

FIG. 23 depicts the % change in emission for different concentrations of TWEEN®.

Example 20

This example demonstrates that the reaction can use nucleic acid analogs other than PNAs. The present reaction uses locked nucleic acids (LNAs). Various concentrations of TWEEN® 20 in the phosphate buffer were also tested.

The following LNA sequences were used:

```
LNA-A    TG^mC^mCt^mC^mC^mCGTAG.    [SEQ ID NO:25]

LNA-B    tGc^mCt^mCc^mCgTaG.        [SEQ ID NO:26]

LNA-C    tGccTcc^mCgtAg.            [SEQ ID NO:27]
```

Lower case letter represent DNA, upper case letters represent LNA and $^m$ represents methylation of the following C.

Reactions were conducted in liquid form in accordance with the methods disclosed in Example 19, above.

Figure 24:
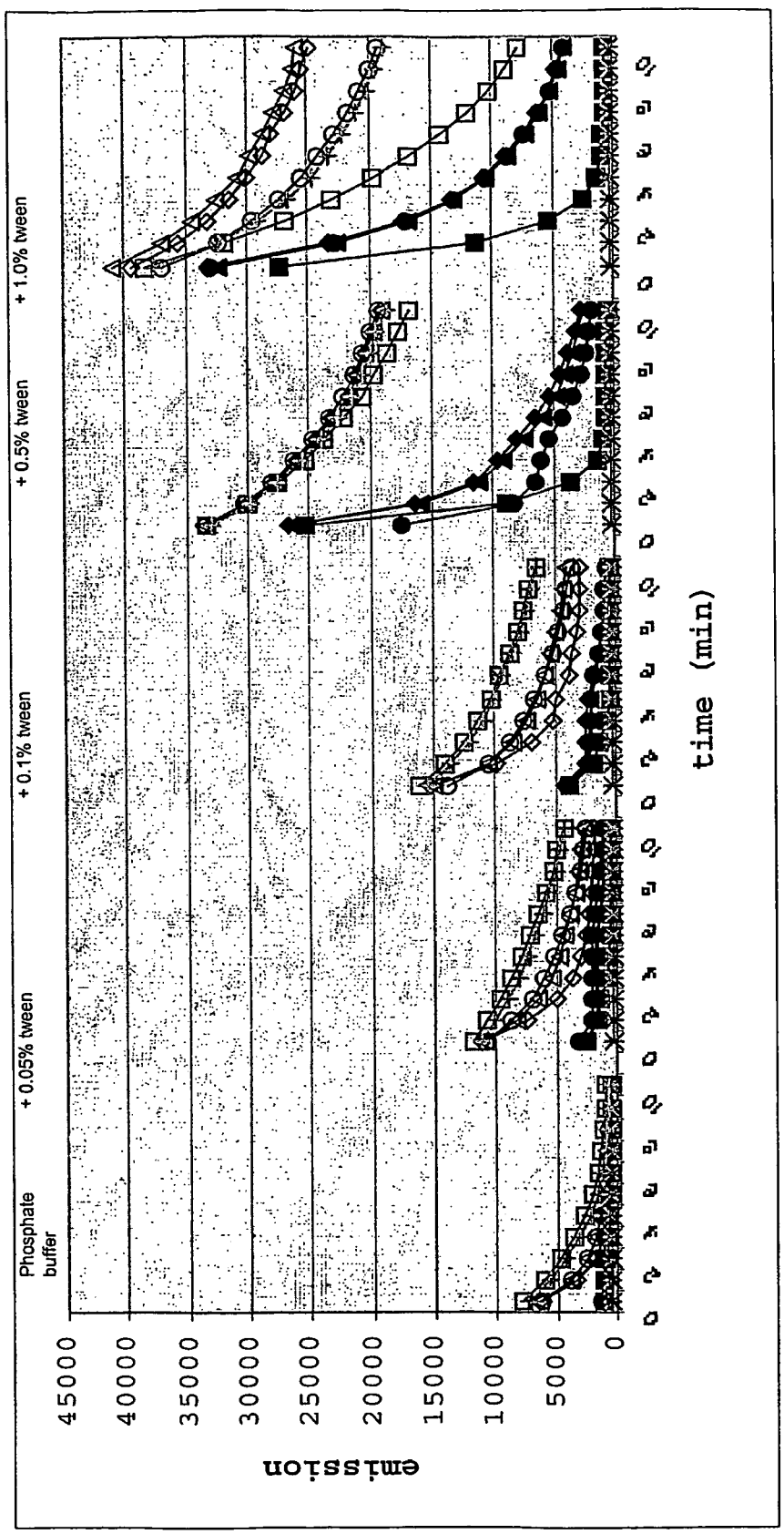
FIG. 24 compares a reaction using PNA probes to a reaction using LNA probes in a liquid format with different concentrations of TWEEN® 20.

FIG. 24 compares the raw data with PNA probes and with LNA probes in the liquid reaction. Standard reaction in phosphate buffer was compared to various concentrations of TWEEN® 20 added to the phosphate buffer. Solid symbols represent test reaction while open symbols are the respective probes only. (■, □) PNA; (♦, ◊) LNA-A; (▲, Δ) LNA-B; (●, ○) LNA-C.

Figure 25:
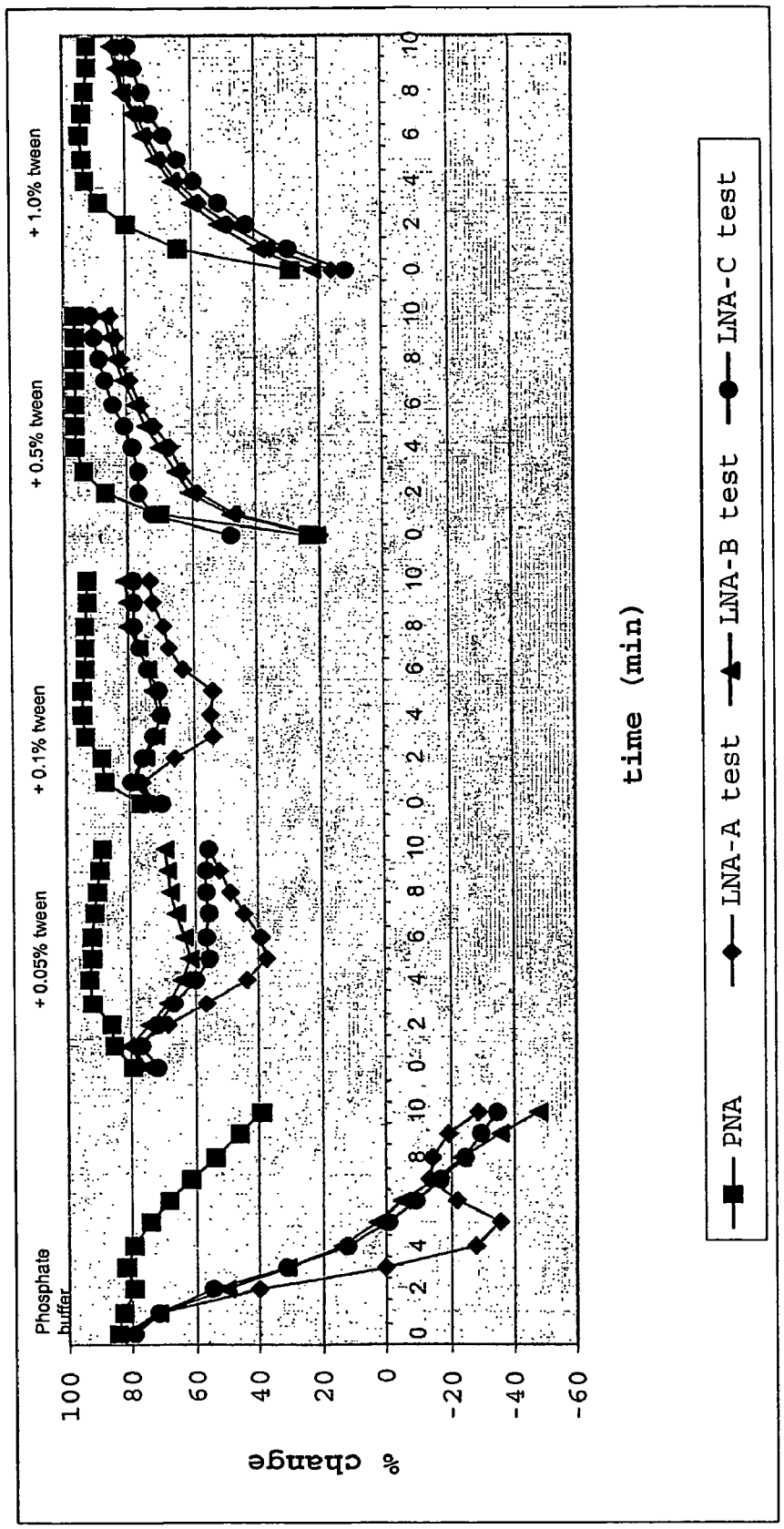
FIG. 25 depicts the percent change in emission using PNAs versus LNAs.

FIG. 25 depicts the percent change in emission using PNAs versus LNAs. (■) represents the percent change in the reaction when compared to the PNA probe alone. (♦) represents the percent change in the LNA-A test reaction when compared to the LNA-A probe and dye alone. (▲) represents the percent change in the LNA-B test reaction when compared to the LNA-B probe alone. (●) represents the percent change in the LNA-C test reaction when compared to the LNA-C probe alone.

Example 21

The assay method may also be used to detect hepatitis C virus. Using standard methods hepatitis C virus RNA was isolated from plasma that had a known amount of hepatitis C virus present. Using this isolated RNA reactions were conducted in liquid form in accordance with the methods disclosed in Example 19, above.

Figure 26:
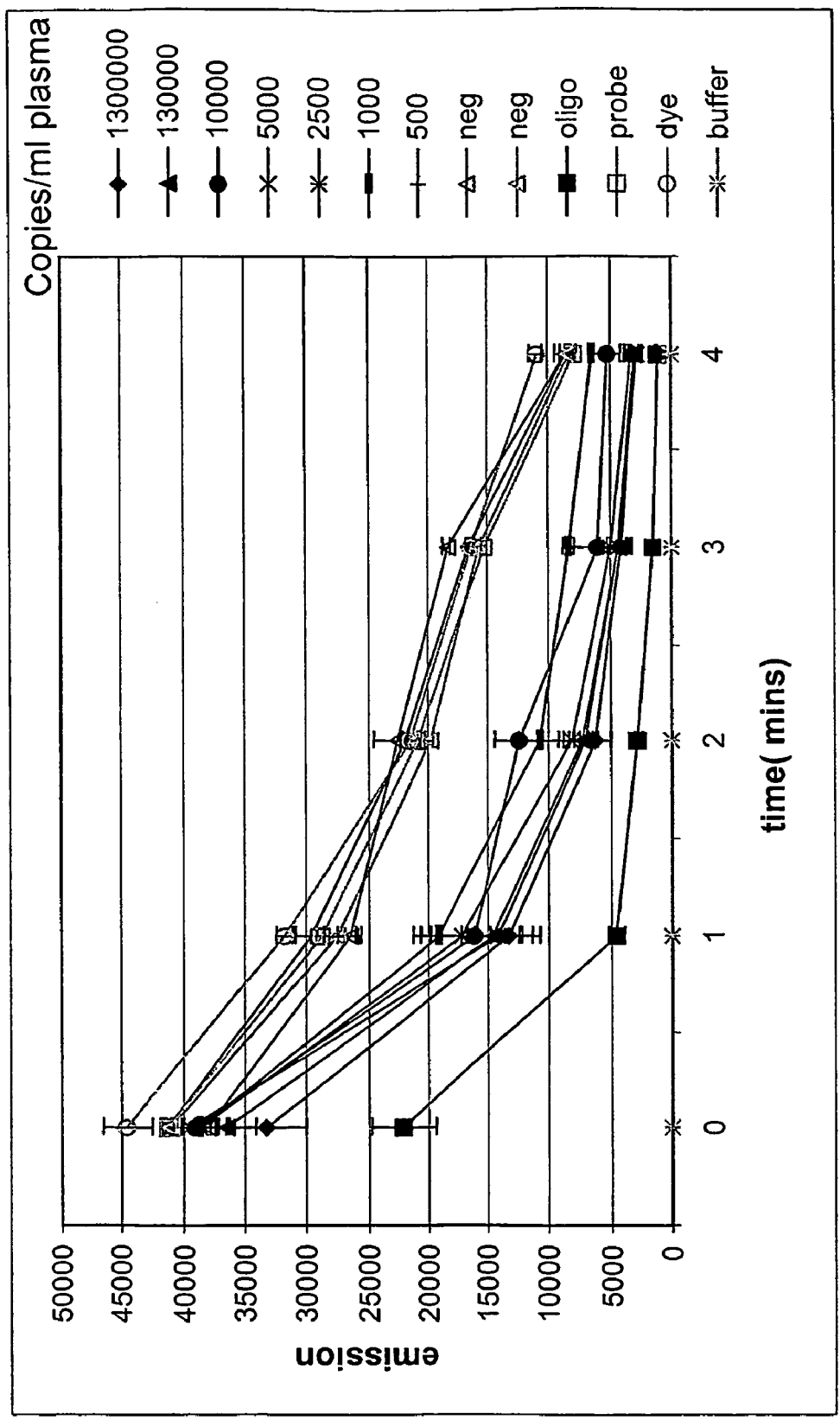
FIG. 26 depicts the detection of hepatitis C virus using different quantities of viral RNA.

FIG. 26 depicts the detection of hepatitis C virus probe using different quantities of plasma. The rate of change of optical property is different for viruses even in very low copy numbers.

Figure 27:
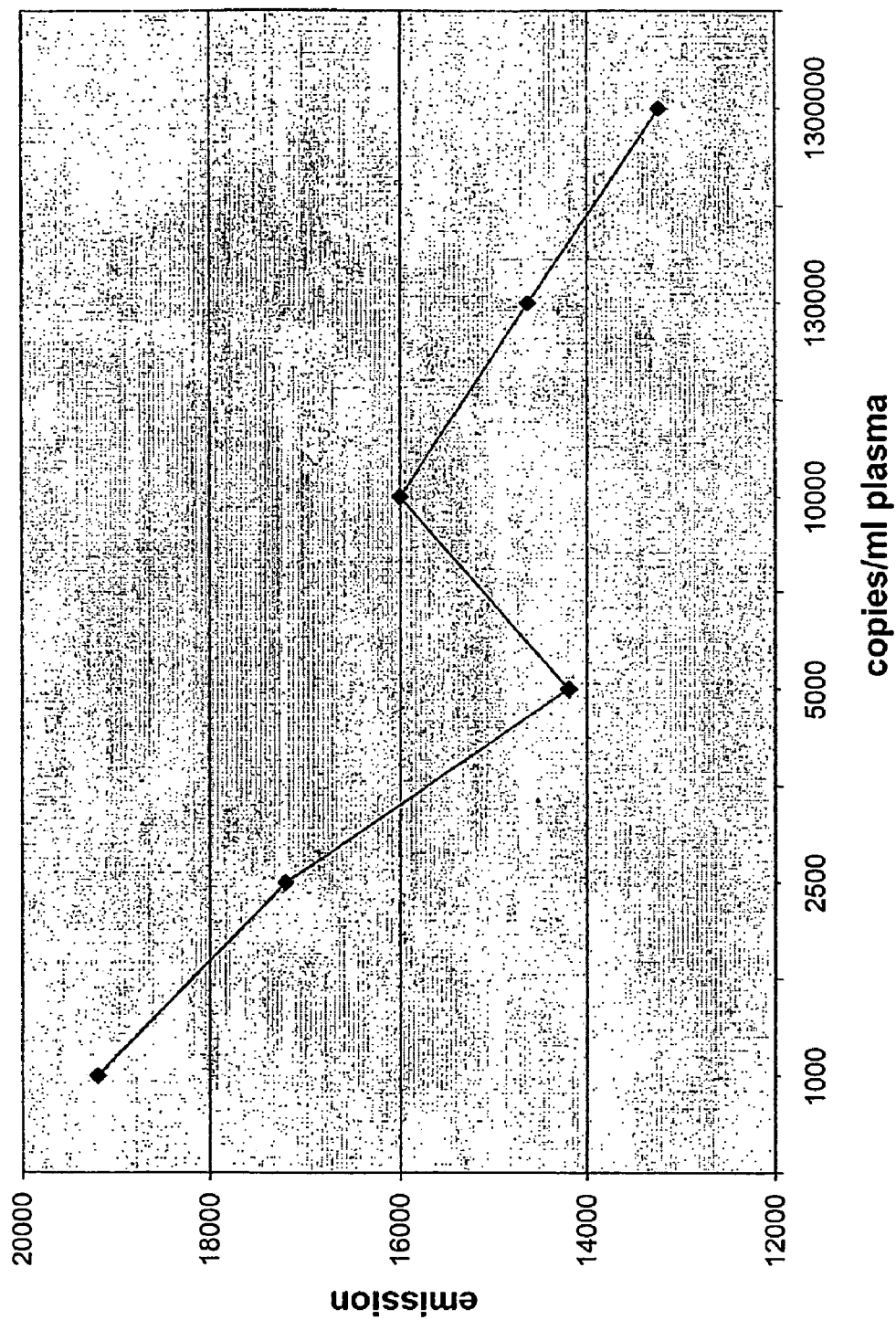
FIG. 27 depicts the emission of reactions with different amounts of HCV RNA one minute after exposure to light stimulus.

The copy number of hepatitis C virus can also be quantitated. FIG. 27 depicts the emission of the dye obtained when different number of hepatitis C virus RNA were introduced into the assay. Lower numbers of virus RNA in the system generally have lower fluorescent emissions after one minute.

Example 22

This example demonstrates that the methods may be used to identify and/or quantify a target polynucleotide in bacteria.

500 µL of bacterium (either *E. coli* or *Bacillus cereus*) culture grown overnight in TSB (tryptic soy broth) was pelleted by spinning for 5 minutes at 6000 rpm then resuspended in 500 µL of phosphate buffer then set at room temperature for 5 minutes. After this the PNA (either 5'bio-oo-gatagtgggat-tgtgcgt [SEQ ID NO:16] for the 35S sequence or 5' Bio-OO-TGAGTGTGTGGCTTTCG 3' [SEQ ID NO:19] for the non-specific HCV negative control sequence) and dye was added to the system, exposed to light stimulus and readings taken.

The following table shows the test conditions for reaction in microwell with a 50 µL reaction volume.

|  | P/O test | Probe only | Dye only | Bacteria test | Bacteria dye |
| --- | --- | --- | --- | --- | --- |
| PNA | 5 µL | 5 µL |  | 5 µL |  |
| Oligo | 5 µL |  |  |  |  |
| Bacterial culture |  |  |  | 43 µL | 43 µL |
| Dye | 2 µL | 2 µL | 2 µL | 2 µL | 2 µL |
| Phosphate buffer | 38 µL | 43 µL | 48 µL |  | 5 µL |

Emission data was collected using a Genios spectrophotometer at an excitation wavelength of 535 nm and an emission wavelength of 590 nm. After an initial zero minute read, the samples were exposed to light stimulus from the Aurora 50/50 light for 60 seconds. The fluorescence was measured every 60 seconds for 10 minutes.

Figure 28:
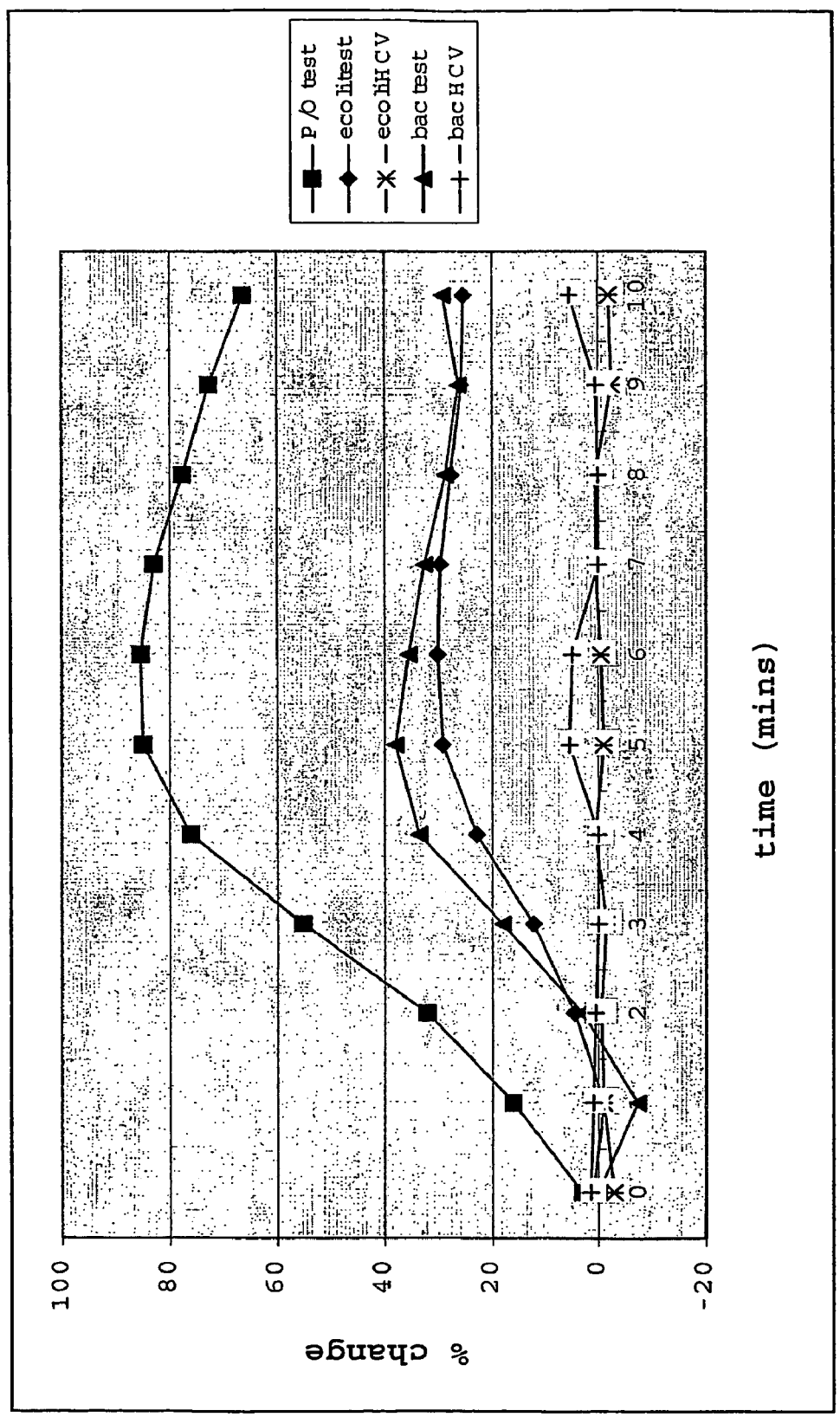
FIG. 28 depicts the percent change in emission using bacteria and nucleic acid analogs that are either HCV or bacterial specific.

FIG. 28 depicts the rate of change in the fluorescence compared to the absence of a nucleic acid analog/polynucleotide hybrid for each sample. The sample of target *E. coli* or *B. cereus*, was detected by the 16S PNA probe in the assay (closed diamond and closed triangle, respectively, but target *E. coli* or *B. cereus*, was not detected by the viral HCV PNA probe in the assay (x, and +, respectively. The (black square) shows the positive control with oligocomplementary to the 16S sequence as the target polynucleotide.

Example 23

Oligonucleotides (5' tgtgaacgca 3' [SEQ ID NO:31] and 5' tgcgttcaca 3' [SEQ ID NO: 32]) were mixed in annealing buffer (10 mM Tris, pH 7.5-8.0, 50 mM NaCl, 1 mM EDTA) to 10 mM and heated at 95° C. for 10 minutes in a thermal cycler. After heating the oligo mixture was allowed to cool at room temperature for 1 hour. One microliter of this mix was used per reaction.

PNAs N Bio-OO-gatagtgggattgtgcgt C [SEQ ID NO:33] and N tcacatcaatccact-lys C [SEQ ID NO:34] were used mixed of individually at 10 mM in reaction buffer (5 mM $PO_4$+0.05% TWEEN®). One microliter of each mix was used per reaction.

10 mM, 3,3'-diethylthiacarbocyanine dye stock was diluted to 4 mM in reaction buffer. One microliter of this mix was used per reaction.

Example 24

This example illustrates that rates of change in optical properties of dyes can differ for different dyes and different concentrations.

The dyes used were 3,3'-diethylthiacarbocyanine (DiSC3) or 3,3'-diethylthiadicarbocyanine (DiSC5) (Sigma, Milwaukee). The target polynucleotide and the PNA molecule are 15mers. The target polynucleotide has a sequence of 5' AGTGGATTGATGTGA 3' [SEQ ID NO:28]. The PNA molecule has a sequence of 5' TCACATCAATCCACT-LYS [SEQ ID NO:18].

The samples were run in 50 µL volume in PCR tubes according to the following procedure. Sample "A and C" contained buffer. Sample "B and D" contained 4 pmoles PNA and 4 pmoles of the target polynucleotide in buffer. All samples were heated to 95° C., and then cooled to room temperature. 3,3'-diethylthiadicarbocyanine was added to tubes A and B. The dye was added to each sample at a final concentration of 9 µM, forming a light blue solution. 3,3'-diethylthiacarbocyanine was added to tubes C and D. The dye was added to each sample at a final concentration of 9 µM, forming a pink solution. The tubes were exposed to a light stimulus for 140 seconds and observed in 20 second intervals, during which time the Sample D rapidly changed in color from pink to clear. Sample A, B and C remained unchanged in color.

The samples were then heated to 95° C. for 2 minutes, and observed for 100 seconds in 20 second intervals as the samples cooled to room temperature. No color change was observed in Samples A, B, C or D. The samples were again heated again to 95° C. for 2 minutes, and observed for 100 seconds in 20 second intervals as the sample cooled to room temperature. No color change was observed in Samples A, B, C or D.

Sample C, containing the dye and buffer, showed no color change when exposed to the light stimulus or during the heating/cooling cycles, indicating the dye is stable under these conditions. Sample D, containing PNA, the target nucleotide, and the dye, changed in color from pink to clear upon exposure to the light stimulus. The pink color did not return as a result of the heating/cooling cycles. Sample A and B also did not change color during the light exposure or heating/cooling cycles.

Example 25

This example illustrates that the methods may be used to identify or quantify a target polynucleotide.

All reaction use:

A. 100 mM PNA probe stock in $H_2O$. Dilute 1/50 (2 µM) and use 2 µL per 50 µL reaction (4 pmoles).

B (1) 100 mM DNA oligo stock in H$_2$O. Dilute 1/50 (2 μM) and use 2 μL per 50 μL reaction (4 pmoles); or (2) Genomic DNA is used at approximately 2 ng (or less) per reaction.

C. 5 mM phosphate (pH 5.5)+TWEEN® 80 (0.05%) buffer.

D. 7.5 mM 3,3'-diethylthiacarbocyanine iodide stock in DMSO. 3 μL is diluted to 15 μM with 1500 μL of phosphate (pH 5.5)+TWEEN® 80 (0.05%) buffer and stored in the dark until use.

E. Molecular grade water.

F. Costar, white with white bottom 384-well microtiter plate.

G. Light source (ballast) with 15W Aurora 50/50 fluorescent bulb.

H. Fluorescent plate reader and computer.

Calculate the number of wells required and prepare enough reagent for triplicate plus 3 for controls in triplicate (PNA only, DNA only, Dye only). Dilute DNA oligo and PNA probe 1/50 (100 μM diluted to 2 μM). Or, dilute genomic DNA to 2 ng/μL.

Each test reaction will contain:

| | |
|---|---|
| PNA probe | 2 μL |
| DNA oligo or genomic DNA | 2 μL |
| water | 16 μL |
| phosphate + TWEEN ® 80 Buffer/dye | 30 μL |
| total volume | 50 μL |

To each reaction well in the microtiter plate add 16 μL of water. The "dye only" well gets 20 μL of water. "PNA only" and "DNA only" each get 18 μL of water. To the appropriate well add 2 μL of DNA oligo (2 μM) or genomic DNA. To the appropriate wells add 2 μL of probe (2 μM).

Cover the wells with tape and mix the plate in the plate reader for 5 seconds. Allow the reactions to sit for at least 10 minutes (this allows time for hybridization of the PNA probe to its complementary target). In a 2 mL tube, add 3 μL of 7.5 mM dye stock to 1500 μL of 5 mM phosphate+TWEEN® 80 buffer. Mix well. With lights dimmed, add 30 μL of phosphate+TWEEN® 80 buffer/dye to each well.

Place the microtiter plate in the plate reader with the parameters of gain of 49, 1 second shake, emission 535 nm and excitation 590 nm and take an initial read at time zero. Expose samples to light using aurora 50/50 and read fluorescence in 2 minute intervals for 30-40 minutes. Graph the data as a function of the decrease in fluorescence verse time.

Example 26

This experiment demonstrates the use of two adjacent ends of two larger PNAs that share homology with a 12mer oligo does drive a reaction where two 6mer overlaps do not drive a reaction.

In this experiment PNAs bio-GATAGTGGGATTGT-GCGT [SEQ ID NO:17] and TCTCTTTTTCCACG-lys [SEQ ID NO:18] were diluted in water to 10 uM working stock. Oligos 5' AGAAGAACGCAC 3' [SEQ ID NO:29] and 5' GTGCGTTCTTCT 3' [SEQ ID NO:30] were diluted in water in the same tube to a 10 μM working stock. The tube was heated for 5 minutes and allowed to cool to room temperature for 10 minutes. A dye stock of 10 mM DiSc3 in DMSO was diluted to a 2 mM working stock in phosphate buffer+0.05% TWEEN® 20. Buffer used was phosphate buffer+0.05% TWEEN® 20.

Reactions were set up by making a dye/buffer working stock by adding 1 μL of 2 mM dye to 46 μL of phosphate buffer+0.05% TWEEN® 20. This was made up as n+2 for excess. 47 μL of the mix as added to a well of a 96 well microtiter plate (clear). To well one, 1 μL of PNA bio-GAT-AGTGGGATTGTGCGT [SEQ ID NO:17] and 1 μL of the double stranded oligo and 1 μL of water was added. To well 2, 1 μL of PNA TCTCTTTTTCCACG-lys [SEQ ID NO:18] and 1 μL of the double stranded oligo and 1 μL of water was added. To well 3, 1 μL of each PNA was added and 1 μL of oligo was added.

An initial fluorescence measurement was made without exposure to a light stimulus at an emission setting at 590 nm and an excitation setting at 535 nm. The samples were exposed to light stimulus using an Aurora 50/50 and the fluorescence was measured after every 30 seconds of exposure to a light stimulus.

Figure 29:
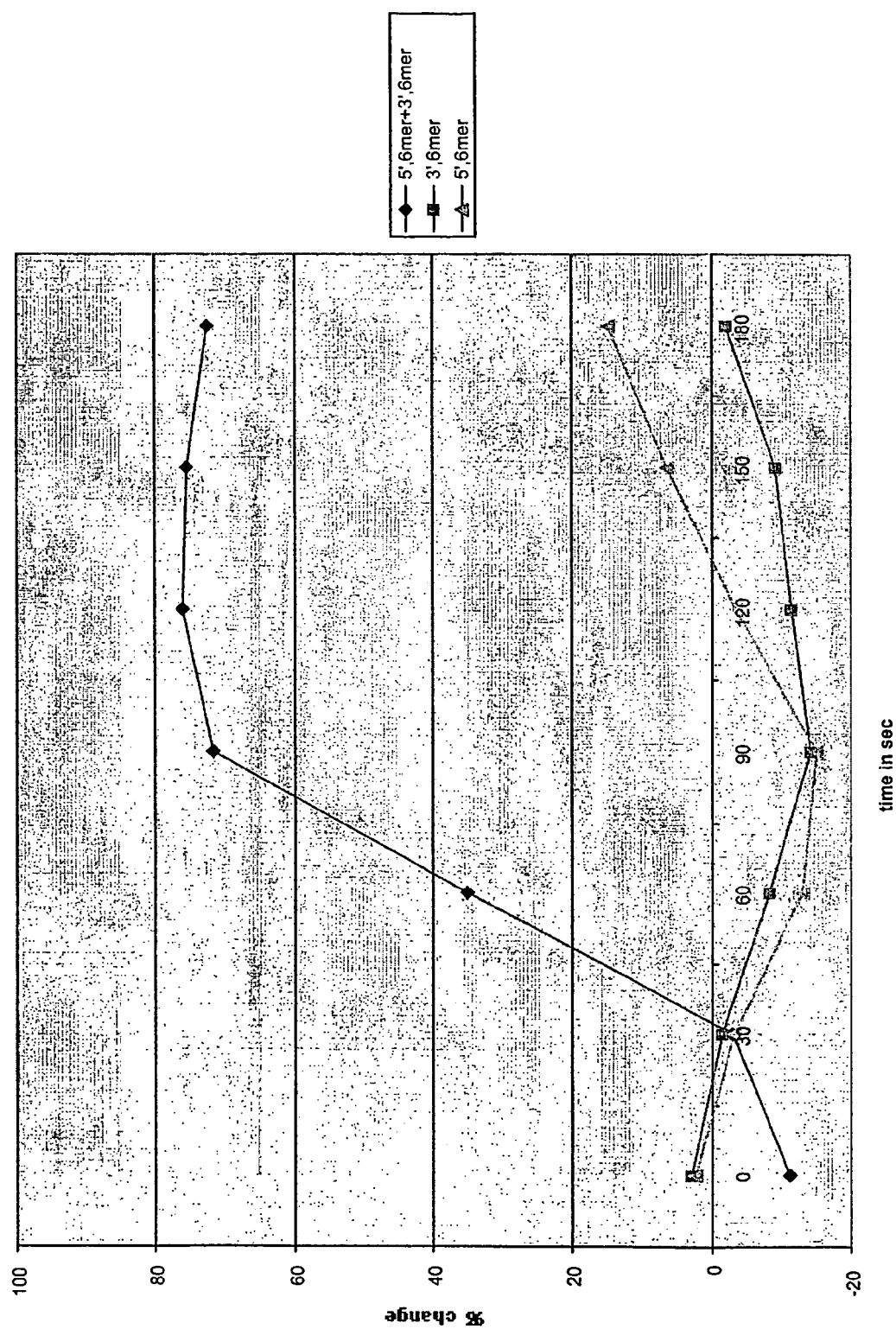
FIG. 29 depicts the percent change in emission using short nucleic acid analogs or short nucleic acid analogs put together.

FIG. 29 depicts the percent change in fluorescent intensity of the reactions. Well 3 which contained both PNA (diamonds), shows a rapid rate for change where both PNAs bind next to each other forming a 12 bp sequence of homology. Wells 1 (triangle) and 2 (squares), each of which only contain one PNA (6 bp sequence of homology) do not produce a change in fluorescence over background.

Example 27

This experiment is to demonstrate the sensitivity of the assay using serial diluted polynucleotide target.

In this experiment PNA CACTGCTGCCTCCCCGTAG-Lys [SEQ ID NO:1] designed to target bacterial 16S ribosomal DNA was diluted in water to a 10 μM working stock. The polynucleotide sequence was 5' CTACGGGAGGCAG-CAGTG 3' [SEQ ID NO:2]. The polynucleotide was serial diluted to produce reactions that have final amounts per reaction of 200 fmoles, 2 fmoles, 200 amoles, 20 amoles, 10 amoles, 5 amoles, 2 amoles, 1 amoles and 0.5 amoles. A dye stock of 10 mM DiSc3 in DMSO was diluted to a 2 mM working stock in phosphate buffer+0.05% TWEEN® 20. Buffer used was phosphate buffer+0.05% TWEEN® 20.

Reactions were set up by making a dye/buffer working stock by adding 1 μL of 2 mM dye and 1 μL of 10 uM PNA working stock to 47 μL of phosphate buffer+0.05% TWEEN® 20. This was made up as n+2 for excess. 49 μL of the mix as added to each well of a 96 well microtiter plate (clear). To each test well, 1 μL of the appropriate serial diluted oligo target was added. To the control dye/PNA well, 1 μL of water was added.

Using a fluorescent plate reader an initial fluorescence measurement was made without exposure to a light stimulus (time zero) at an excitation setting of 535 nm and an emission setting at 590 nm. The samples were exposed to light stimulus using an Aurora 50/50 and the fluorescence was measured after every minute of exposure to a light stimulus for 30 seconds.

Figure 9:
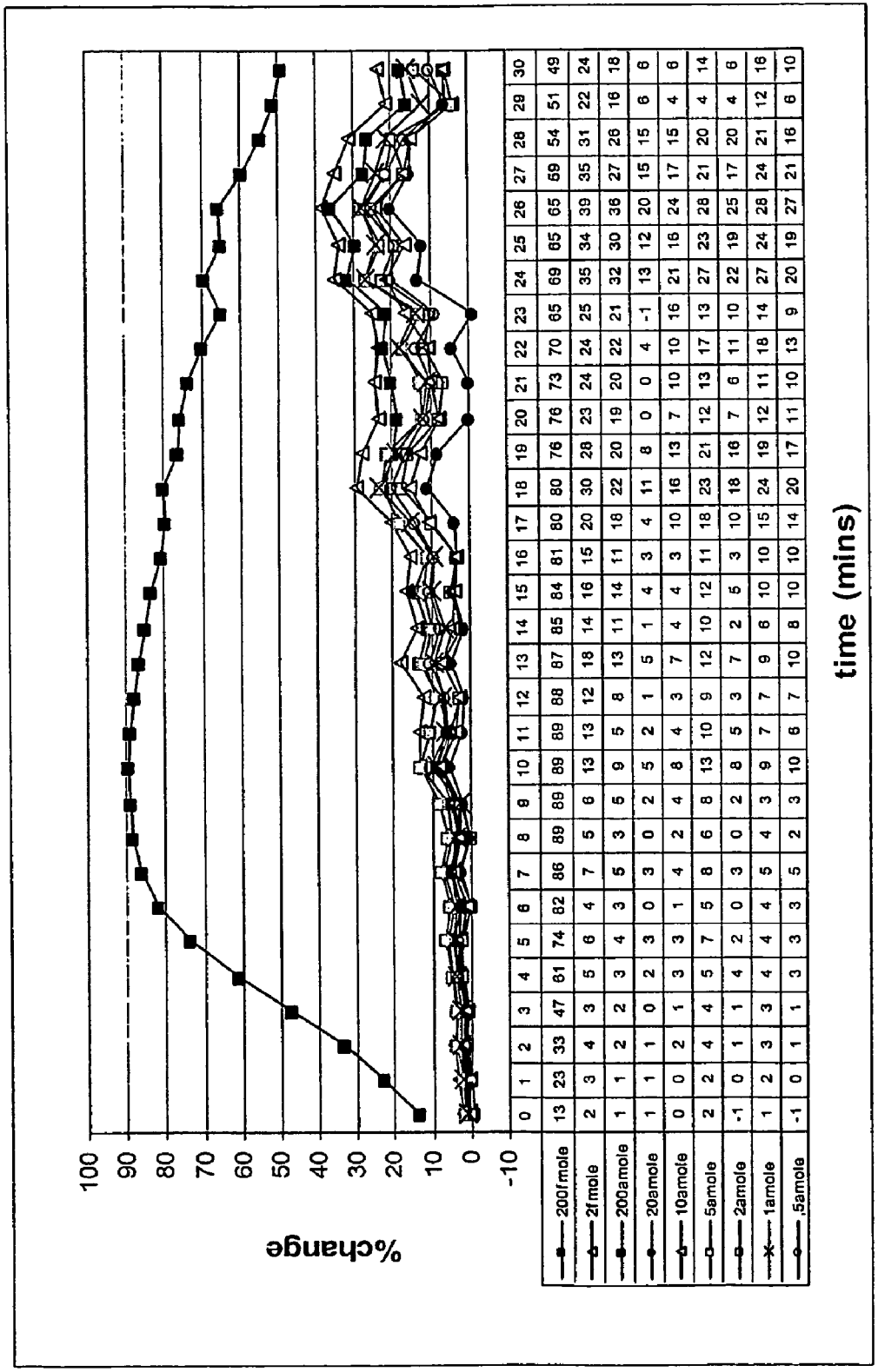
FIG. 9 depicts assay sensitivity with varying test DNA concentrations using a mixed wavelength light source. Each line depicts the percent change in emission of the dye after exposure to a light stimulus at varying DNA concentrations. The PNA was CACTGCTGCCTCCCCGTAG-Lys [SEQ ID NO:1]. The polynucleotide sequence was 5' CTACGGGAG-GCAGCAGTG 3' [SEQ ID NO:2].

FIG. 9 depicts the percent change in fluorescent intensity of the reactions, showing that higher concentrations of target have a greater percent change than reactions with less target. With this specific PNA and target, down to 200 fM of target could be detected.

All publications, patents, and patent applications cited herein are hereby incorporated by reference in their entirety for all purposes to the same extent as if each individual publication, patent, or patent application were specifically and individually indicated to be so incorporated by reference. Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit and scope of the disclosure.

We claim:

1. A method comprising the steps of:
   (a) producing a mixture comprising
      (i) a sample that may or may not contain a target polynucleotide having a target nucleic acid sequence,
      (ii) a nucleic acid analog that is complementary to the target nucleic acid sequence and
      (iii) a cyanine dye, wherein some of the cyanine dye forms a complex with the nucleic acid analog and a target polynucleotide, if present in the sample;
   (b) exposing the mixture to a light stimulus, wherein the light stimulus catalyzes a reaction that causes a decrease in the amount of the cyanine dye in the mixture; and
   (c) correlating the rate of change in an optical property of the mixture to the light stimulus during the period of time subsequent to formation of the complex, wherein the rate of change in the optical property of the mixture caused by the light stimulus is indicative of the presence or amount of the target polynucleotide in the sample.

2. The method of claim 1, further comprising the step of correlating an alteration in the rate of change in the optical property of the mixture with the presence or amount of the target polynucleotide in the sample.

3. The method of claim 1, wherein the optical property is determined by observing one or more of color, absorbance, reflectance or fluorescence.

4. The method of claim 1, wherein the nucleic acid analog is a peptide nucleic acid (PNA) or a locked nucleic acid (LNA).

5. The method of claim 1, wherein the target polynucleotide is DNA or RNA.

6. The method of claim 1, wherein the nucleic acid analog includes a complementary region that is greater than about 4 nucleic acid bases in length and less than about 24 nucleic acid bases in length.

7. The method of claim 1, wherein the nucleic acid analog or the target polynucleotide is immobilized on a solid substrate.

8. The method of claim 2, wherein the light stimulus-causes a higher rate of change in the optical property of the mixture when the nucleic acid analog and the target polynucleotide are present in the sample.

9. The method of claim 2, wherein the light stimulus causes a lower rate of change in the optical property of the mixture when the nucleic acid analog and the target polynucleotide are present in the sample.

10. A method for detecting a single nucleotide polymorphism (SNP), comprising detecting the target polynucleotide in the sample according to the method of claim 1, wherein the target nucleic acid sequence is specific to the SNP, and wherein the detecting of the target polynucleotide identifies the SNP.

11. A method of detecting an organism in a sample, comprising detecting the target polynucleotide in the sample according to the method of claim 1, wherein the target nucleic acid sequence is specific to the organism, and wherein the detecting of the target polynucleotide identifies the presence or amount of the organism.

12. The method of claim 3, wherein the light stimulus, in the presence of the target nucleic acid and complementary nucleic acid analog, results in a reduction in the color of the mixture.

13. The method of claim 1, wherein the cyanine dye is thiacyanine dye.

14. The method of claim 1, wherein the cyanine dye is a carbocyanine dye.

15. The method of claim 14, wherein the cyanine dye is selected from the group consisting of 3,3'-diethylthiacarbocyanine iodide, 3,3'diethylthiadicarbocyanine iodide, 3,3'-diethylthiatricarbocyanine iodide, and 3,3'diethylthiacyanine iodide.

16. The method of claim 1, wherein the cyanine dye is 3,3'diethylthiacarbocyanine iodide.

17. The method of claim 1, wherein the temperature following step (a) is substantially constant.

18. The method of claim 1, wherein the method is performed at a substantially constant temperature.

19. The method of claim 1, wherein the mixture is exposed to the light stimulus for a period of less than 30 seconds.

20. The method of claim 1, wherein the mixture is exposed to the light stimulus for a period of time less than 1 minute.

21. The method of claim 1, wherein the mixture is exposed to the light stimulus for a period of time less than 20 minutes.

22. The method of claim 1, wherein the light stimulus is a filtered light.

23. The method of claim 1, wherein the light stimulus comprises a specific range of wavelengths.

24. The method of claim 23, wherein the range of wavelengths is from a blue light stimulus.

25. The method of claim 23, wherein the range of wavelengths is from a green light stimulus.

26. The method of claim 1, further comprising the step of comparing the rate of change in the optical property of the mixture to a reference mixture either containing a known amount of a target polynucleotide or not containing the target polynucleotide.

27. The method of claim 1, wherein the rate of change in the optical property of the mixture is observed over constant temperature conditions.

28. The method of claim 1, wherein the light stimulus causes a breakdown of the cyanine dye in the mixture.

29. The method of claim 28, further comprising detecting the breakdown of the cyanine dye in the mixture.

30. The method of claim 29, further comprising correlating the breakdown of the cyanine dye with the presence or amount of the target polynucleotide.

31. The method of claim 30, further comprising determining whether exposure to the light stimulus alters the rate of the breakdown of the cyanine dye in the mixture.

32. The method of claim 1, wherein the nucleic acid analog is a peptide nucleic acid (PNA).

33. The method of claim 1, further comprising the step of correlating the rate of change in the optical property of the mixture to the amount of the target polynucleotide in the sample.

34. The method of claim 1, wherein the correlating step is at a point of time that allows differentiation between the presence or absence or differentiation of the amount of the target polynucleotide in the sample.

* * * * *